United States Patent
Moon

(10) Patent No.: US 11,322,692 B2
(45) Date of Patent: May 3, 2022

(54) ORGANIC ELECTROLUMINESCENT COMPOUND AND ORGANIC ELECTROLUMINESCENT DEVICE COMPRISING THE SAME

(71) Applicant: ROHM AND HAAS ELECTRONIC MATERIALS KOREA LTD., Chungcheongnam-do (KR)

(72) Inventor: Doo-Hyeon Moon, Gyeonggi-do (KR)

(73) Assignee: Rohm and Haas Electronic Materials Korea Ltd.

( * ) Notice: Subject to any disclaimer, the term of this patent is extended or adjusted under 35 U.S.C. 154(b) by 96 days.

(21) Appl. No.: 16/606,796

(22) PCT Filed: Apr. 11, 2018

(86) PCT No.: PCT/KR2018/004246
§ 371 (c)(1),
(2) Date: Oct. 21, 2019

(87) PCT Pub. No.: WO2018/194314
PCT Pub. Date: Oct. 25, 2018

(65) Prior Publication Data
US 2020/0381630 A1 Dec. 3, 2020

(30) Foreign Application Priority Data

Apr. 19, 2017 (KR) .......... 10-2017-0050573

(51) Int. Cl.
*C07D 403/04* (2006.01)
*C09K 11/06* (2006.01)
*H01L 51/50* (2006.01)
*H01L 51/00* (2006.01)

(52) U.S. Cl.
CPC ........ *H01L 51/0067* (2013.01); *C07D 403/04* (2013.01); *C09K 11/06* (2013.01); *H01L 51/0072* (2013.01); *C09K 2211/1018* (2013.01); *H01L 51/5072* (2013.01); *H01L 51/5092* (2013.01); *H01L 51/5096* (2013.01)

(58) Field of Classification Search
CPC .. C07D 401/04; C07D 401/10; C07D 403/04; C07D 403/10; C07D 487/16; C07F 7/081; C09K 11/06; C09K 2211/1007; C09K 2211/1011; C09K 2211/1018; C09K 2211/1044; C09K 2211/1059; H01L 51/0067; H01L 51/0072; H01L 51/5072; H01L 51/508; H01L 51/5092; H01L 51/5096
See application file for complete search history.

(56) References Cited

U.S. PATENT DOCUMENTS

| 8,318,325 B2 | 11/2012 | Lee et al. |
| 2016/0248024 A1 | 8/2016 | Shin et al. |
| 2017/0141329 A1 | 5/2017 | Koenen et al. |

FOREIGN PATENT DOCUMENTS

| KR | 2014-0140298 A | 12/2014 | |
| KR | 2014-0141970 A | 12/2014 | |
| KR | 2015-0009297 A | 1/2015 | |
| KR | 2015-0042386 A | 4/2015 | |
| KR | 2015-0043571 A | 4/2015 | |
| KR | 2015/080966 | * 10/2015 | ........... C07D 239/70 |
| KR | 2015-0122343 A | 11/2015 | |
| KR | 2015-0124000 A | 11/2015 | |
| KR | 2016-0127503 A | 11/2016 | |

* cited by examiner

*Primary Examiner* — Erich A Leeser
(74) *Attorney, Agent, or Firm* — G. Creston Campbell

(57) ABSTRACT

The present disclosure relates to an organic electroluminescent compound and an organic electroluminescent device comprising the same. By comprising the organic electroluminescent compound of the present disclosure, an organic electroluminescent device having low driving voltage, high luminous efficiency, and/or improved lifespan characteristics can be provided.

8 Claims, No Drawings

ORGANIC ELECTROLUMINESCENT COMPOUND AND ORGANIC ELECTROLUMINESCENT DEVICE COMPRISING THE SAME

TECHNICAL FIELD

The present disclosure relates to an organic electroluminescent compound, and an organic electroluminescent device comprising the same.

BACKGROUND ART

An electroluminescent (EL) device is a self-light-emitting device with the advantages of providing a wider viewing angle, a greater contrast ratio, and a faster response time. The first organic EL device was developed by Eastman Kodak in 1987, by using small aromatic diamine molecules and aluminum complexes as materials for forming a light-emitting layer (see Appl. Phys. Lett. 51, 913, 1987).

An organic EL device changes electric energy into light by applying electricity into an organic light-emitting material, and commonly comprises an anode, a cathode, and an organic layer formed between the two electrodes. The organic layer of the organic EL device may be composed of a hole injection layer, a hole transport layer, an electron blocking layer, a light-emitting layer (containing host and dopant materials), an electron buffer layer, a hole blocking layer, an electron transport layer, an electron injection layer, etc.; the materials used in the organic layer can be classified into a hole injection material, a hole transport material, an electron blocking material, a light-emitting material, an electron buffer material, a hole blocking material, an electron transport material, an electron injection material, etc., depending on functions. In the organic EL device, holes from an anode and electrons from a cathode are injected into a light-emitting layer by application of electric voltage, and an exciton having high energy is produced by the recombination of the holes and electrons. The organic light-emitting compound moves into an excited state by the energy and emits light from energy when the organic light-emitting compound returns to the ground state from the excited state.

Studies have been continuing to improve the performance of organic EL devices by using materials suitable for the respective layers in organic EL devices.

For example, an electron transport material actively transports electrons from a cathode to a light-emitting layer and inhibits transport of holes which are not recombined in the light-emitting layer to increase recombination opportunity of holes and electrons in the light-emitting layer. Thus, electron-affinitive materials are used as an electron transport material. Organic metal complexes having light-emitting function such as $Alq_3$ are excellent in transporting electrons, and thus have been conventionally used as an electron transport material. However, $Alq_3$ has problems in that it moves to other layers and shows a reduction of color purity when used in blue light-emitting devices. Therefore, new electron transport materials have been required, which do not have the above problems, are highly electron-affinitive, and quickly transport electrons in organic EL devices to provide organic EL devices having high luminous efficiency.

In addition, an electron buffer layer is a layer capable of improving the problem that the current characteristics in the device changes upon exposure to a high temperature in a panel fabrication process to cause deformation of light emission luminance. The characteristics of the compound contained in the electron buffer layer are important for ensuring stability against high temperature exposure as well as similar current characteristics compared to devices without an electron buffer layer.

Korean Patent Application Laying-Open Nos. KR 2015-0042387 A and KR 2015-0122343 A disclose a benzoquinazoline derivative as a phosphorescent host or as a compound for an electron transport layer in an organic EL device. However, the compounds disclosed in said references have a structure different from the compounds of the present disclosure.

DISCLOSURE OF THE INVENTION

Problems to be Solved

The objective of the present disclosure is to provide an organic electroluminescent compound which can efficiently produce an organic electroluminescent device having excellent lifespan characteristic, and at the same time or selectively, excellent luminous efficiency and/or driving voltage characteristics.

Solution to Problems

According to the prior art, when a nitrogen-containing 6-membered fused naphthalene derivative is used as an organic electroluminescent compound, the nitrogen-containing 6-membered fused naphthalene part is a part exhibiting the lowest unoccupied molecular orbital (LUMO) energy level. The present inventors found that the nitrogen-containing 6-membered fused naphthalene derivative can stabilize moving electrons to improve the lifespan characteristic of a device, but the electron mobility is reduced and the driving voltage is increased. As a result of intensive studies to solve the problem above, the present inventors found that by combining the above derivative with substituents having specific structures, the driving voltage can be lowered, while maintaining the lifespan characteristic of a device.

Specifically, the present inventors found that the aforementioned objective can be achieved by an organic electroluminescent compound represented by the following formula 1:

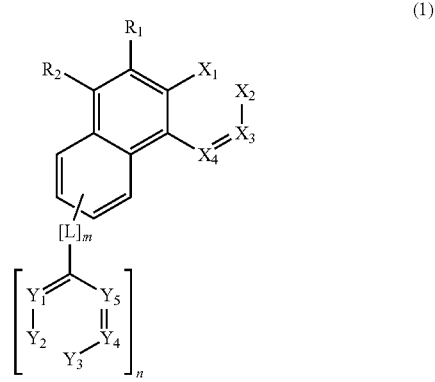

(1)

wherein $X_1$ to $X_4$, each independently, represent CR or N, with a proviso that at least one of $X_1$ to $X_4$ represents N;

$Y_1$ to $Y_5$, each independently, represent $CR_{11}$ or N, with a proviso that at least one of $Y_1$ to $Y_5$ represents N;

R and $R_{11}$, each independently, represent hydrogen, deuterium, a halogen, a substituted or unsubstituted (C1-C30)

alkyl, a substituted or unsubstituted (C6-C30)aryl, or a substituted or unsubstituted (5- to 30-membered)heteroaryl;

$R_1$ and $R_2$, each independently, represent hydrogen, deuterium, a halogen, a substituted or unsubstituted (C1-C30)alkyl, a substituted or unsubstituted (C6-C30)aryl, a substituted or unsubstituted (5- to 30-membered)heteroaryl, a substituted or unsubstituted (3- to 7-membered)heterocycloalkyl, or a substituted or unsubstituted (C3-C30)cycloalkyl; or may be linked to each other to form a substituted or unsubstituted, mono- or polycyclic, (3- to 30-membered) alicyclic or aromatic ring, or a combination thereof, whose carbon atom(s) may be replaced with at least one heteroatom selected from nitrogen, oxygen, and sulfur;

L represents a single bond, a substituted or unsubstituted (C6-C30)aryl(ene), or a substituted or unsubstituted (5- to 30-membered)heteroaryl(ene), with a proviso that L is not a substituted or unsubstituted carbazole, and, if n is 0, L is not a single bond;

m represents an integer of 0 to 4, n represents an integer of 0 to 2, and m+n is 1 or greater; in which if m and n are 2 or greater, each L and each

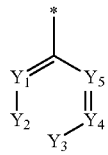

may be the same or different, and, wherein, * represents a bonding site with $(L)_m$; and the heteroaryl(ene) and the heterocycloalkyl contain at least one heteroatom selected from B, N, O, S, Si, and P.

Effects of the Invention

According to the present disclosure, an organic electroluminescent device having excellent lifespan characteristic can be provided. At the same time or selectively, the luminous efficiency and/or driving voltage characteristics of the device can be maintained at an excellent level.

EMBODIMENTS OF THE INVENTION

Hereinafter, the present disclosure will be described in detail. However, the following description is intended to explain the disclosure, and is not meant in any way to restrict the scope of the disclosure.

The term "organic electroluminescent compound" in the present disclosure means a compound that may be used in an organic electroluminescent device, and may be comprised in any material layer constituting an organic electroluminescent device, as necessary.

The term "organic electroluminescent material" in the present disclosure means a material that may be used in an organic electroluminescent device, and may comprise at least one compound. The organic electroluminescent material may be comprised in any layer constituting an organic electroluminescent device, as necessary. For example, the organic electroluminescent material may be a hole injection material, a hole transport material, a hole auxiliary material, a light-emitting auxiliary material, an electron blocking material, a light-emitting material, an electron buffer material, a hole blocking material, an electron transport material, an electron injection material, etc.

The organic electroluminescent material of the present disclosure may comprise at least one of the compound represented by formula 1. The compound represented by formula 1 may be comprised in at least one layer constituting an organic electroluminescent device, for example, in a light-emitting layer, an electron buffer layer and/or an electron transport layer, but is not limited thereto. When comprised in the light-emitting layer, the compound of formula 1 can be comprised as a host. When comprised in the electron buffer layer, the compound of formula 1 can be comprised as an electron buffer material. When comprised in the electron transport layer, the compound of formula 1 can be comprised as an electron transport material.

Hereinafter, the compound represented by formula 1 will be described in detail.

In formula 1,

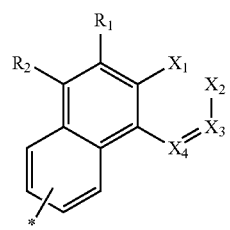

may be represented by the following formulas:

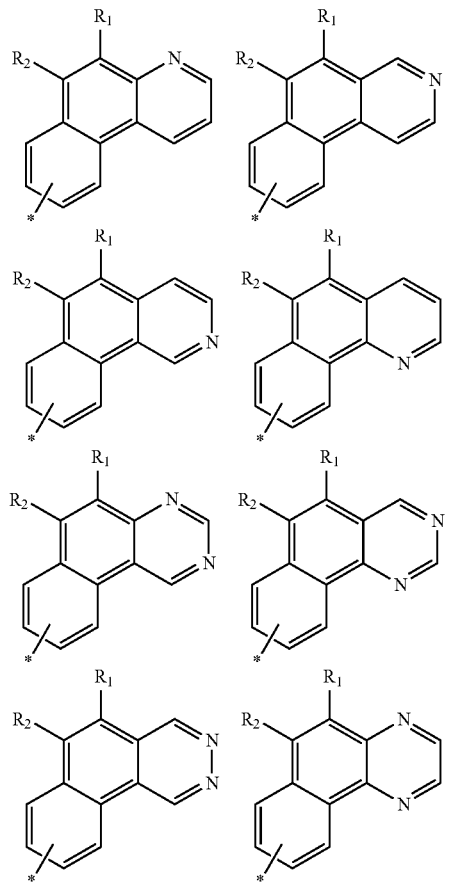

-continued
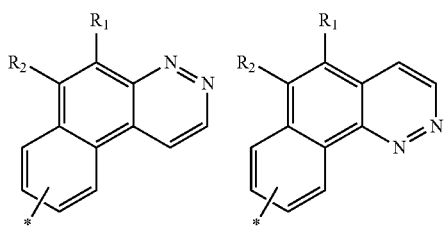
wherein * represents a bonding site with $(L)_m$.
In formula 1,
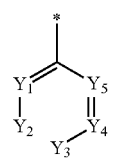
may be represented by the following formulas:
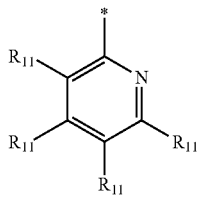 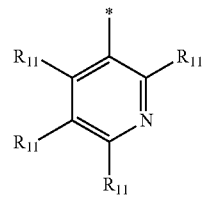
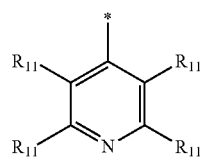 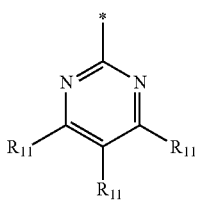
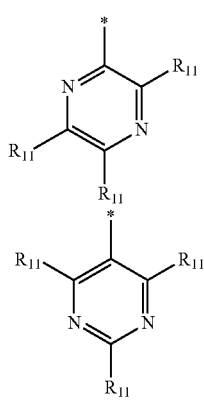 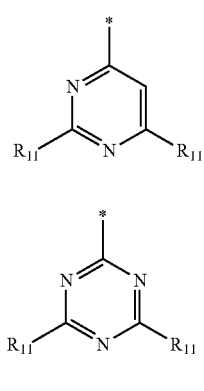
wherein each $R_{11}$ may be the same or different, and * represents a bonding site with $(L)_m$.
Formula 1 may be represented by any one of the following formulas 2 to 7:
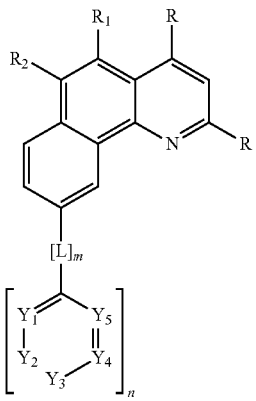
(2)
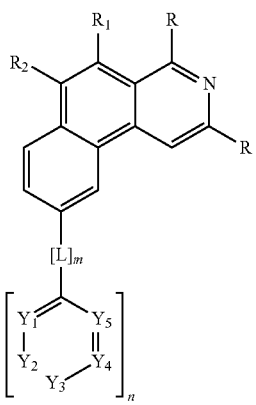
(3)
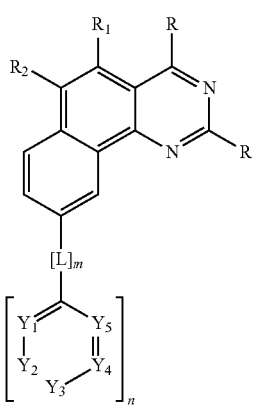
(4)
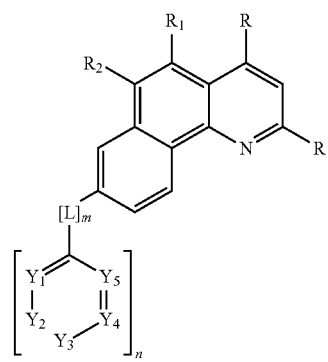
(5)

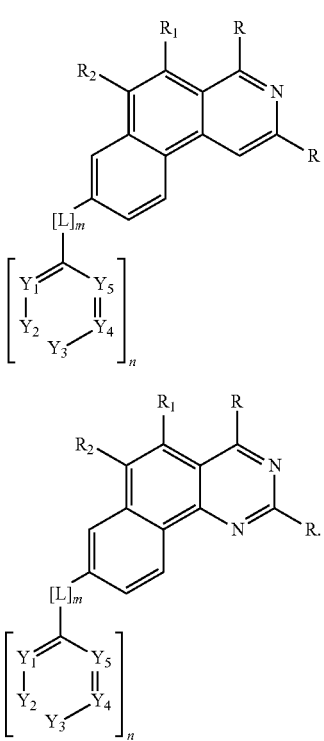

(6)

(7)

In formulas 2 to 7, $Y_1$ to $Y_5$, R, $R_1$, $R_2$, L, m, and n are as defined in formula 1.

In formula 1, $X_1$ to $X_4$, each independently, represent CR or N, with a proviso that at least one of $X_1$ to $X_4$ represents N, and preferably at least two of $X_1$ to $X_4$ represent N.

$Y_1$ to $Y_5$, each independently, represent $CR_{11}$ or N, with a proviso that at least one of $Y_1$ to $Y_5$ represents N.

R and $R_{11}$, each independently, represent hydrogen, deuterium, a halogen, a substituted or unsubstituted (C1-C30) alkyl, a substituted or unsubstituted (C6-C30)aryl, or a substituted or unsubstituted (5- to 30-membered)heteroaryl; preferably, each independently, represent hydrogen, a substituted or unsubstituted (C6-C25)aryl, or a substituted or unsubstituted (5- to 15-membered)heteroaryl; and more preferably, each independently, represent hydrogen, a (C6-C25)aryl unsubstituted or substituted with a (C1-C6)alkyl(s) or a (5- to 15-membered)heteroaryl(s), or a (5- to 15-membered)heteroaryl unsubstituted or substituted with a (C6-C12)aryl(s). Specifically, according to one embodiment of the present disclosure, R and $R_{11}$, each independently, may represent hydrogen, phenyl, naphthyl, biphenyl, spirobifluorenyl, diphenylfluorenyl, dimethylfluorenyl, pyridylphenyl, pyridyl, quinolinyl, phenylpyridyl, etc.

$R_1$ and $R_2$, each independently, represent hydrogen, deuterium, a halogen, a substituted or unsubstituted (C1-C30) alkyl, a substituted or unsubstituted (C6-C30)aryl, a substituted or unsubstituted (5- to 30-membered)heteroaryl, a substituted or unsubstituted (3- to 7-membered) heterocycloalkyl, or a substituted or unsubstituted (C3-C30)cycloalkyl; or may be linked to each other to form a substituted or unsubstituted, mono- or polycyclic, (3- to 30-membered) alicyclic or aromatic ring, or a combination thereof, whose carbon atom(s) may be replaced with at least one heteroatom selected from nitrogen, oxygen, and sulfur. Preferably, $R_1$ and $R_2$, each independently, may represent hydrogen.

L represents a single bond, a substituted or unsubstituted (C6-C30)aryl(ene), or a substituted or unsubstituted (5- to 30-membered)heteroaryl(ene), with a proviso that if n is 0, L is not a single bond. If n is 0, L is a monovalent substituent (aryl, heteroaryl), and if n is 1 or more, L is a divalent substituent (arylene, heteroarylene). Preferably, L represents a single bond, a substituted or unsubstituted (C6-C25)aryl (ene), or a substituted or unsubstituted (5- to 20-membered) heteroaryl(ene); and more preferably, a single bond, a (C6-C25)aryl(ene) unsubstituted or substituted with a (C1-C6) alkyl(s), or a (5- to 20-membered)heteroaryl(ene) unsubstituted or substituted with a (C6-C12)aryl(s). Specifically, according to one embodiment of the present disclosure, L may represent a single bond, phenyl, phenylene, naphthyl, naphthylene, phenanthrenyl, fluoranthenyl, triphenylenyl, spirobifluorenyl, diphenylfluorenyl, fluoranthenylphenyl, triphenylenylphenyl, dimethylfluorenyl, dimethylbenzofluorenyl, pyridylene, phenylisoquinolinyl, etc.

In addition, according to one embodiment of the present disclosure, L may be represented by the following formulas:

Direct bond

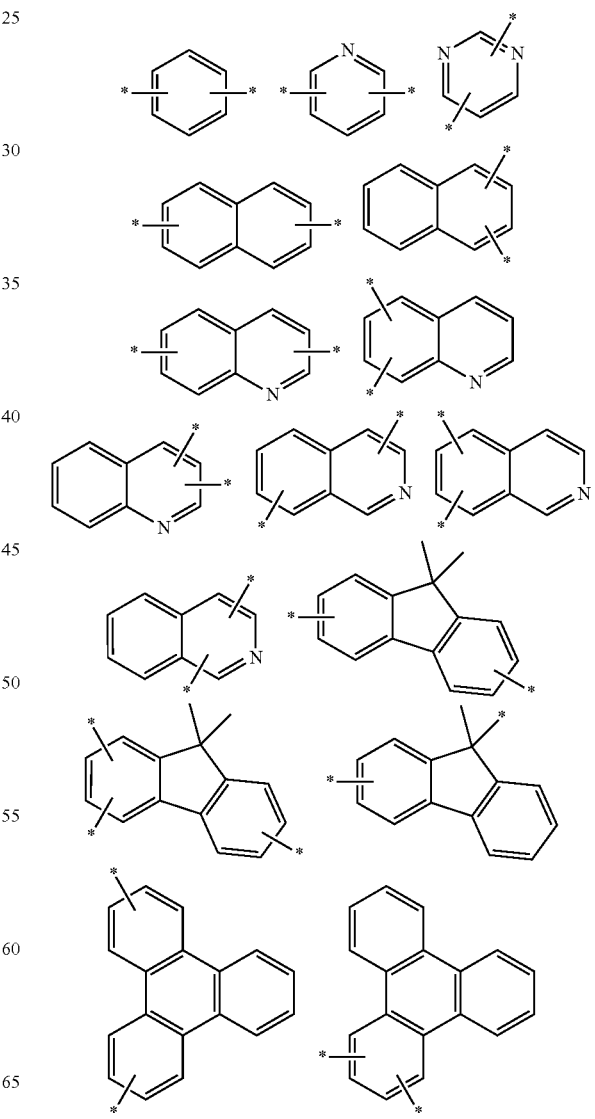

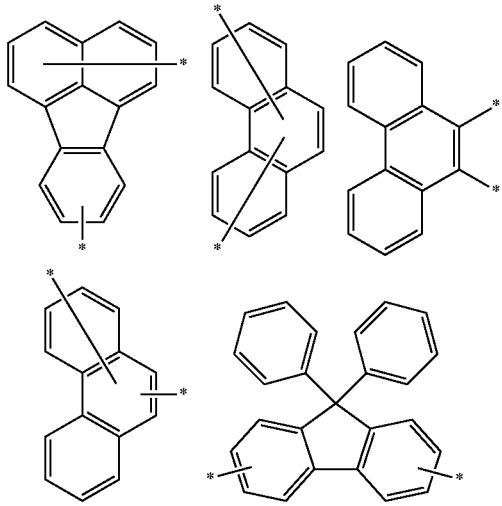

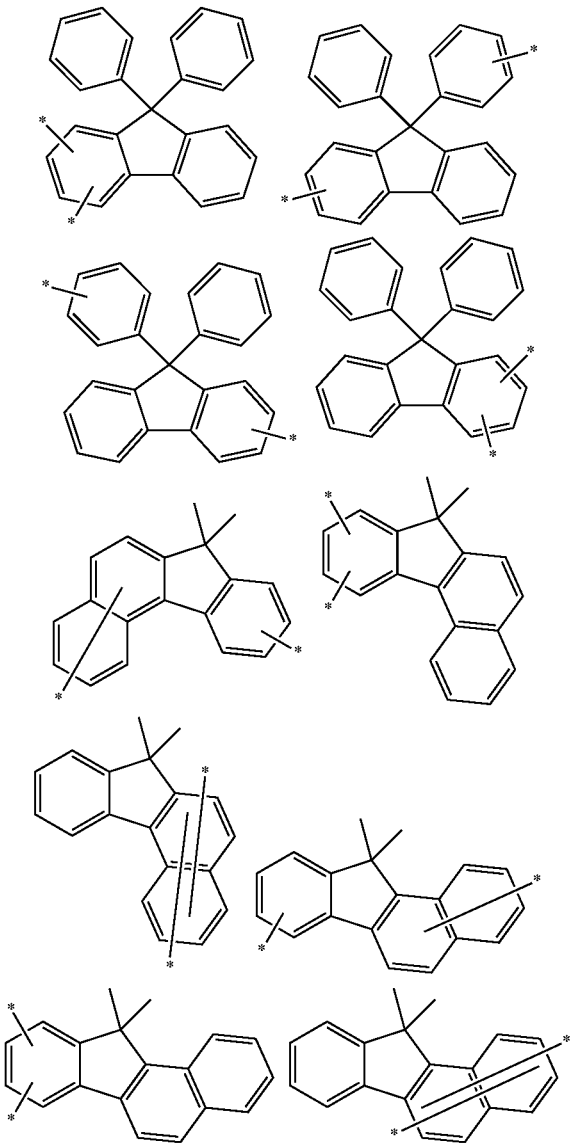

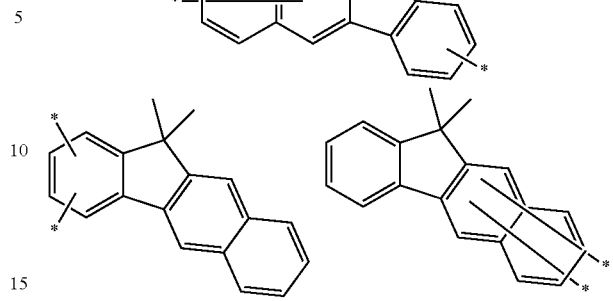

wherein * represents a bonding site.

m represents an integer of 0 to 4, n represents an integer of 0 to 2, and m+n is 1 or greater, in which if m and n are 2 or greater, each L and each

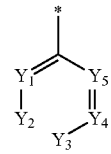

may be the same or different, and, wherein, * represents a bonding site with $(L)_m$. m preferably represents an integer of 0 to 2, more preferably 0 or 1. n preferably represents 0 or 1. According to one embodiment of the present disclosure, if m is 0, n is 1, and if m is 1, n may be 0 or 1.

According to one embodiment of the present disclosure, in formula 1, R and $R_{11}$, each independently, represent hydrogen, a substituted or unsubstituted (C6-C25)aryl, or a substituted or unsubstituted (5- to 15-membered)heteroaryl; $R_1$ and $R_2$, each independently, represent hydrogen; and L represents a single bond, a substituted or unsubstituted (C6-C25)aryl(ene), or a substituted or unsubstituted (5- to 20-membered)heteroaryl(ene).

According to another embodiment of the present disclosure, in formula 1, R and $R_{11}$, each independently, represent hydrogen, a (C6-C25)aryl unsubstituted or substituted with a (C1-C6)alkyl(s) or a (5- to 15-membered)heteroaryl(s), or a (5- to 15-membered)heteroaryl unsubstituted or substituted with a (C6-C12)aryl(s); $R_1$ and $R_2$, each independently, represent hydrogen; and L represents a single bond, a (C6-C25)aryl(ene) unsubstituted or substituted with a (C1-C6)alkyl(s), or a (5- to 20-membered)heteroaryl(ene) unsubstituted or substituted with a (C6-C12)aryl(s).

Herein, "(C1-C30)alkyl" is meant to be a linear or branched alkyl having 1 to 30 carbon atoms constituting the chain, in which the number of carbon atoms is preferably 1 to 20, more preferably 1 to 10, and includes methyl, ethyl, n-propyl, isopropyl, n-butyl, isobutyl, tert-butyl, etc. "(C2-C30)alkenyl" is meant to be a linear or branched alkenyl having 2 to 30 carbon atoms constituting the chain, in which the number of carbon atoms is preferably 2 to 20, more preferably 2 to 10, and includes vinyl, 1-propenyl, 2-propenyl, 1-butenyl, 2-butenyl, 3-butenyl, 2-methylbut-2-enyl, etc. "(C2-C30)alkynyl" is meant to be a linear or branched alkynyl having 2 to 30 carbon atoms constituting the chain, in which the number of carbon atoms is preferably 2 to 20, more preferably 2 to 10, and includes ethynyl, 1-propynyl, 2-propynyl, 1-butynyl, 2-butynyl, 3-butynyl, 1-methylpent-2-ynyl, etc. "(C3-C30)cycloalkyl" is meant to be a mono- or polycyclic hydrocarbon having 3 to 30 ring backbone carbon atoms, in which the number of carbon atoms is preferably 3 to 20, more preferably 3 to 7, and includes cyclopropyl, cyclobutyl, cyclopentyl, cyclohexyl, etc. "(3- to 7-membered)heterocycloalkyl" is meant to be a cycloalkyl having at least one heteroatom selected from the group consisting of B, N, O, S, Si, and P, preferably selected from the group consisting of O, S, and N, and 3 to 7 ring backbone atoms, preferably 5 to 7 ring backbone atoms, and includes tetrahydrofuran, pyrrolidine, thiolan, tetrahydropyran, etc. "(C6-C30)aryl(ene)" is meant to be a monocyclic or fused ring radical derived from an aromatic hydrocarbon having 6 to 30 ring backbone carbon atoms and may be partially saturated, in which the number of ring backbone carbon atoms is preferably 6 to 25, more preferably 6 to 18, may include a spiro structure, and includes phenyl, biphenyl, terphenyl, naphthyl, binaphthyl, phenylnaphthyl, naphthylphenyl, phenylterphenyl, fluorenyl, phenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl, spirobifluorenyl, etc. "(5- to 30-membered)heteroaryl(ene)" is meant to be an aryl group having at least one, preferably 1 to 4 heteroatoms selected from the group consisting of B, N, O, S, Si, and P, and 5 to 30 ring backbone atoms; is a monocyclic ring, or a fused ring condensed with at least one benzene ring; may be partially saturated; may be one formed by linking at least one heteroaryl or aryl group to a heteroaryl group via a single bond(s); may include a spiro structure; and includes a monocyclic ring-type heteroaryl including furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., and a fused ring-type heteroaryl including benzofuranyl, benzothiophenyl, isobenzofuranyl, dibenzofuranyl, dibenzothiophenyl, benzimidazolyl, benzothiazolyl, benzoisothiazolyl, benzoisoxazolyl, benzoxazolyl, isoindolyl, indolyl, benzoindolyl, indazolyl, benzothiadiazolyl, quinolyl, isoquinolyl, cinnolinyl, quinazolinyl, benzoquinazolinyl, quinoxalinyl, benzoquinoxalinyl, naphthyridinyl, carbazolyl, benzocarbazolyl, dibenzocarbazolyl, phenoxazinyl, phenothiazinyl, phenanthridinyl, benzodioxolyl, dihydroacridinyl, etc. "Halogen" includes F, Cl, Br, and I.

Herein, "substituted" in the expression "substituted or unsubstituted" means that a hydrogen atom in a certain functional group is replaced with another atom or functional group, i.e., a substituent. The substituents of the substituted alkyl, the substituted aryl(ene), the substituted heteroaryl (ene), the substituted heterocycloalkyl, the substituted cycloalkyl, and the substituted mono- or polycyclic, alicyclic or aromatic ring, or a combination thereof in R, $R_1$, $R_2$, $R_{11}$, and L, each independently, are at least one selected from the group consisting of deuterium; a halogen; a cyano; a carboxyl; a nitro; a hydroxyl; a (C1-C30)alkyl; a halo(C1-C30)alkyl; a (C2-C30)alkenyl; a (C2-C30)alkynyl; a (C1-C30)alkoxy; a (C1-C30)alkylthio; a (C3-C30)cycloalkyl; a (C3-C30)cycloalkenyl; a (3- to 7-membered)heterocycloalkyl; a (C6-C30)aryloxy; a (C6-C30)arylthio; a (5- to 30-membered)heteroaryl unsubstituted or substituted with a (C6-C30)aryl(s); a (C6-C30)aryl unsubstituted or substituted with a (5- to 30-membered)heteroaryl(s); a tri(C1-C30)alkylsilyl; a tri(C6-C30)arylsilyl; a di(C1-C30)alkyl(C6-C30)arylsilyl; a (C1-C30)alkyldi(C6-C30)arylsilyl; an amino; a mono- or di-(C1-C30)alkylamino; a mono- or di-(C6-C30)arylamino unsubstituted or substituted with a (C1-C30)alkyl(s); a (C1-C30)alkyl(C6-C30)arylamino; a (C1-C30)alkylcarbonyl; a (C1-C30)alkoxycarbonyl; a (C6-C30)arylcarbonyl; a di(C6-C30)arylboronyl; a di(C1-C30)alkylboronyl; a (C1-C30)alkyl(C6-C30)arylboronyl; a (C6-C30)aryl(C1-C30)alkyl; and a (C1-C30)alkyl(C6-C30)aryl, preferably, each independently, represent a (C1-C6)alkyl, a (C6-C18)aryl, or a (5- to 15-membered)heteroaryl, and for example, methyl, phenyl, fluoranthenyl, triphenylenyl, pyridyl, etc.

The compound represented by formula 1 includes the following compounds, but is not limited thereto:

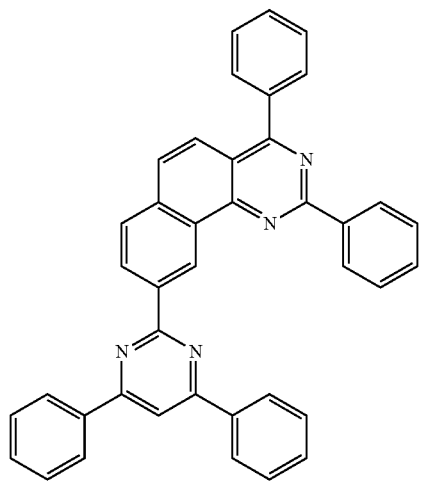

C-1

C-2

-continued
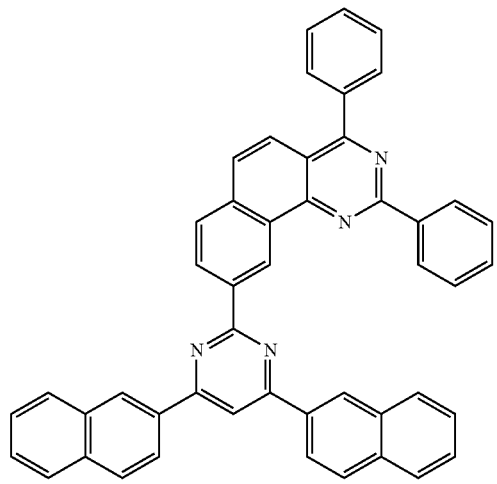
C-3
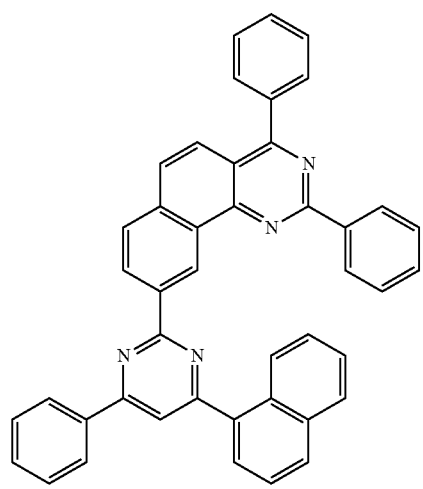
C-4
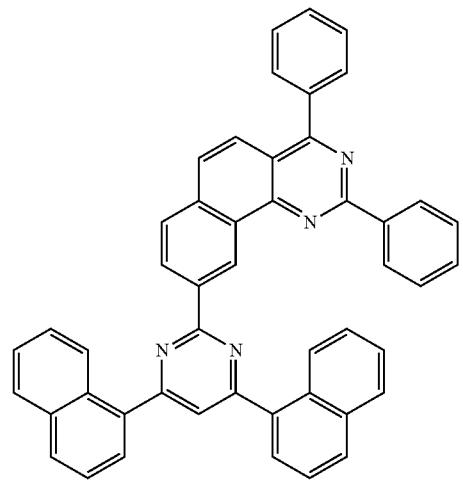
C-5
-continued
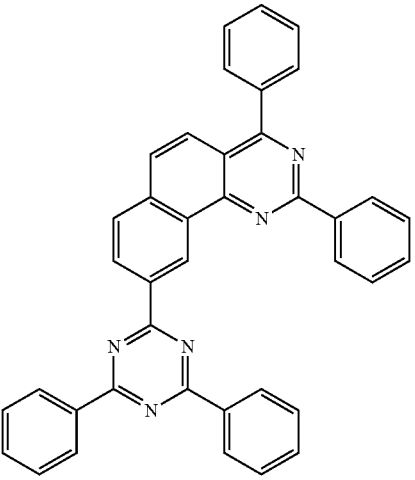
C-6
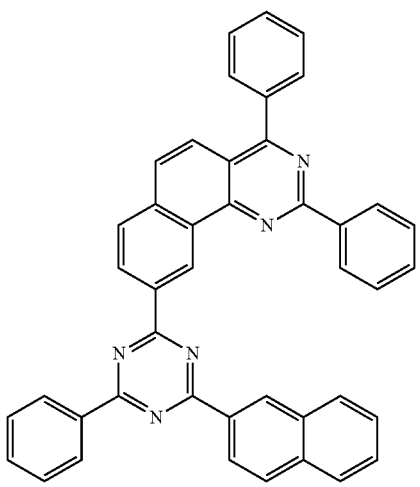
C-7
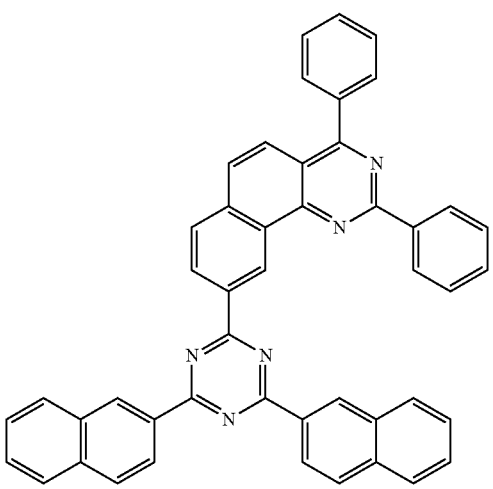
C-8

C-9
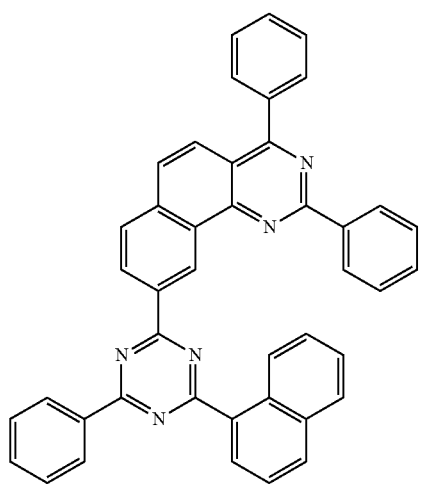
C-10
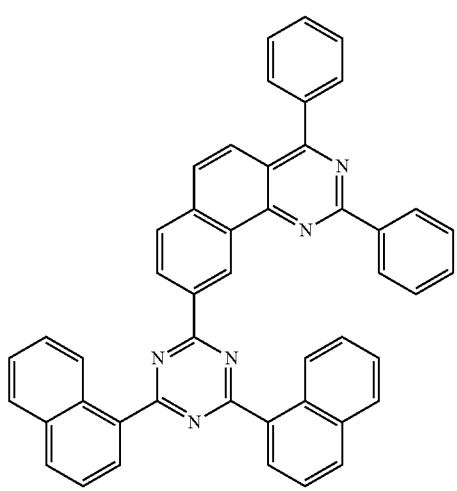
C-11
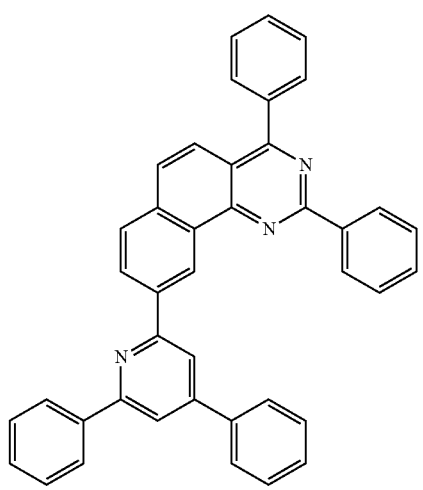
C-12
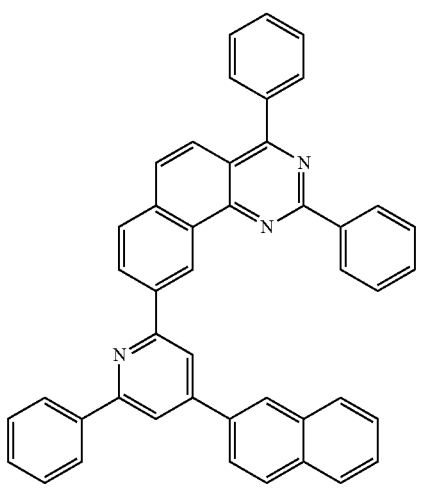
C-13
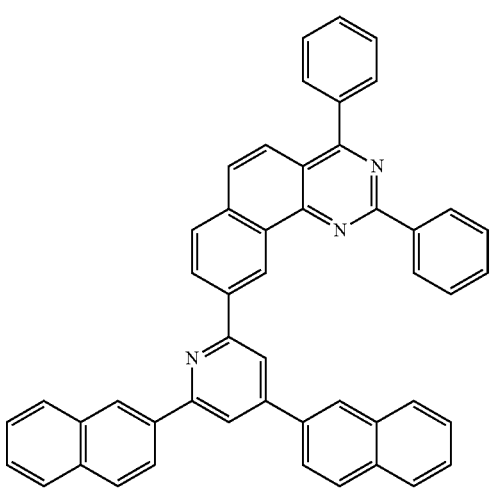
C-14
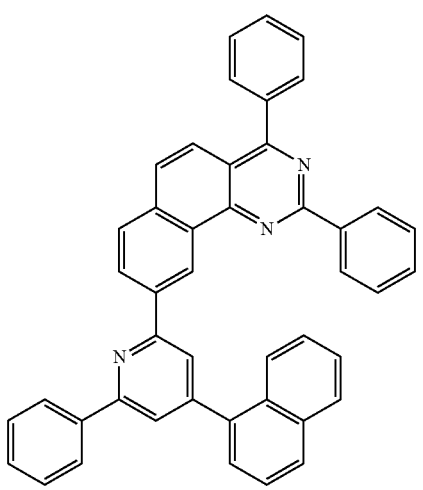

C-15
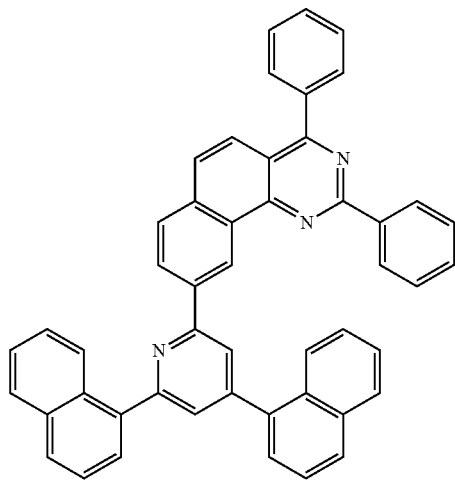
C-16
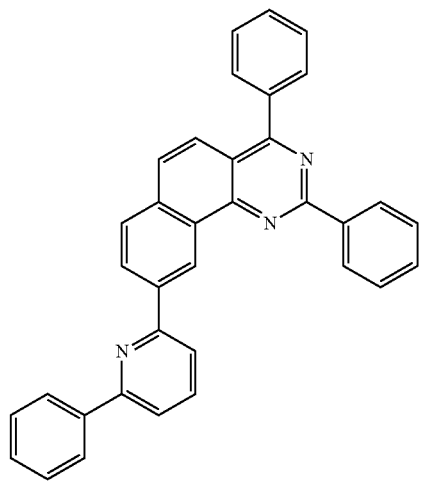
C-17
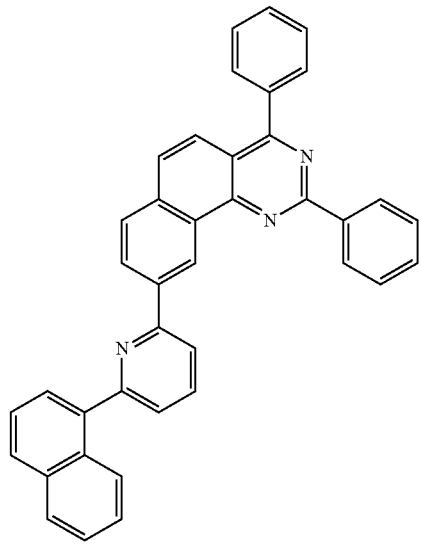
C-18
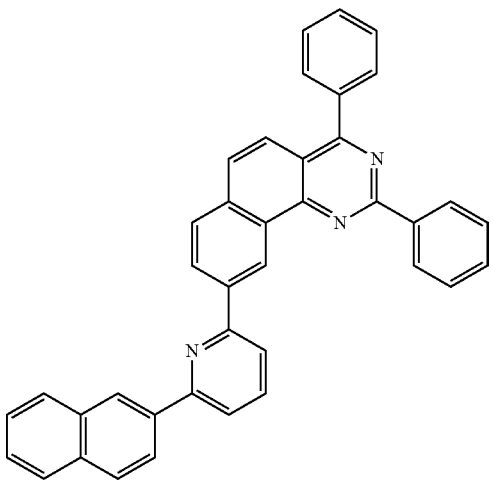
C-19
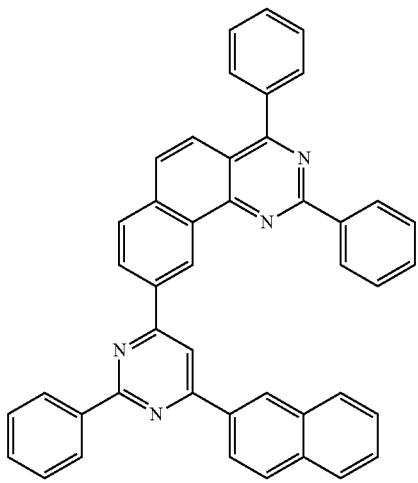
C-20
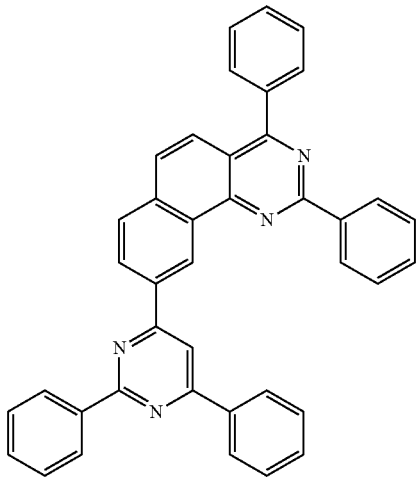

C-21
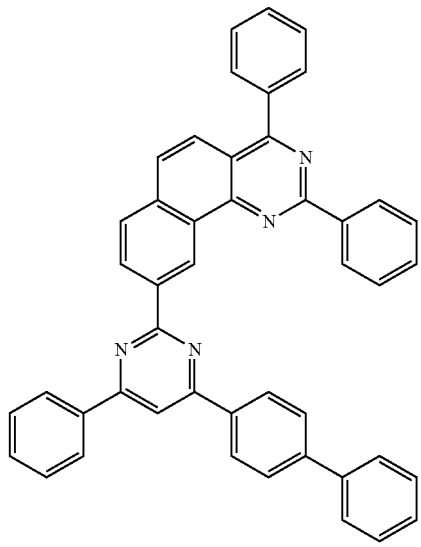
C-22
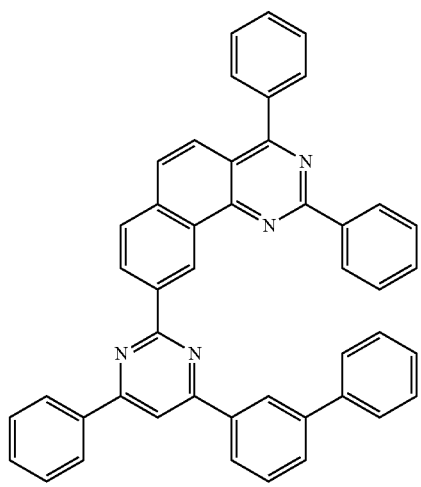
C-23
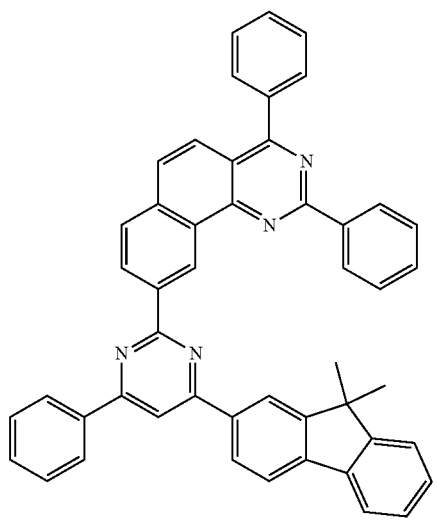
C-24
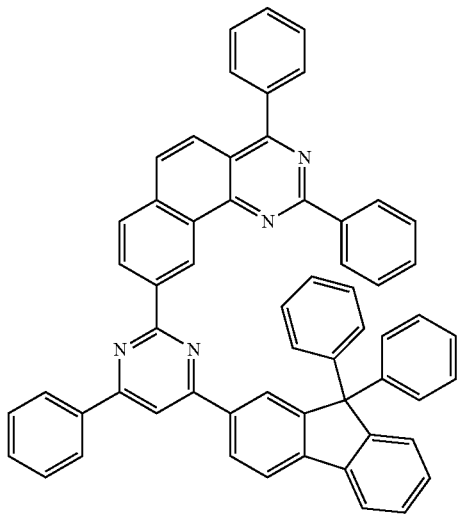
C-25
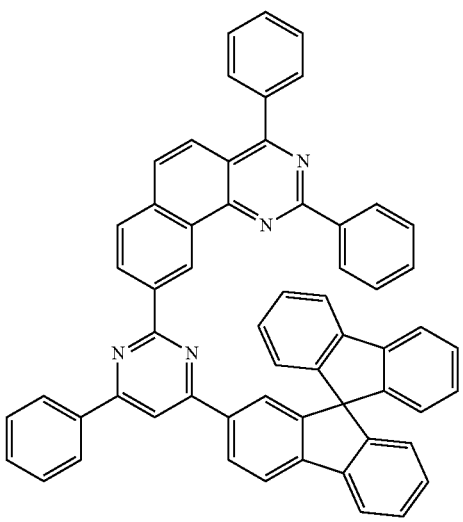
C-26
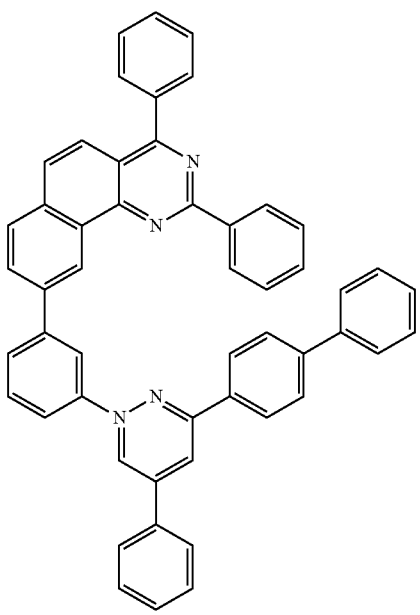

C-27
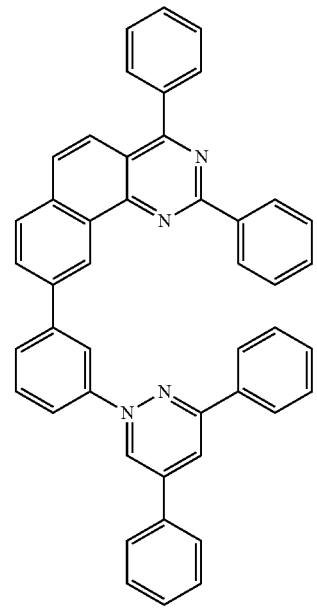
C-28
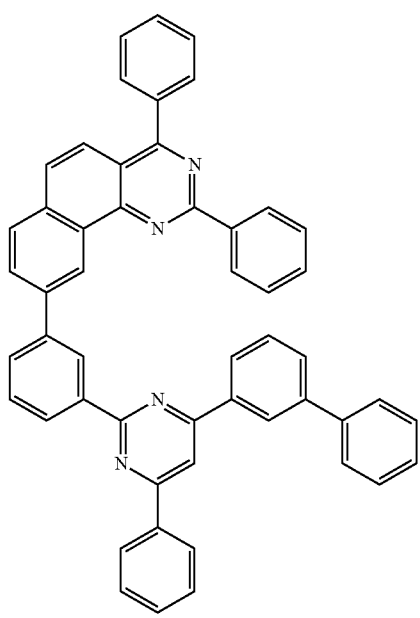
C-29
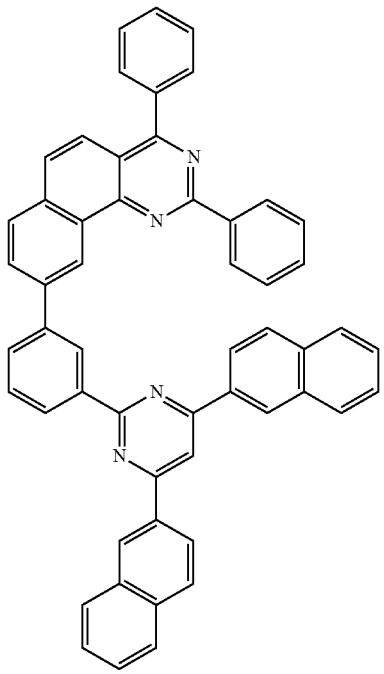
C-30
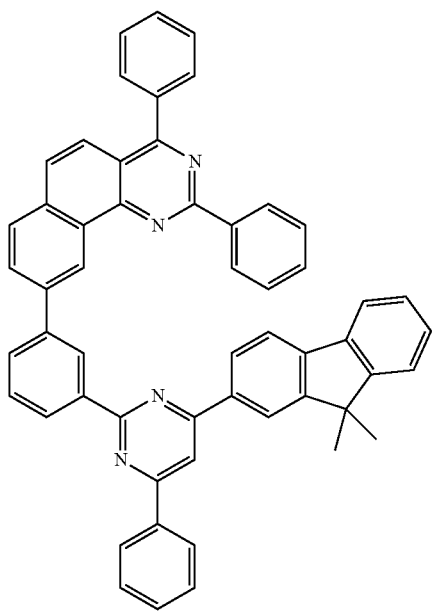

C-31
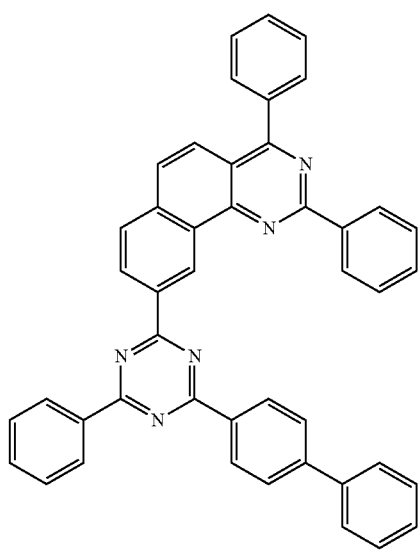
C-32
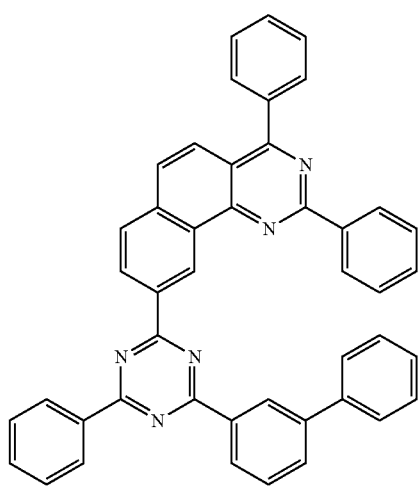
C-33
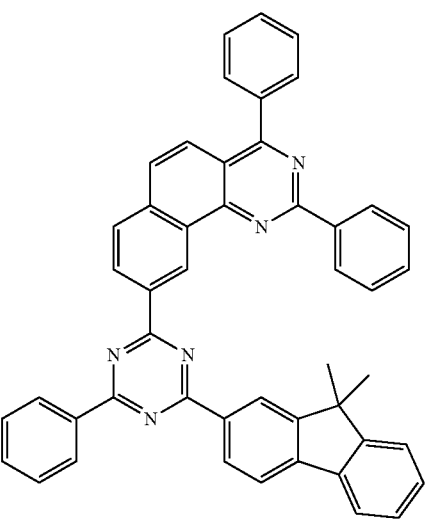
C-34
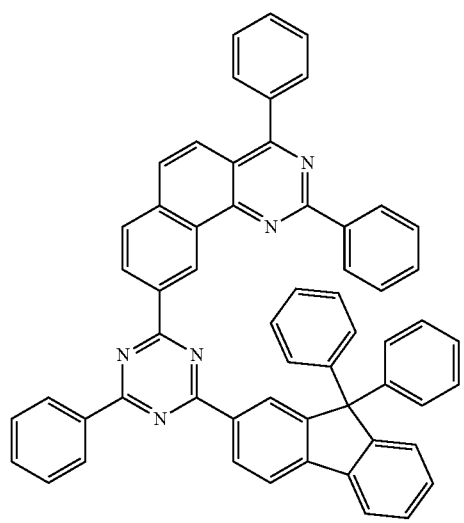
C-35
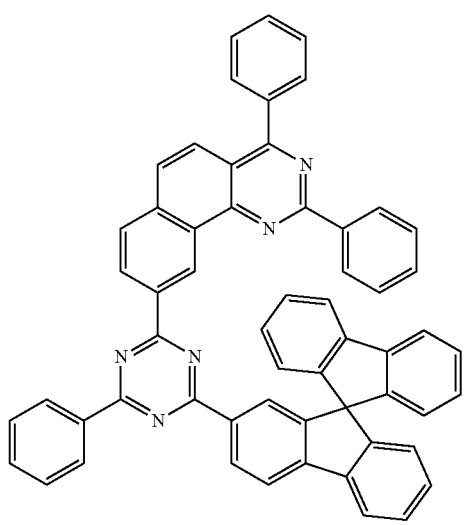
C-36
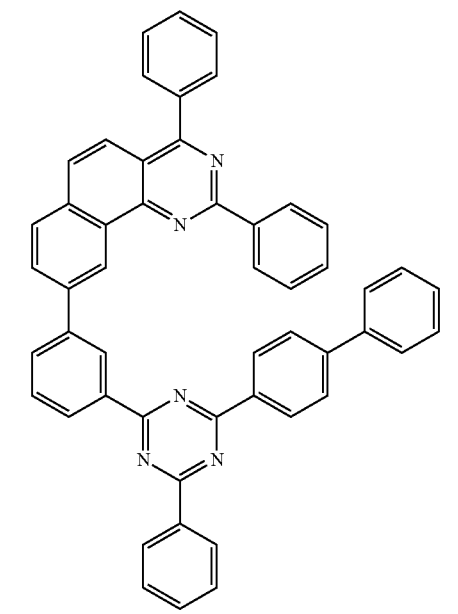

C-37
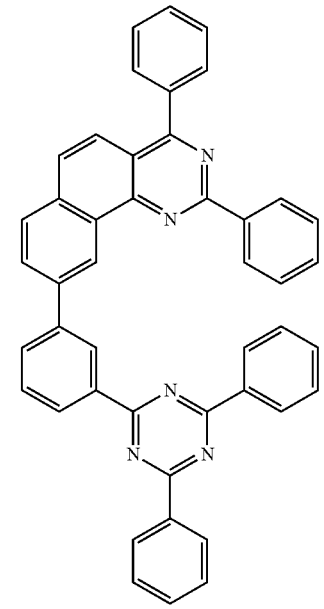
C-38
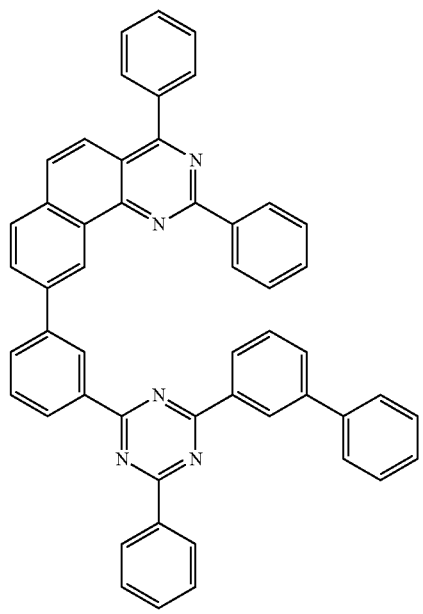
C-39
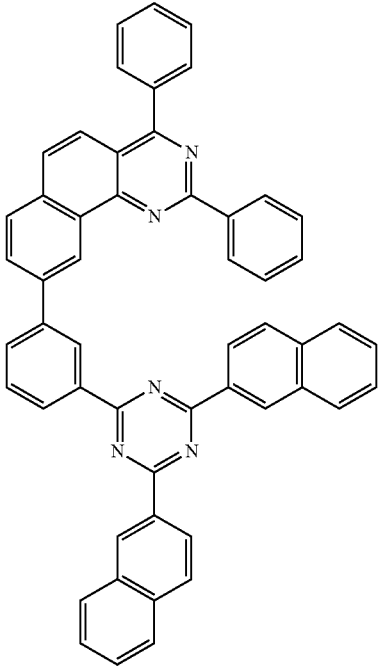
C-40
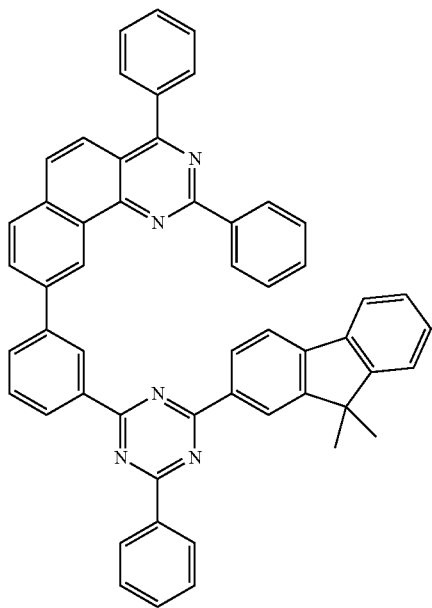

C-41
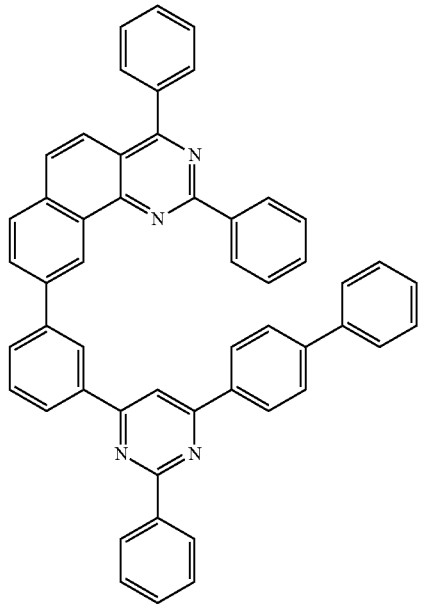
C-42
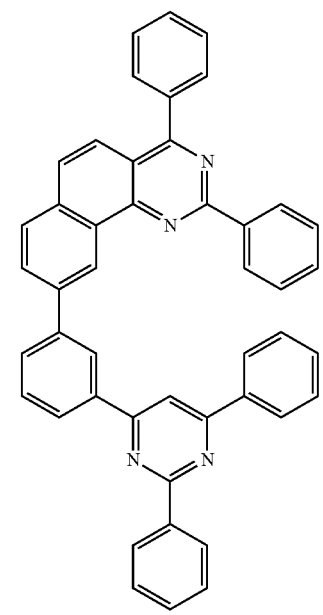
C-43
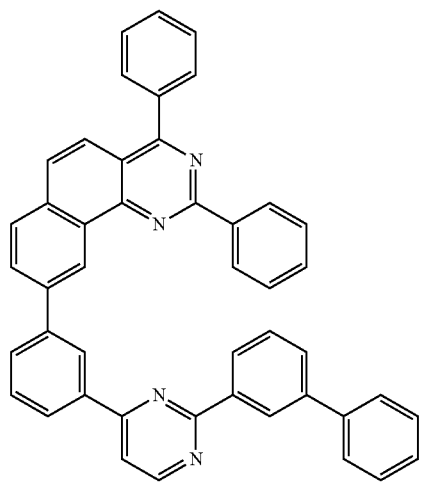
C-44
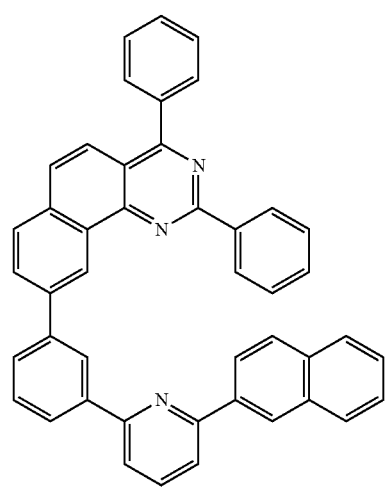
C-45
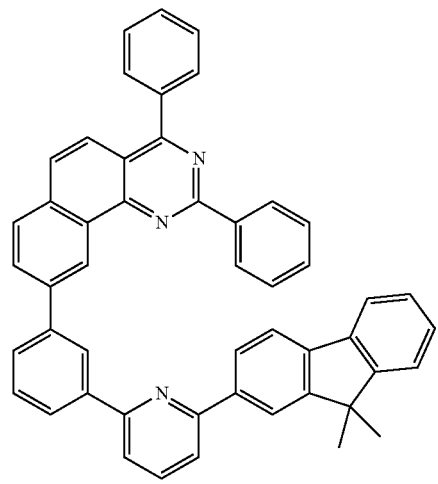

C-46
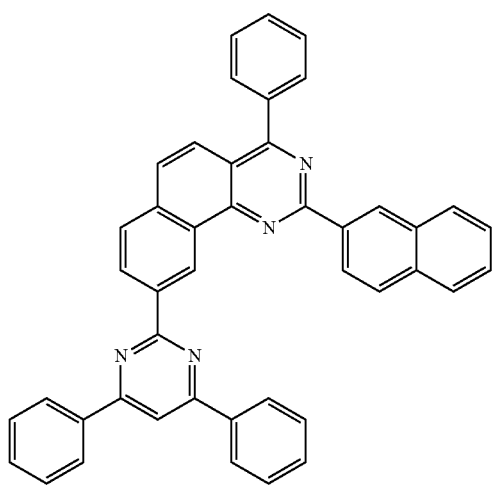
C-47
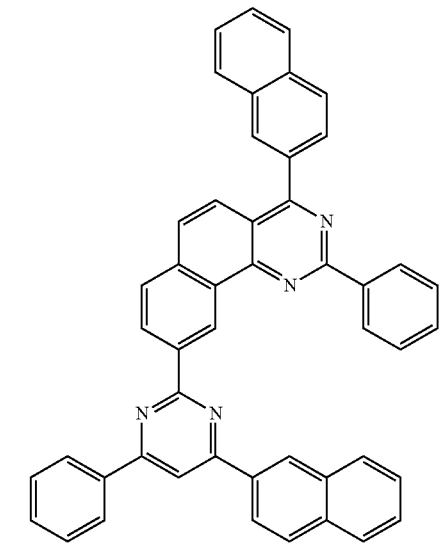
C-48
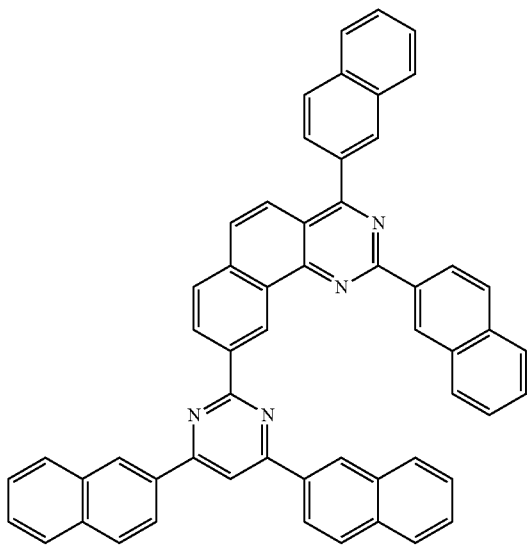
C-49
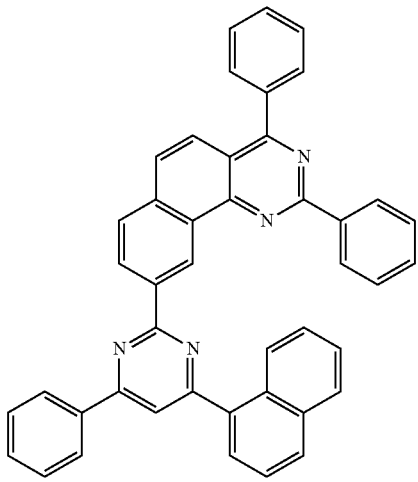
C-50
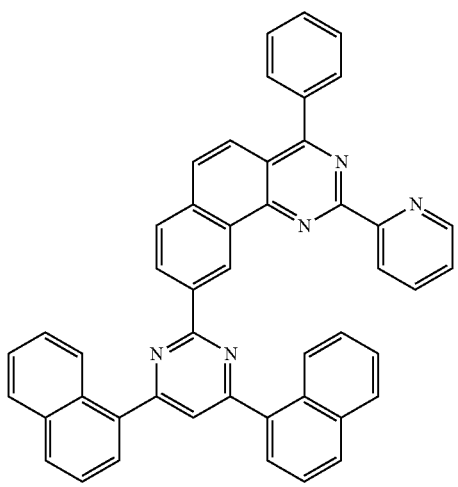
C-51
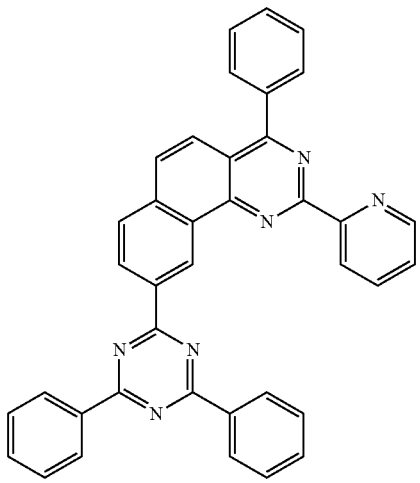

C-52 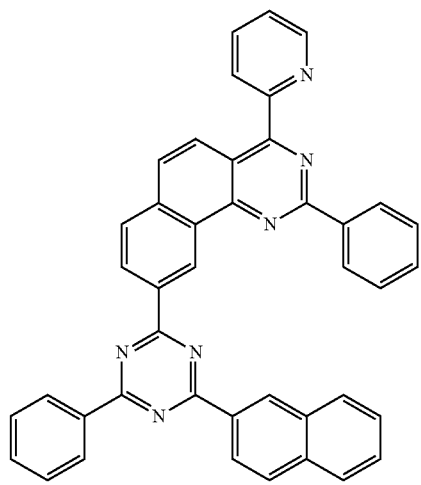
C-53 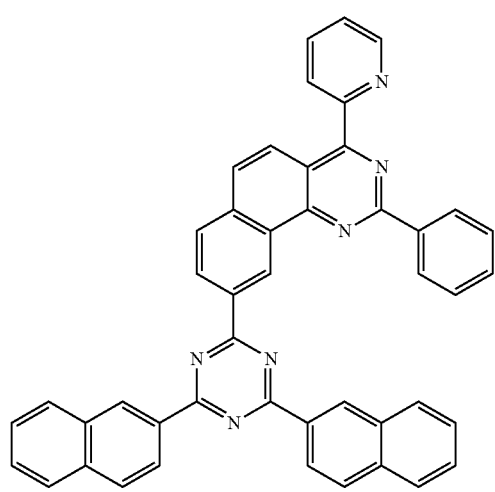
C-54 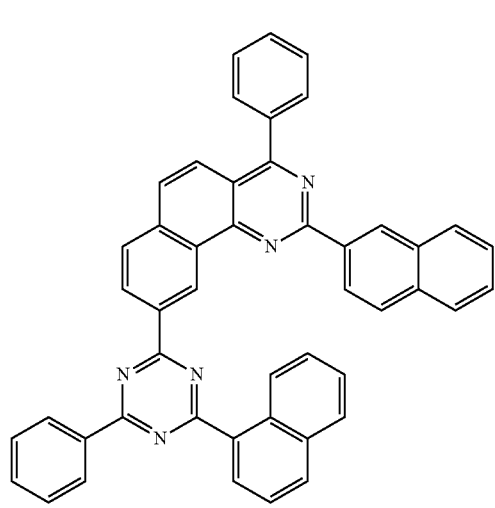
C-55 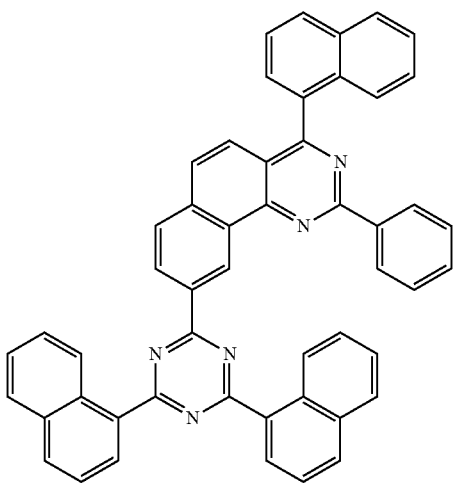
C-56 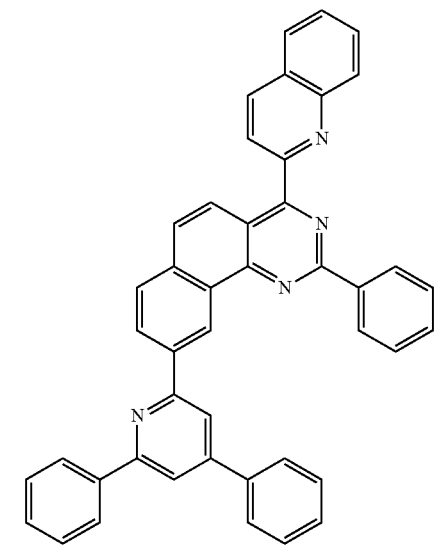
C-57

C-58
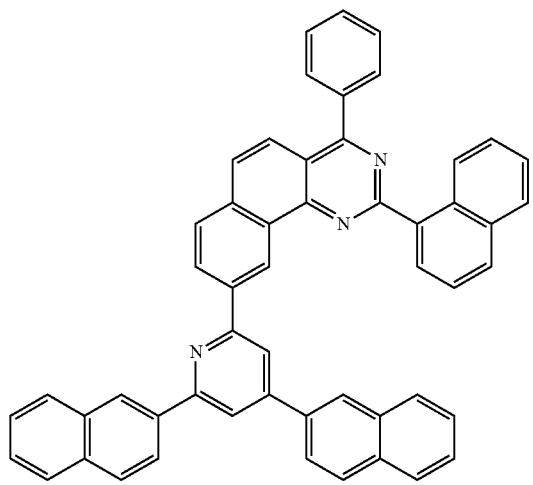
C-59
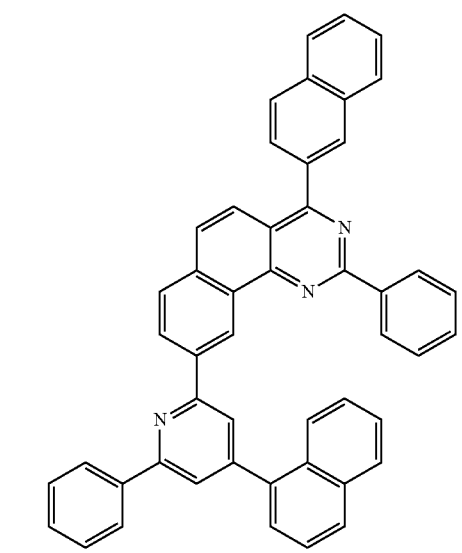
C-60
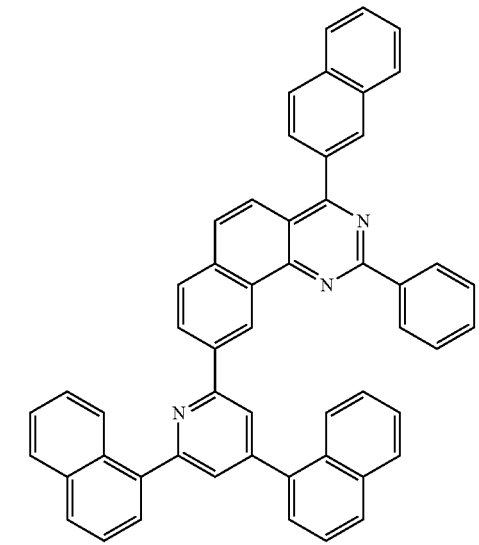
C-61
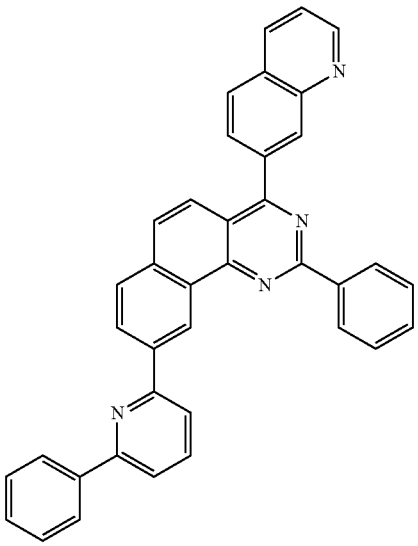
C-62
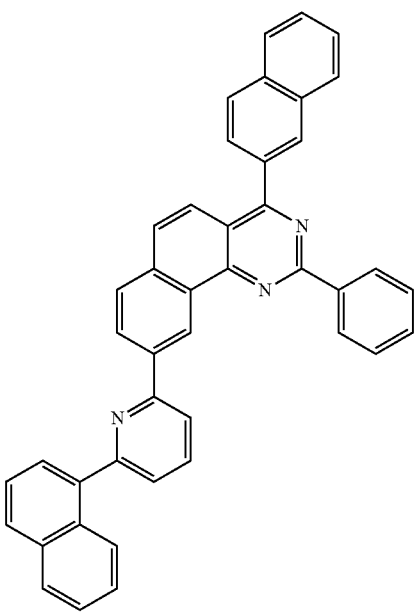
C-63
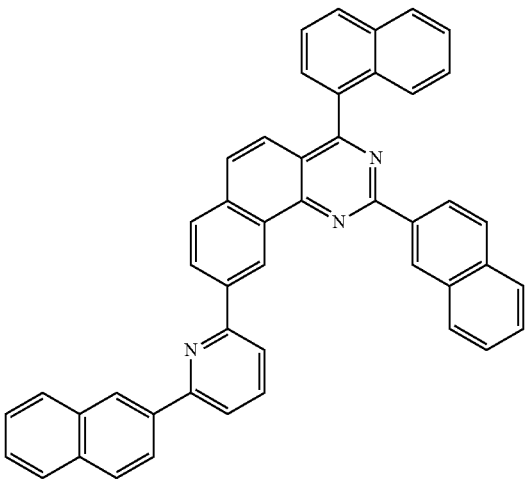

C-64
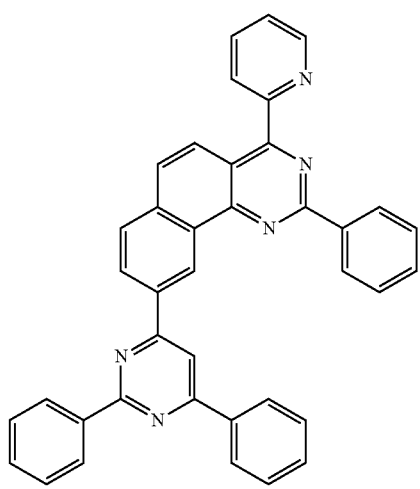
C-65
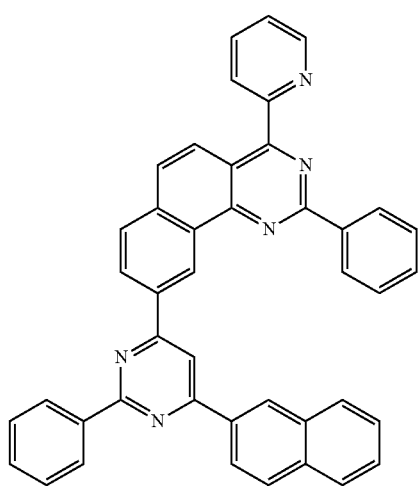
C-66
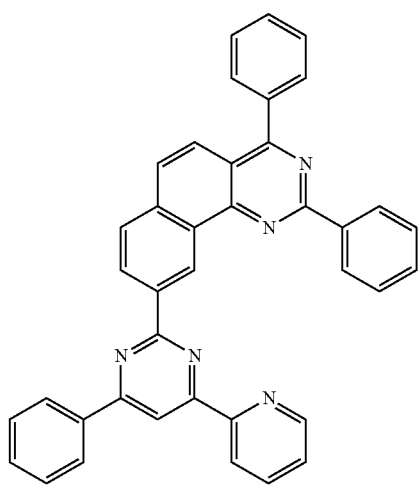
C-67
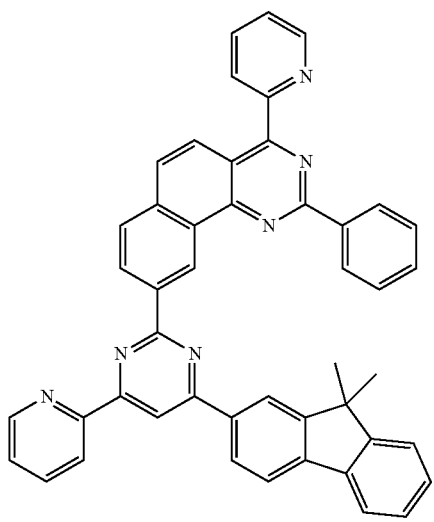
C-68
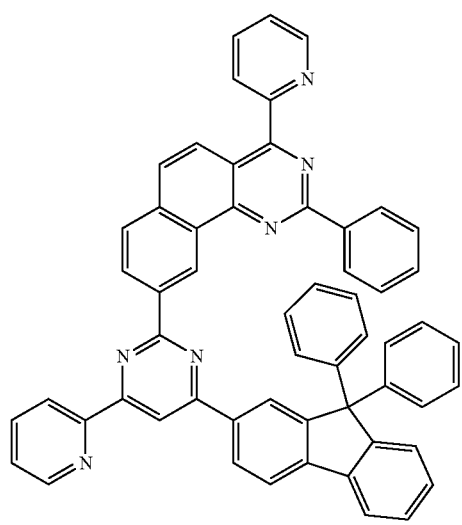
C-69
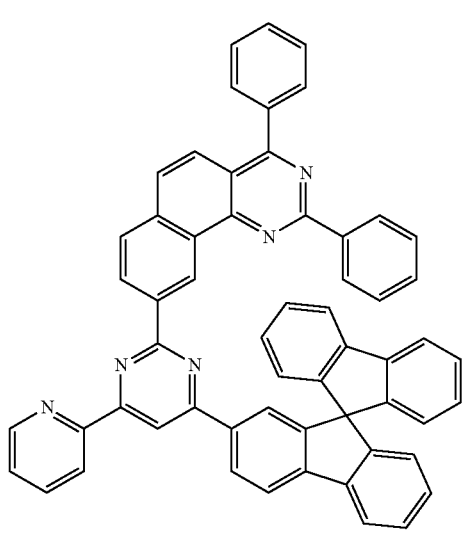

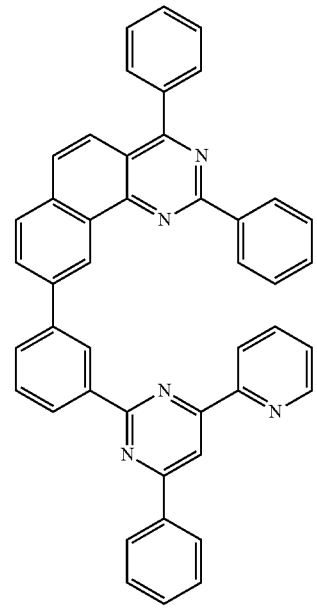
C-70
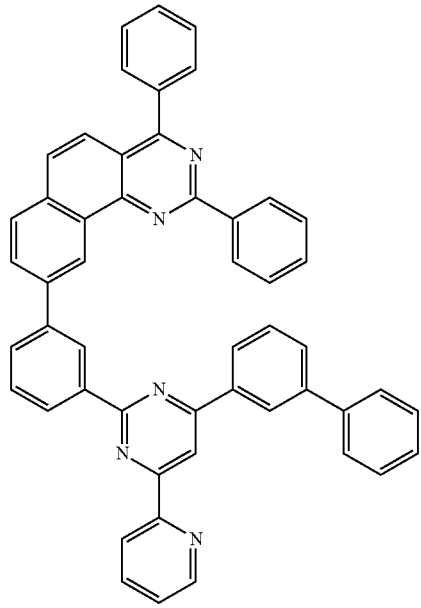
C-72
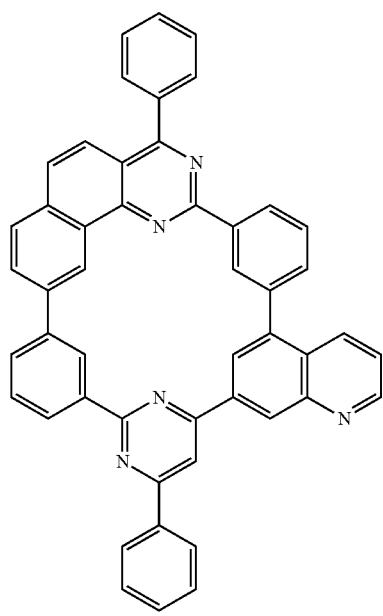
C-71
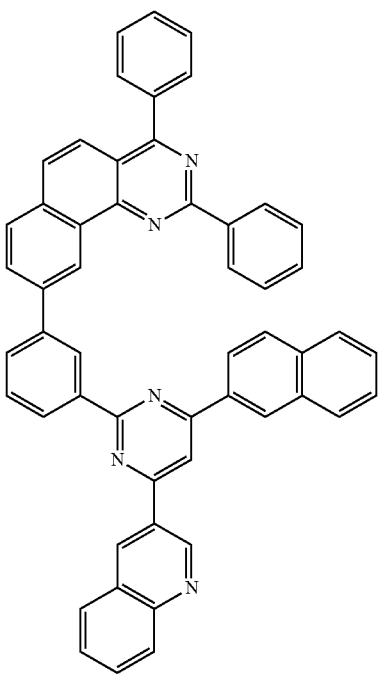
C-73

C-74
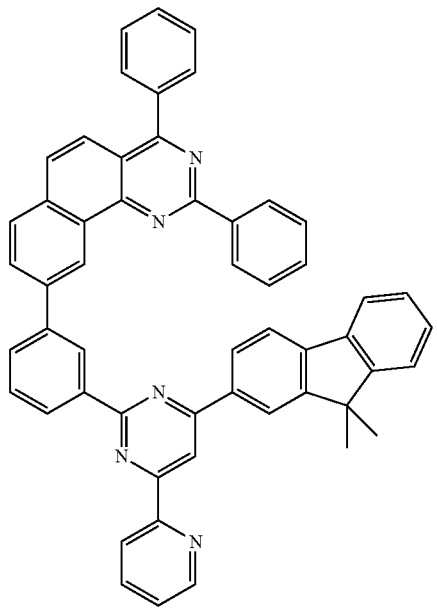
C-75
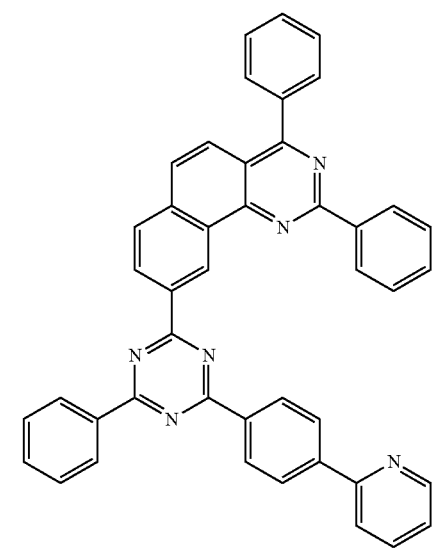
C-76
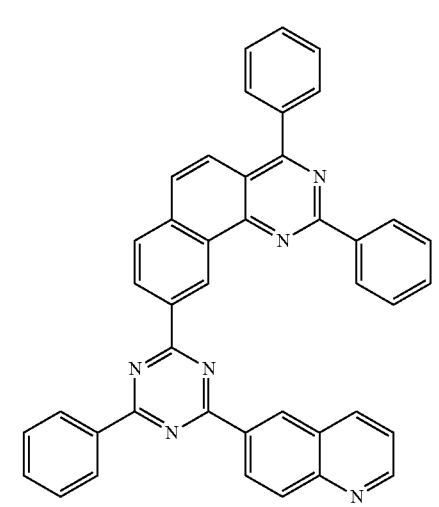
C-77
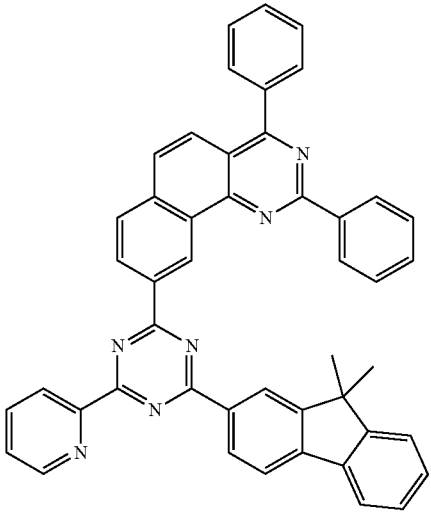
C-78
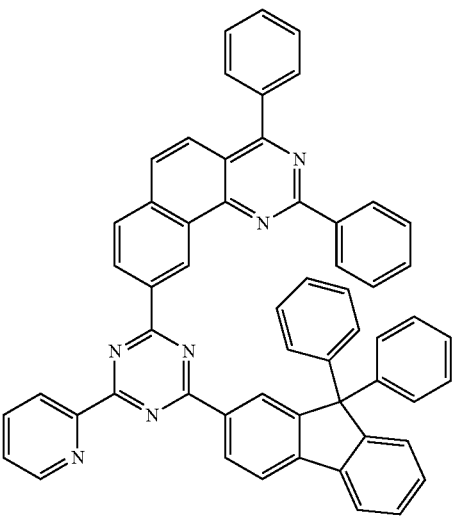
C-79
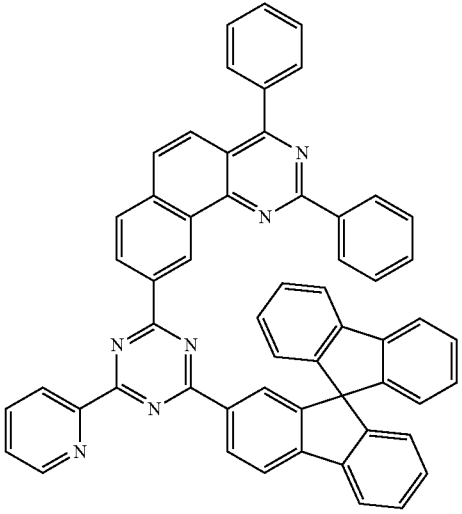

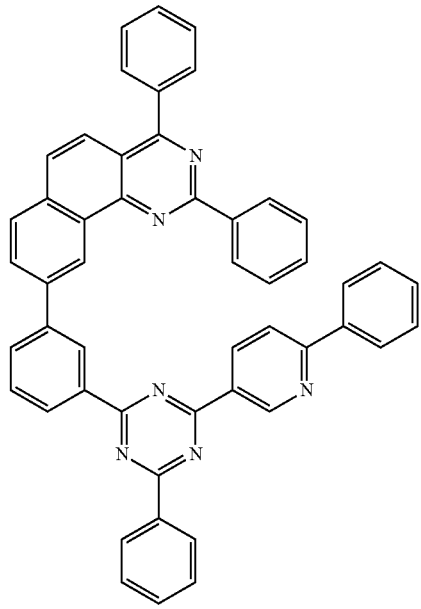
C-80
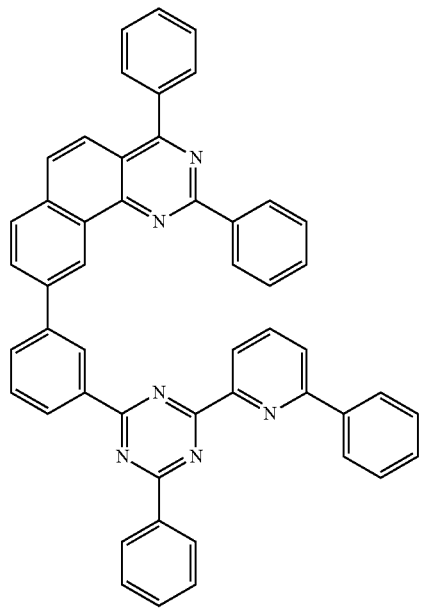
C-82
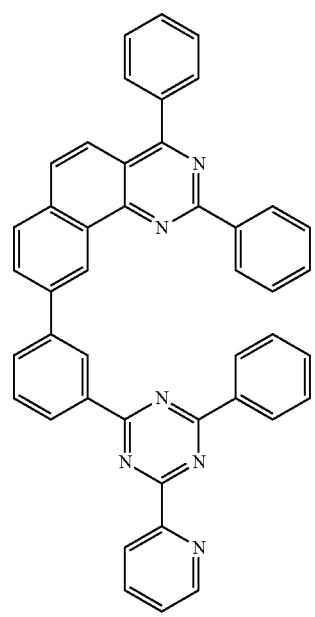
C-81
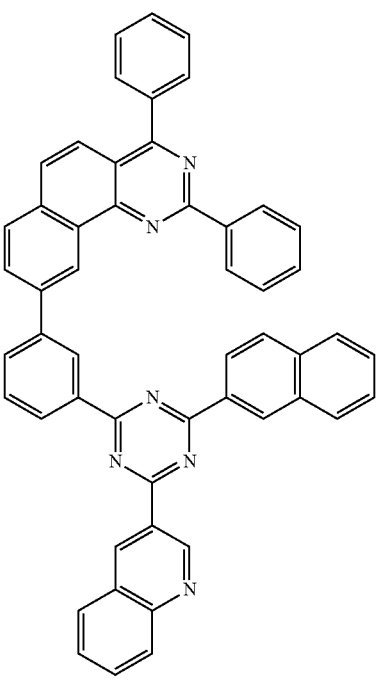
C-83

C-84
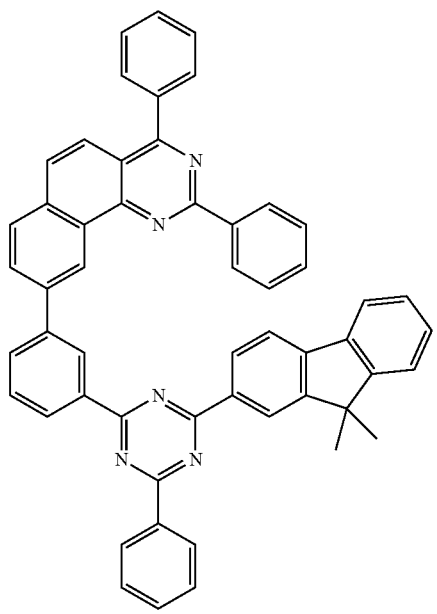
C-85
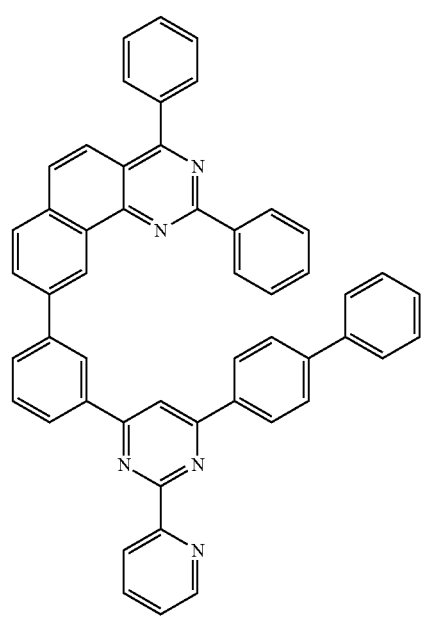
C-86
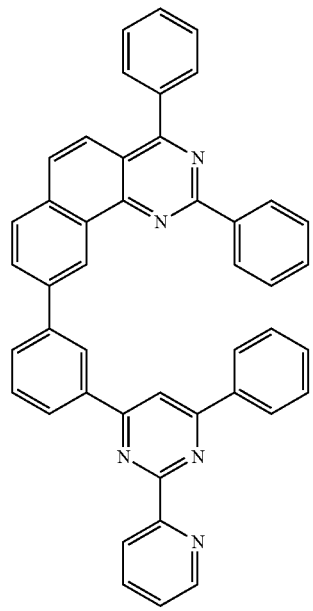
C-87
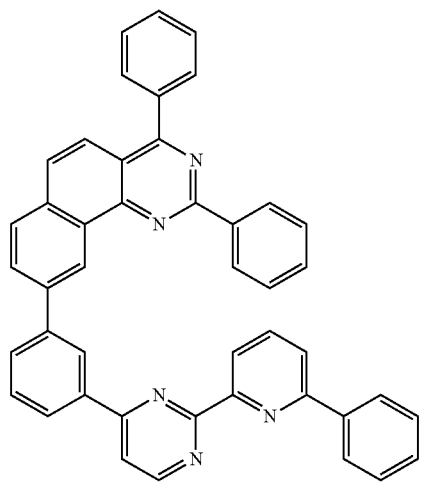
C-88
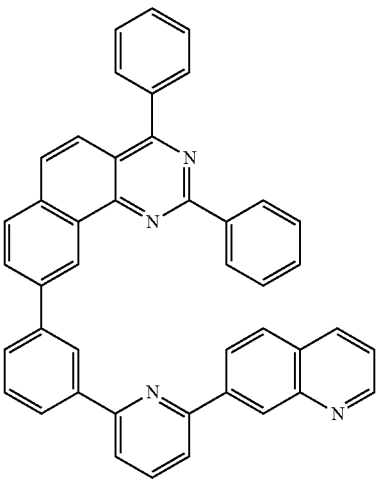

C-89
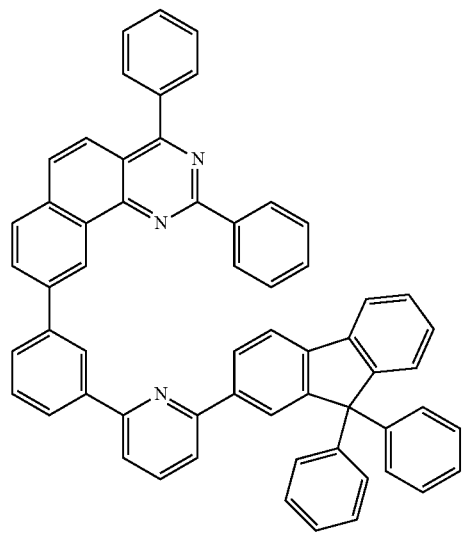
C-90
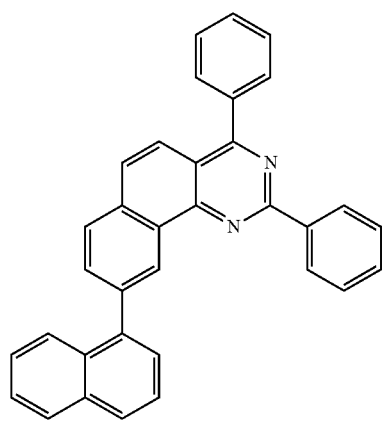
C-91
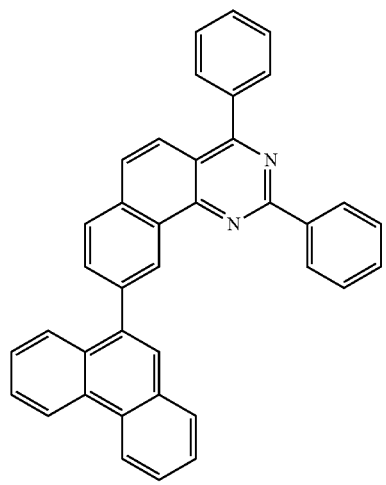
C-92
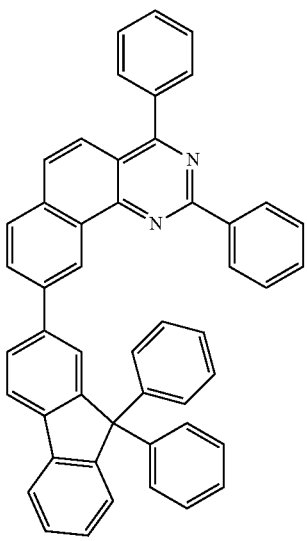
C-93
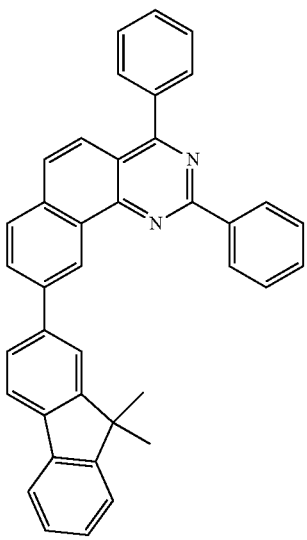
C-94
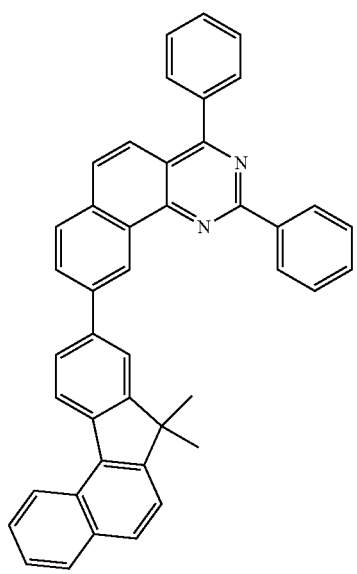

C-95
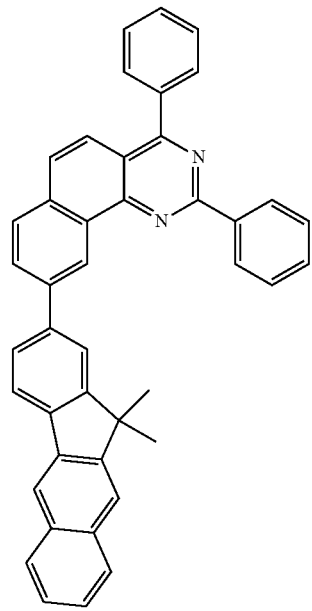
C-96
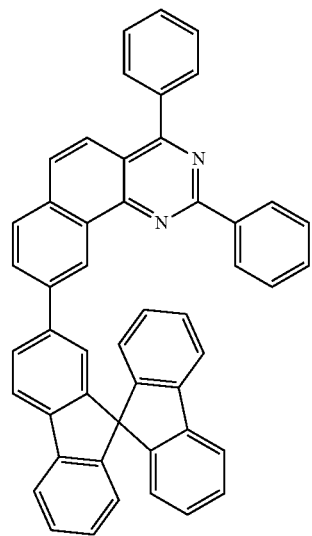
C-97
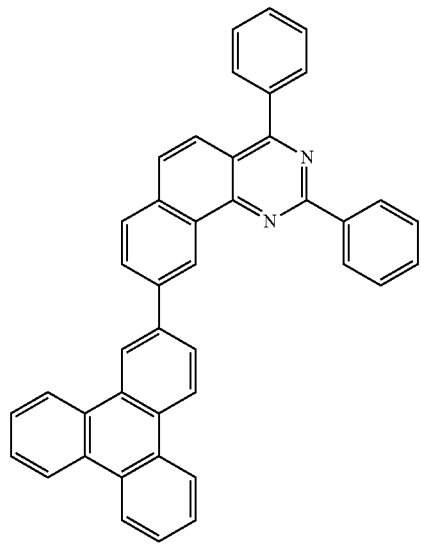
C-98
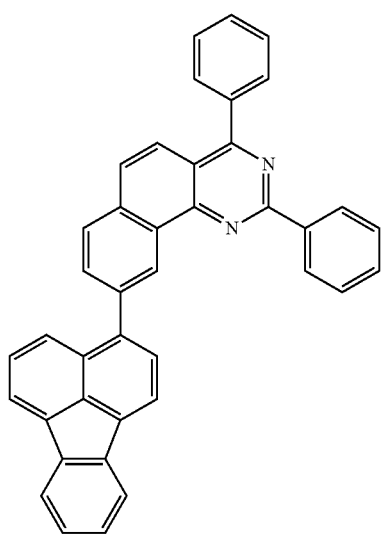
C-99
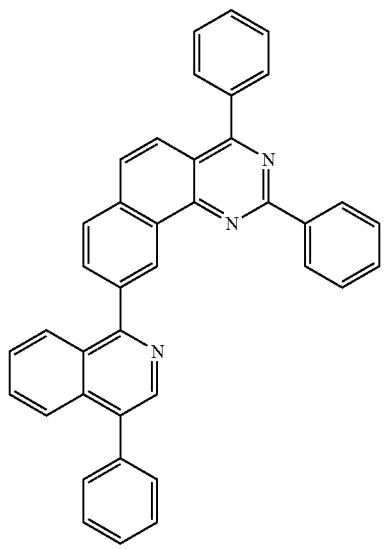

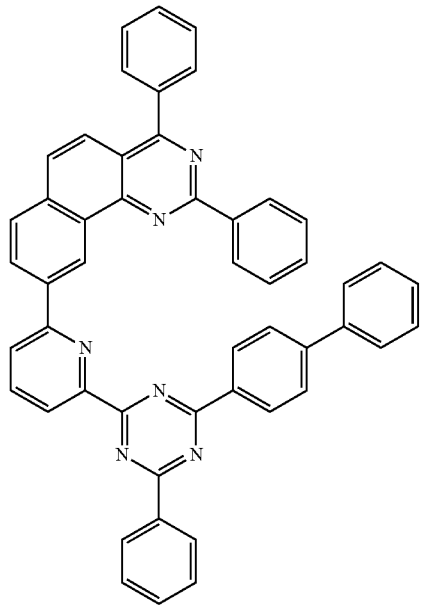
C-100
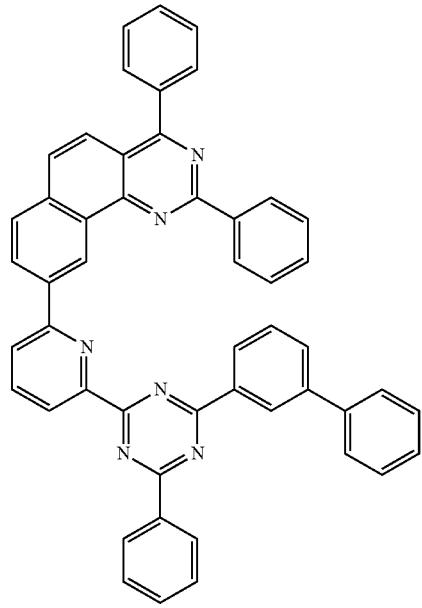
C-102
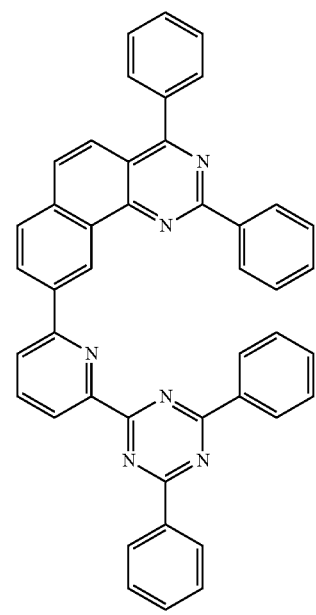
C-101
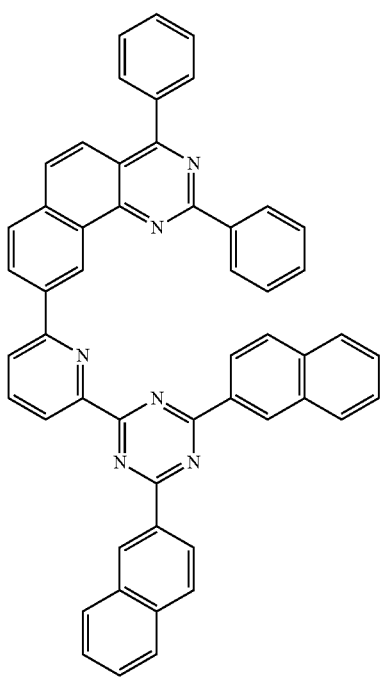
C-103

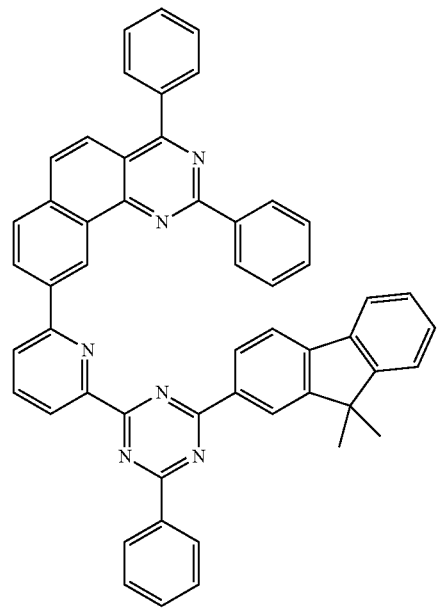
C-104
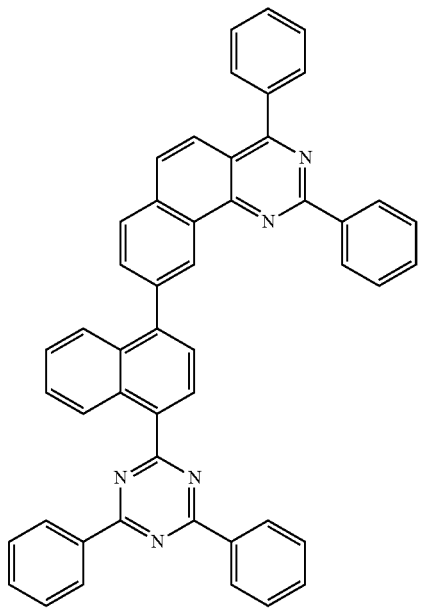
C-106
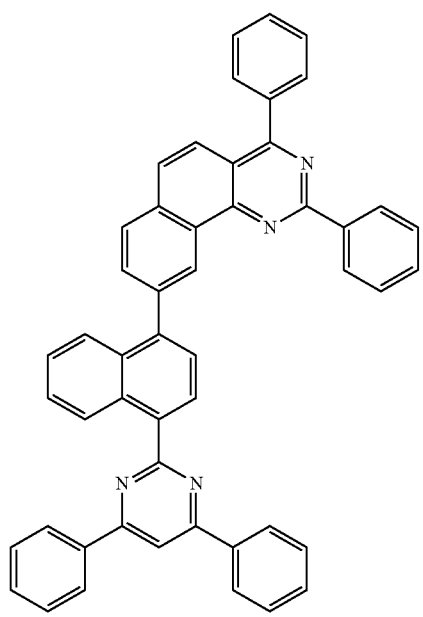
C-105
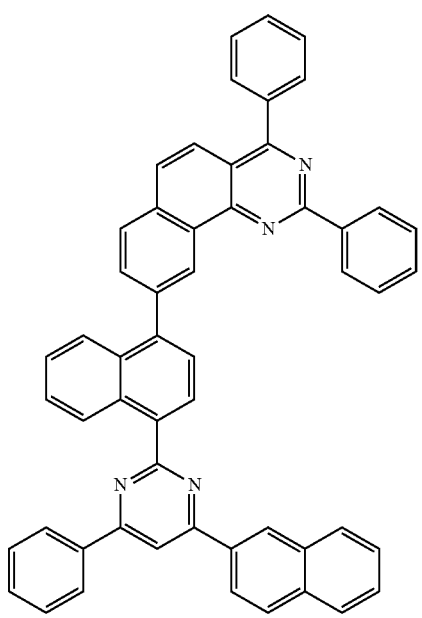
C-107

C-108
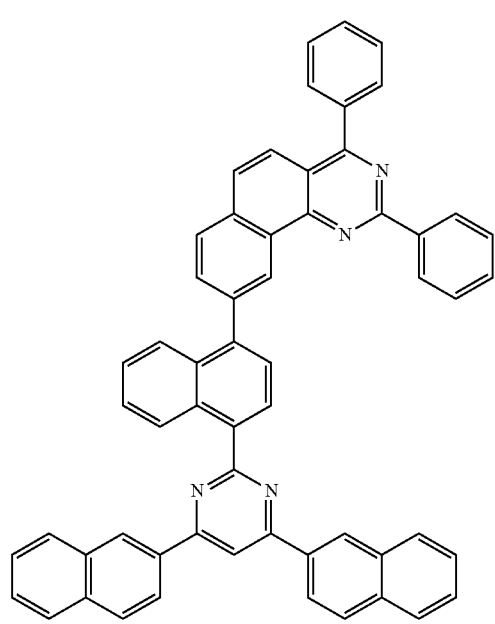
C-109
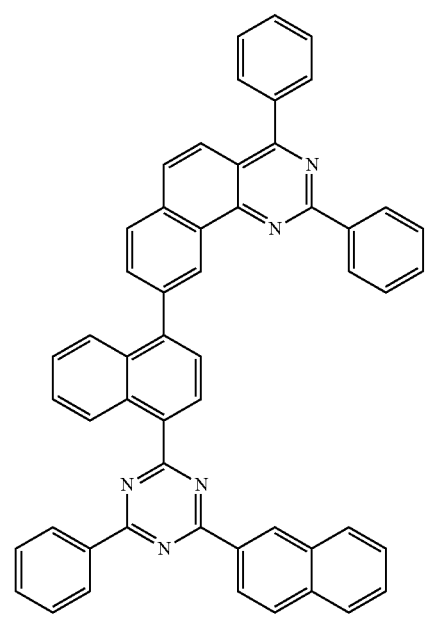
C-110
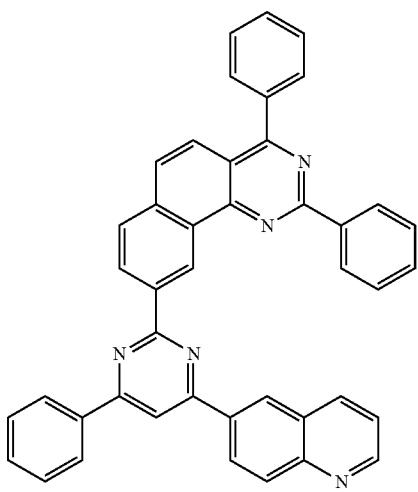
C-111

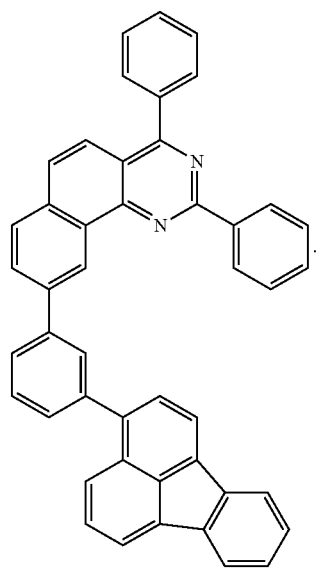
C-112
The compound represented by formula 1 according to the present disclosure can be prepared by a synthetic method known to a person skilled in the art, for example, according to the following reaction schemes, but is not limited thereto.
[Reaction Scheme 1]
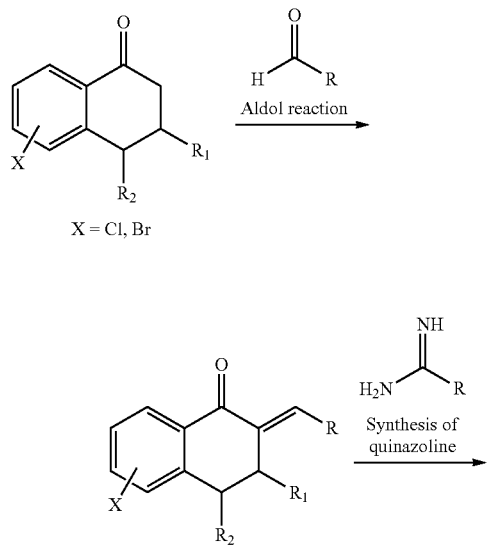
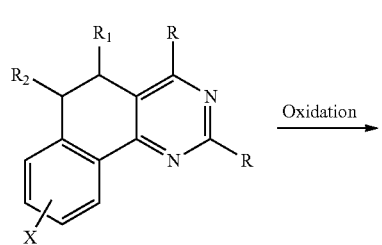
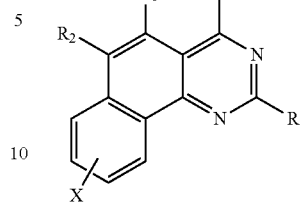
Miyaura borylation
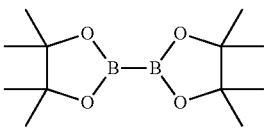
X = Cl, Br
Suzuki cross coupling
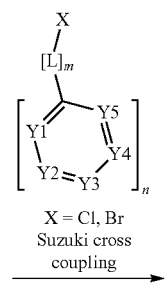
[Reaction Scheme 2]
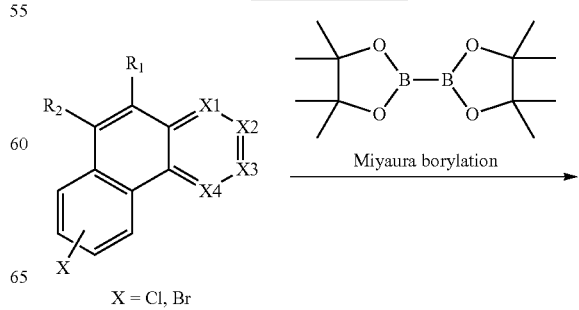
X = Cl, Br
Miyaura borylation

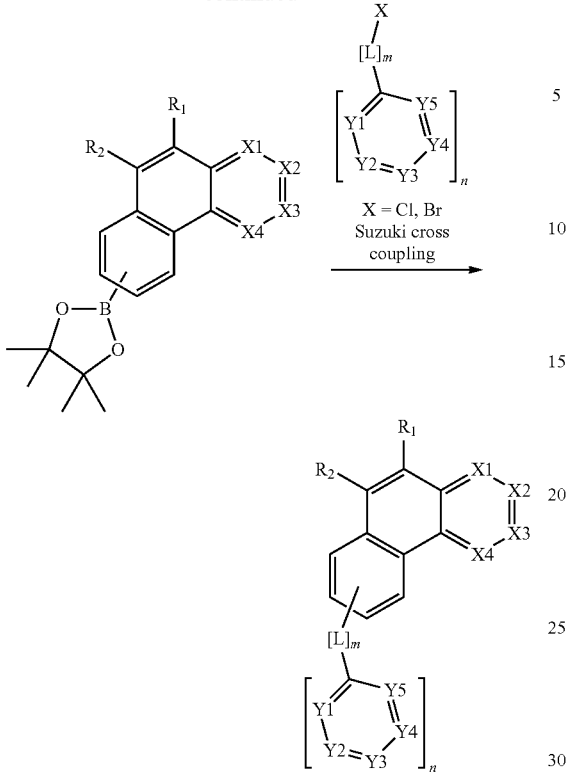

In reaction schemes 1 and 2, $X_1$ to $X_4$, $Y_1$ to $Y_5$, R, $R_1$, $R_2$, L, m, and n are as defined in formula 1.

The present disclosure provides an organic electroluminescent material comprising the organic electroluminescent compound of formula 1, and an organic electroluminescent device comprising the material.

The above material can be comprised of the organic electroluminescent compound of the present disclosure alone, or can further include conventional materials generally used in organic electroluminescent materials.

The organic electroluminescent device according to the present disclosure comprises a first electrode; a second electrode; and at least one organic layer between the first and second electrodes. The organic layer may comprise at least one organic electroluminescent compound of formula 1.

One of the first and second electrodes may be an anode, and the other may be a cathode. The organic layer may comprise a light-emitting layer, and may further comprise at least one layer selected from a hole injection layer, a hole transport layer, a hole auxiliary layer, a light-emitting auxiliary layer, an electron transport layer, an electron buffer layer, an electron injection layer, an interlayer, a hole blocking layer, and an electron blocking layer.

The organic electroluminescent compound of formula 1 of the present disclosure may be comprised in one or more layers of the light-emitting layer, the hole injection layer, the hole transport layer, the hole auxiliary layer, the light-emitting auxiliary layer, the electron transport layer, the electron buffer layer, the electron injection layer, the interlayer, the hole blocking layer, and the electron blocking layer; and preferably in one or more layers of the light-emitting layer, the electron buffer layer, and the electron transport layer. When used in the light-emitting layer, the organic electroluminescent compound of formula 1 of the present disclosure can be comprised as a host material. When used in the electron buffer layer, the organic electroluminescent compound of formula 1 of the present disclosure can be comprised as an electron buffer material. When used in the electron transport layer, the organic electroluminescent compound of formula 1 of the present disclosure can be comprised as an electron transport material.

The light-emitting layer can comprise one or more hosts and one or more dopants. If necessary, the light-emitting layer can comprise a co-host material, i.e., a plurality of host materials of two or more.

The host used in the present disclosure is at least one phosphorescent host compound or at least one fluorescent host compound, and these host compounds are not particularly limited. Specifically, the host compound may be a fluorescent host compound, for example, an anthracene compound represented by the following formula 11:

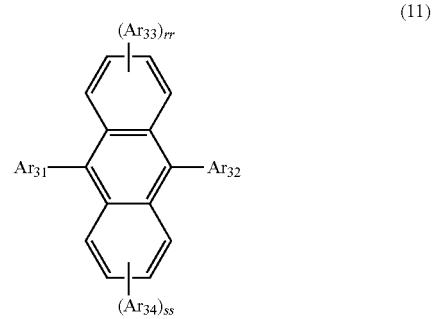

(11)

wherein $Ar_{31}$, and $Ar_{32}$, each independently, represent a substituted or unsubstituted (C6-C30)aryl, or a substituted or unsubstituted (5- to 30-membered)heteroaryl;

$Ar_{33}$ and $Ar_{34}$, each independently, represent hydrogen, deuterium, a halogen, a cyano, a nitro, a hydroxyl, a substituted or unsubstituted (C1-C30)alkyl, a substituted or unsubstituted (C6-C30)aryl, a substituted or unsubstituted (5- to 30-membered)heteroaryl, a substituted or unsubstituted (C3-C30)cycloalkyl, a substituted or unsubstituted (C1-C30)alkoxy, a substituted or unsubstituted (C1-C30) alkylsilyl, a substituted or unsubstituted (C6-C30)arylsilyl, a substituted or unsubstituted (C6-C30)aryl(C1-C30)alkylsilyl, or $NF_{41}R_{42}$;

$R_{41}$ and $R_{42}$, each independently, represent hydrogen, a substituted or unsubstituted (C6-C30)aryl, or a substituted or unsubstituted (5- to 30-membered)heteroaryl; or may be linked to each other to form a mono- or polycyclic, (3- to 30-membered) alicyclic or aromatic ring, or the combination thereof, whose carbon atom(s) may be replaced with at least one heteroatom selected from nitrogen, oxygen, and sulfur; and rr and ss, each independently, represent an integer of 1 to 4, in which if rr or ss represents an integer of 2 or more, each $Ar_{33}$ or each $Ar_{34}$ may be the same or different.

The compound represented by formula 11 includes the following compounds, but is not limited thereto:
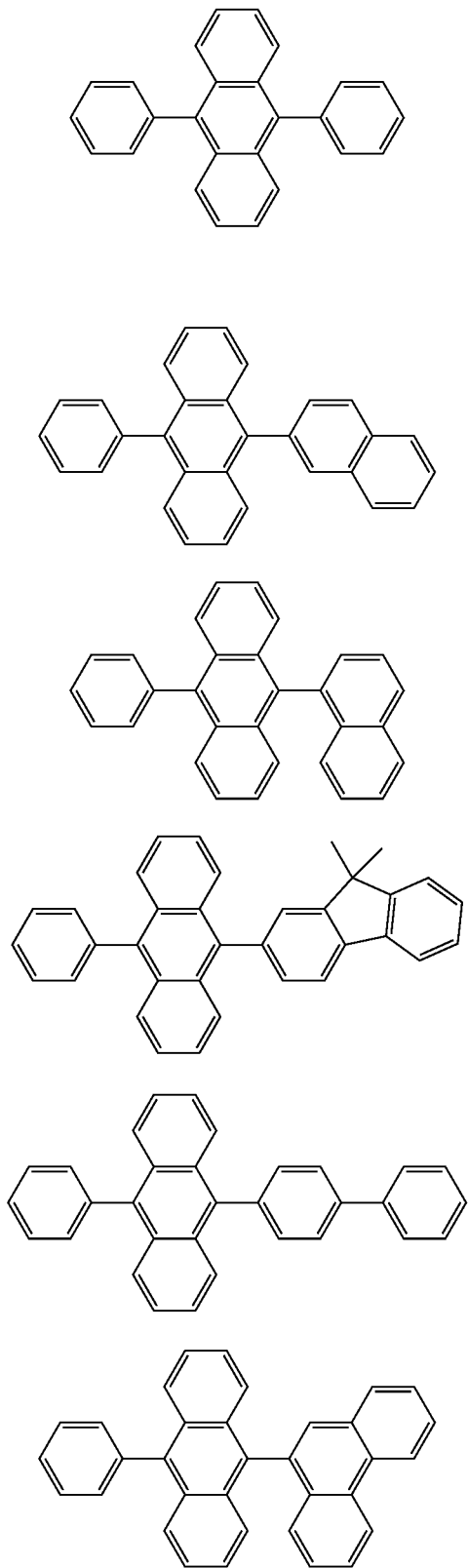
H-1
H-2
H-3
H-4
H-5
H-6
-continued
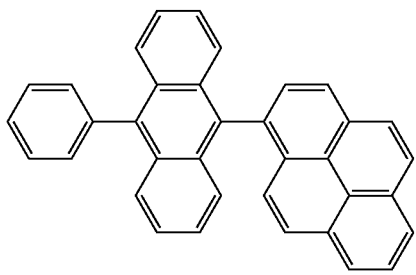
H-7
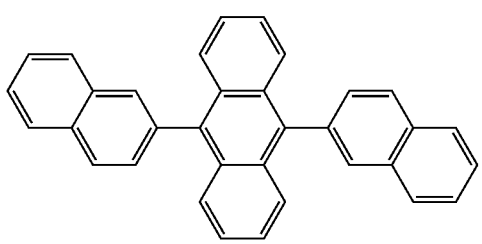
H-8
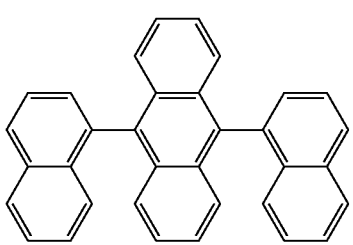
H-9
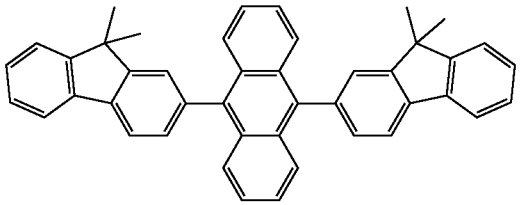
H-10
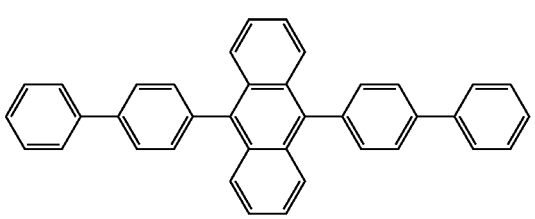
H-11
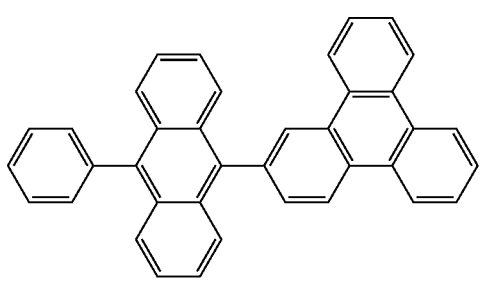
H-12

-continued
H-13
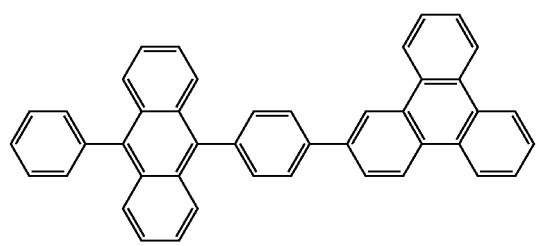
H-14
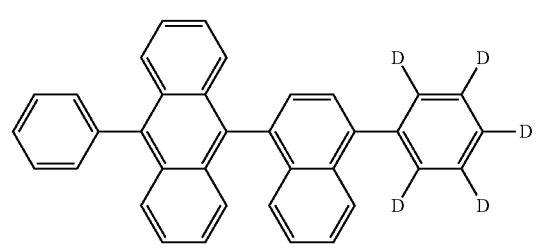
H-15
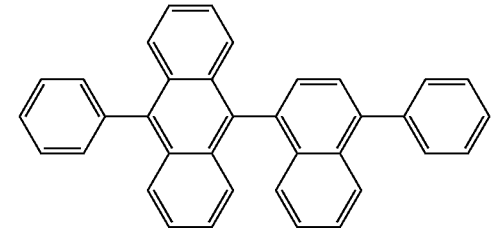
H-16
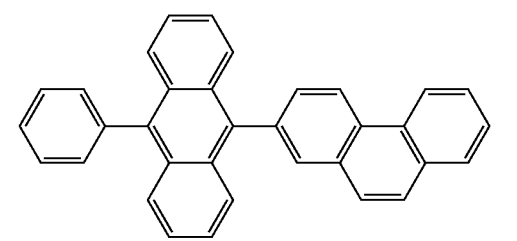
H-17
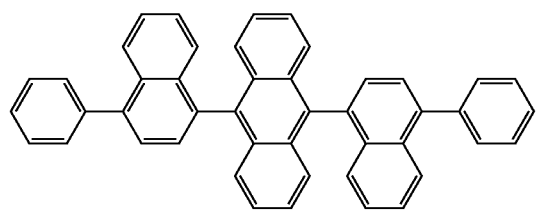
H-18
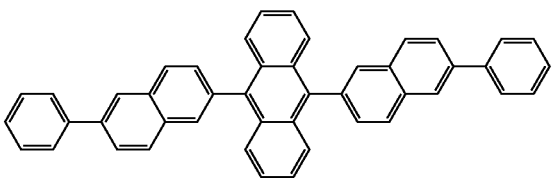
-continued
H-19
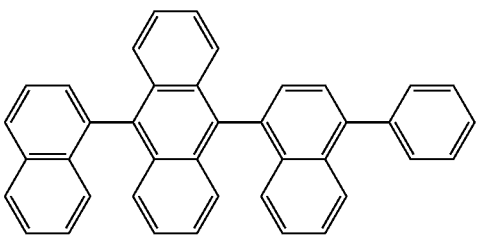
H-20
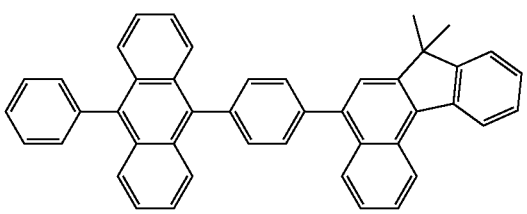
H-21
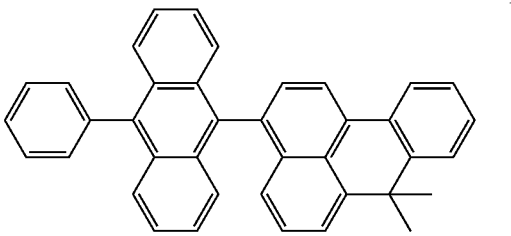
H-22
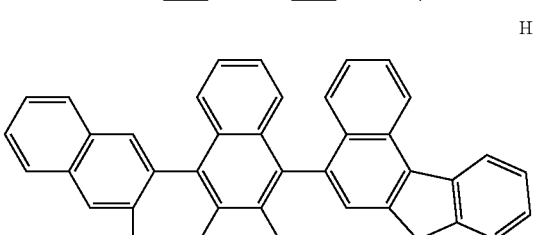
H-23
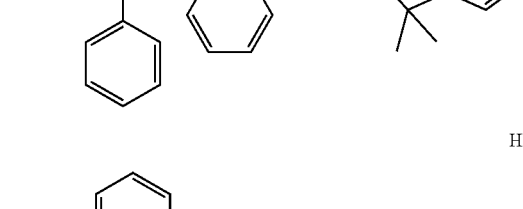
H-24
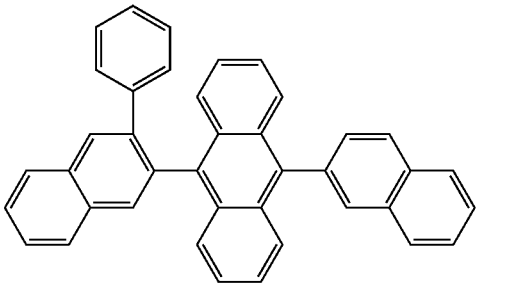
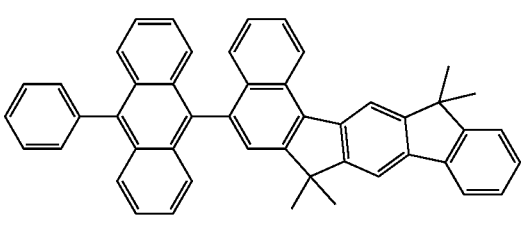

H-25
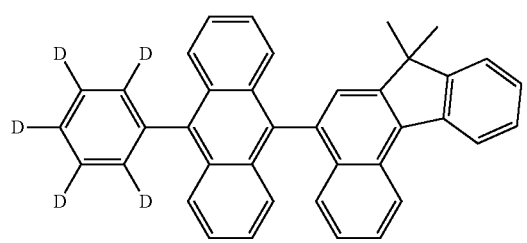
H-26
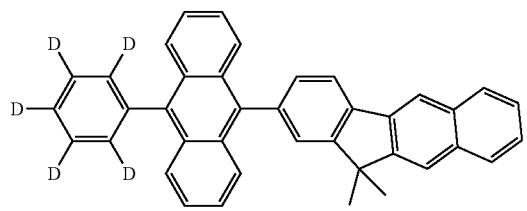
H-27
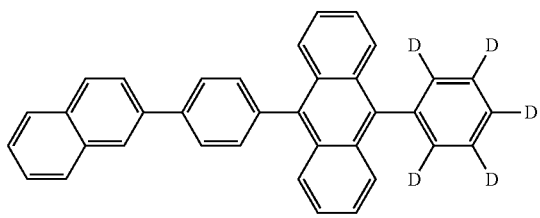
H-28
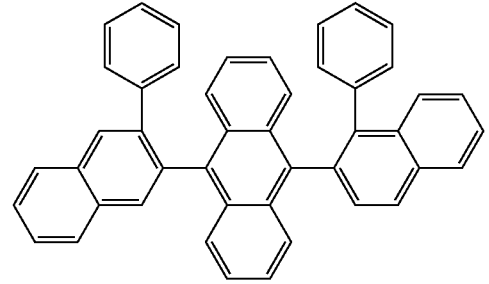
H-29
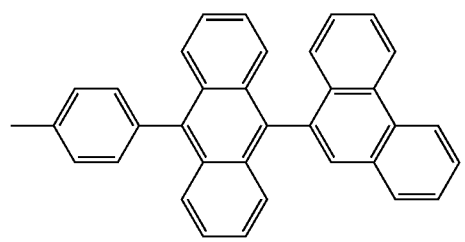
H-30
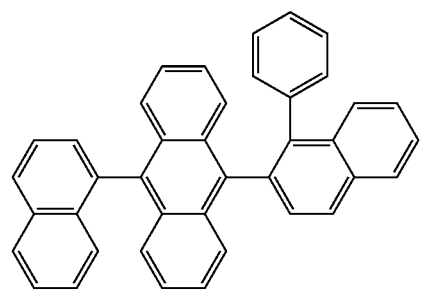
H-31
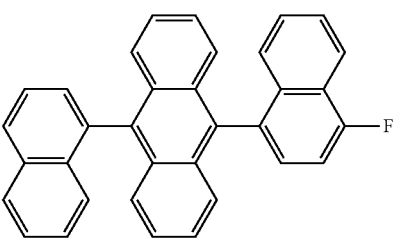
H-32
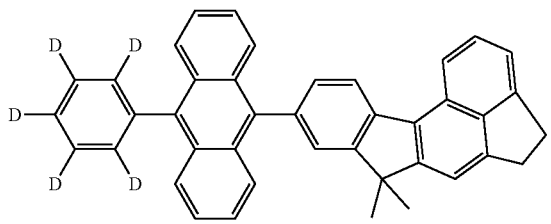
H-33
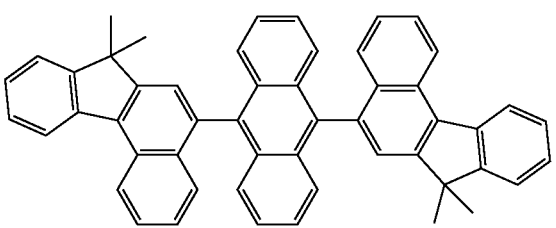
H-34
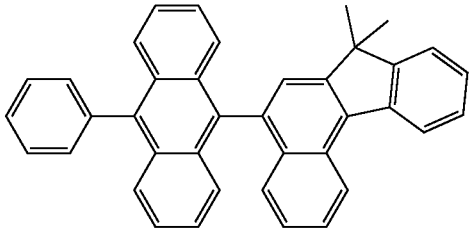
H-35
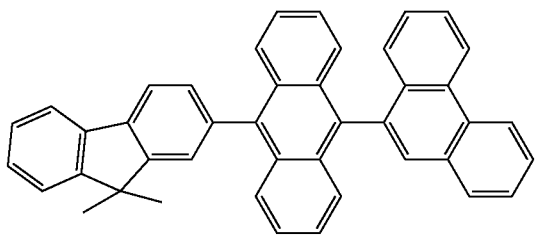
H-36
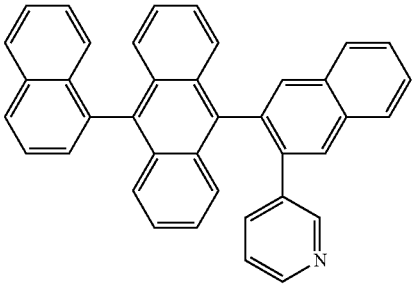

-continued
H-37
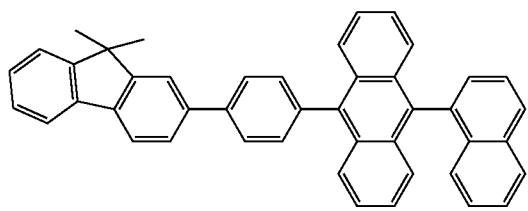
H-38
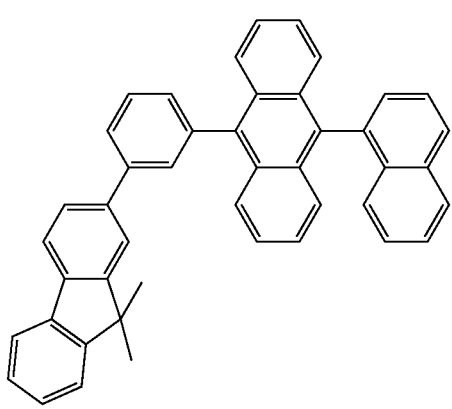
H-39
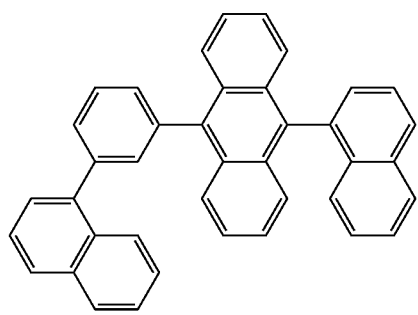
H-40
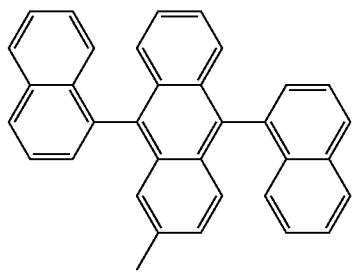
H-41
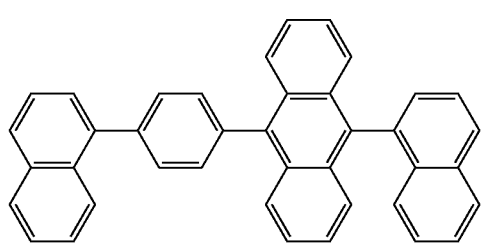
-continued
H-42
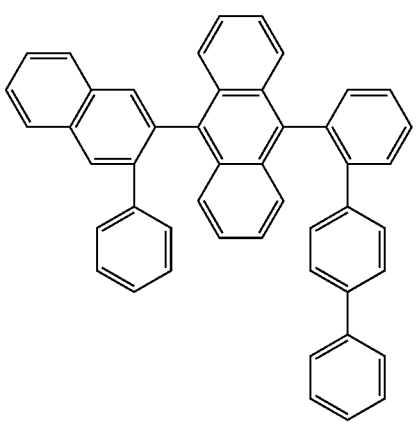
H-43
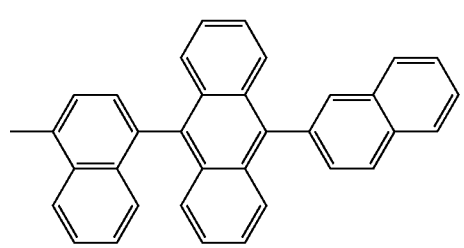
H-44
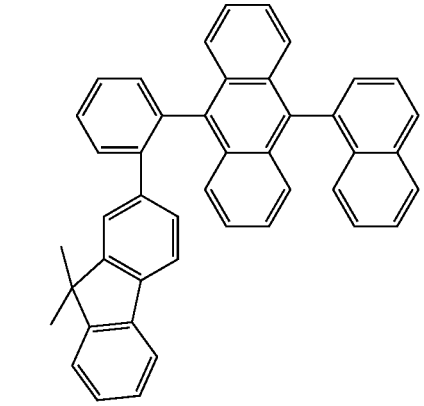
H-45
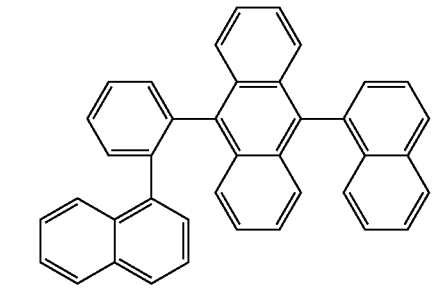
H-46
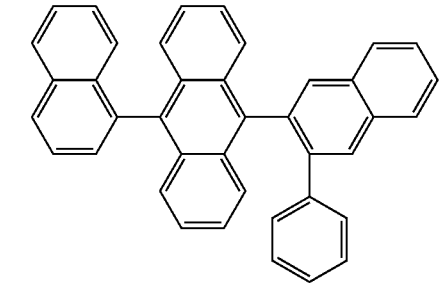

H-47
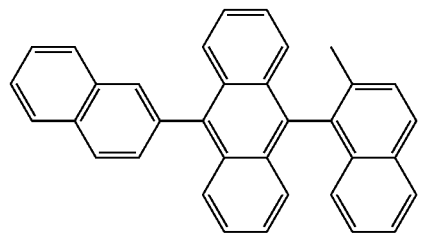
H-48
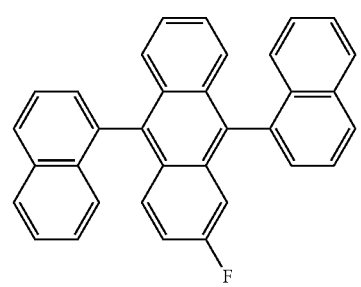
H-49
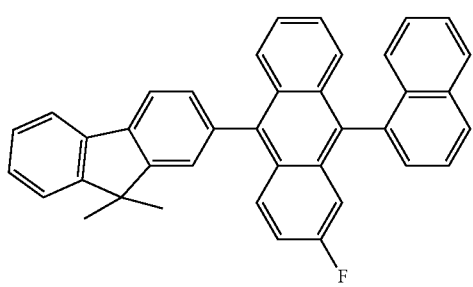
H-50
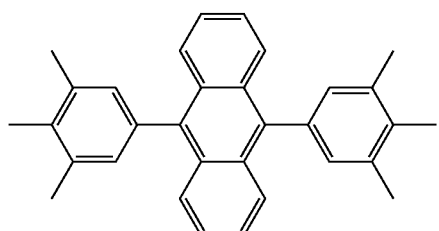
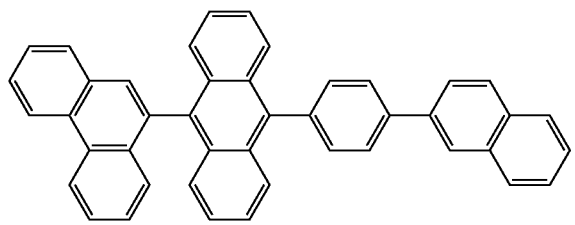
H-52
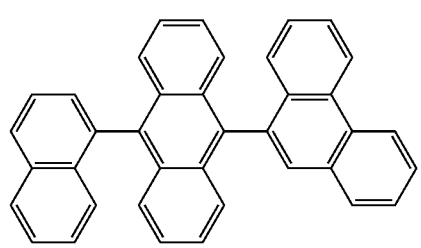
H-53
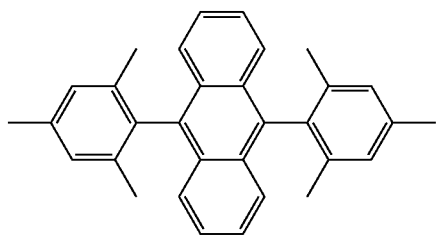
H-54
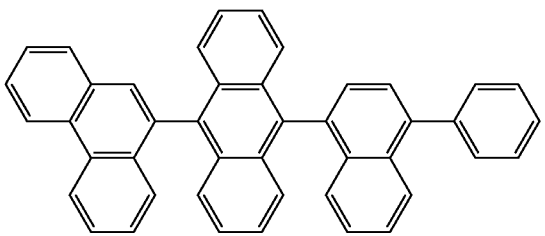
H-55
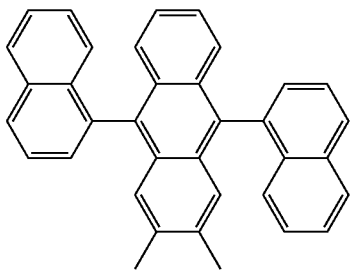
H-56
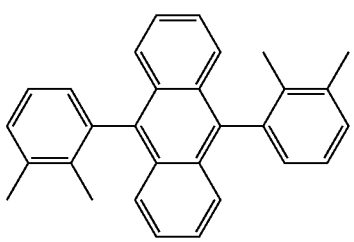
H-57
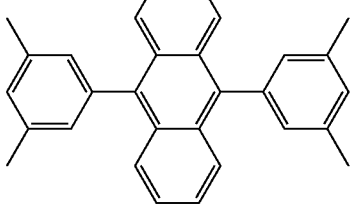
H-58
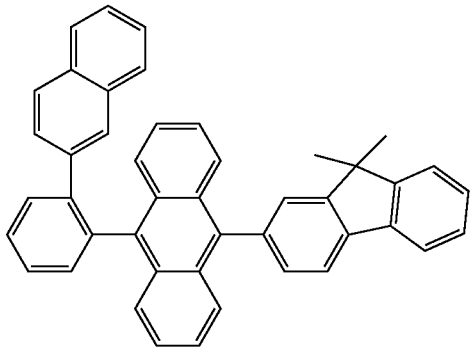

-continued
H-59
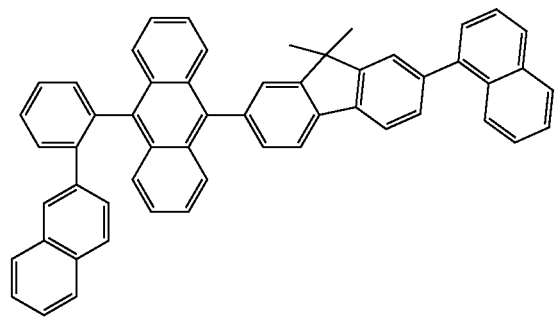
H-60
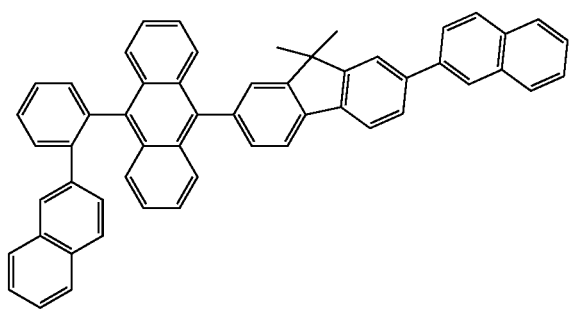
H-61
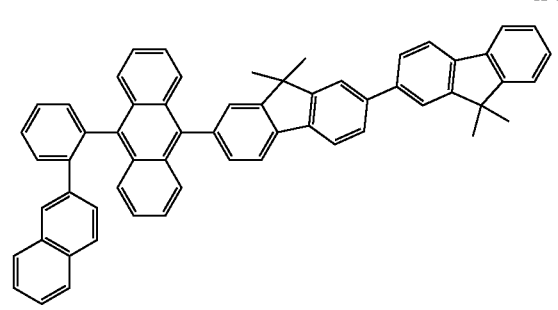
H-62
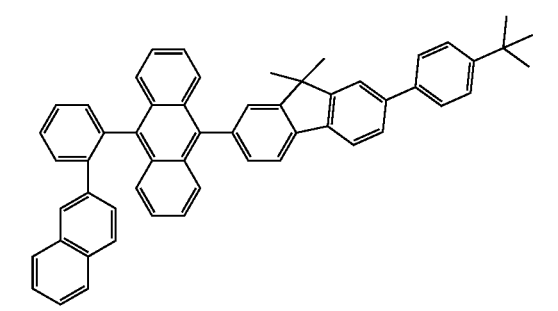
H-63
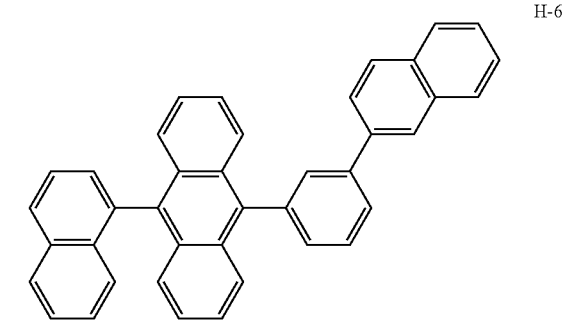
-continued
H-64
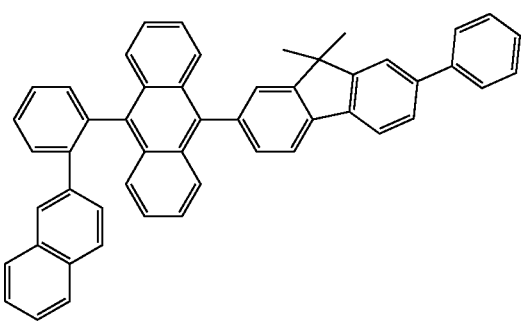
H-65
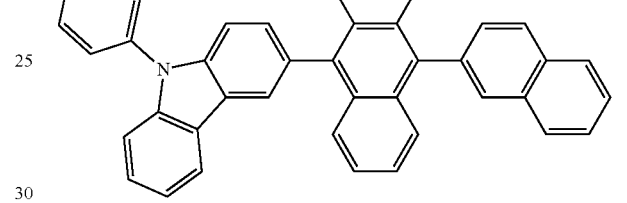
H-66
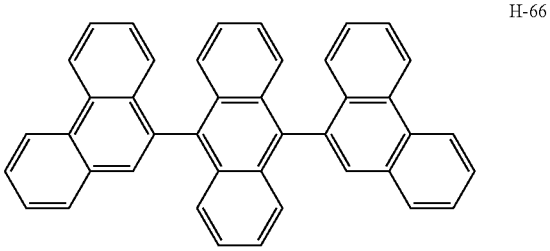
H-67
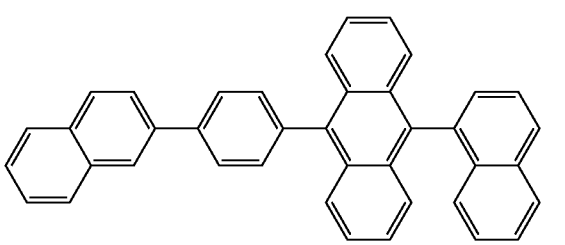
H-68
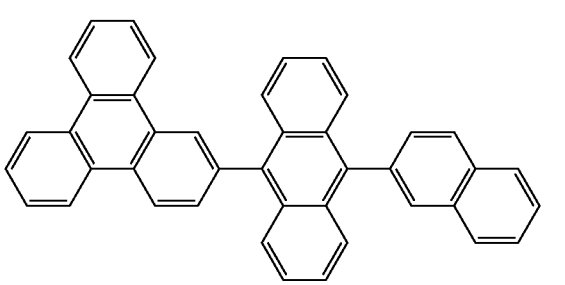

H-69
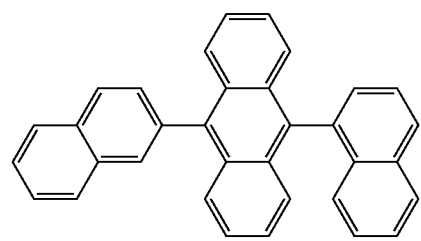
H-70
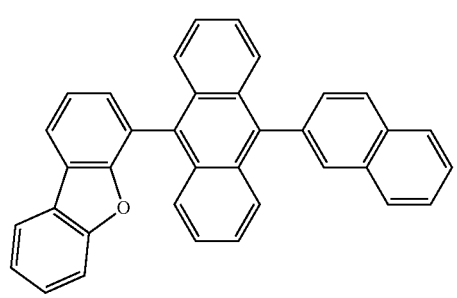
H-71
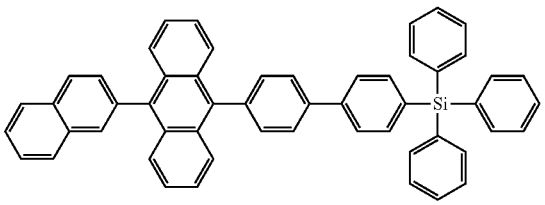
H-72
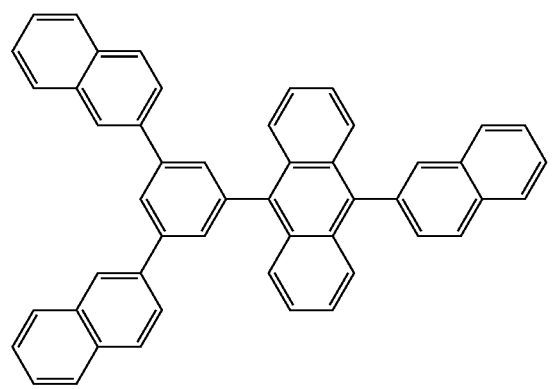
H-73
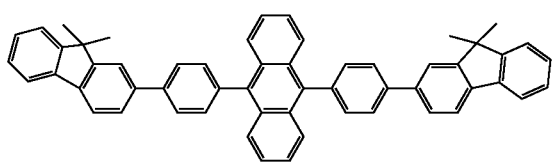
H-74
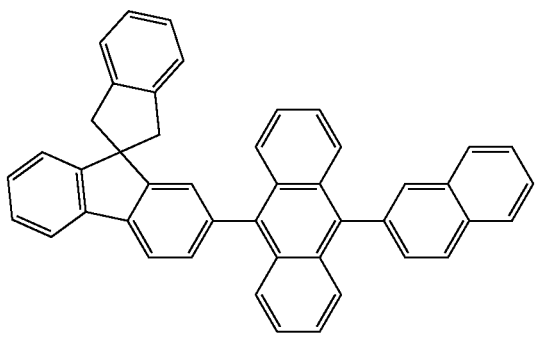
H-75
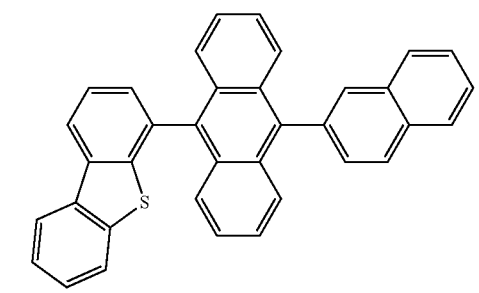
H-76
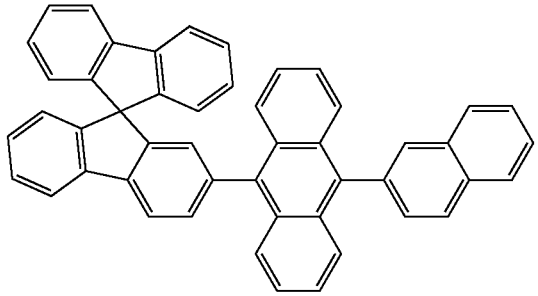
H-77
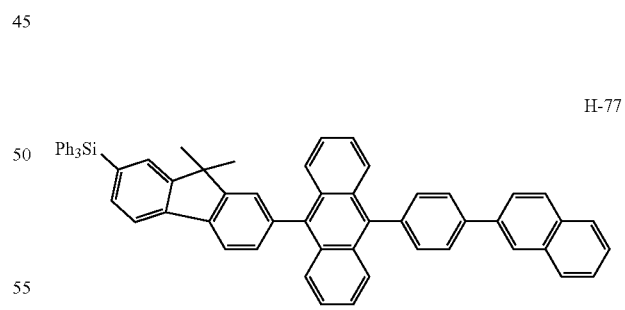
H-78
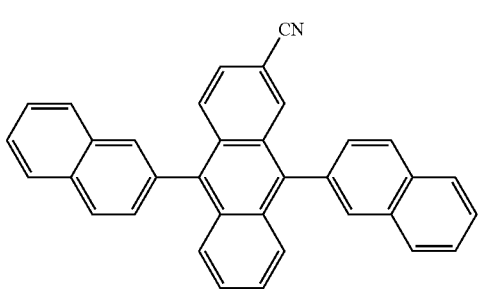

H-79
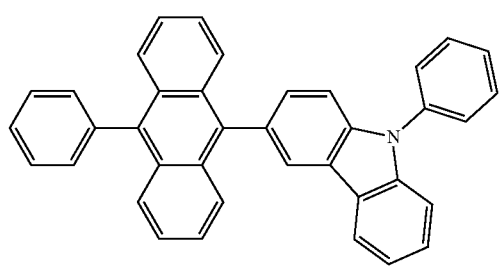
H-84
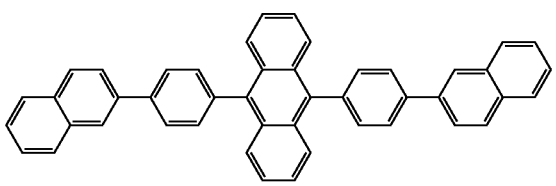
H-85
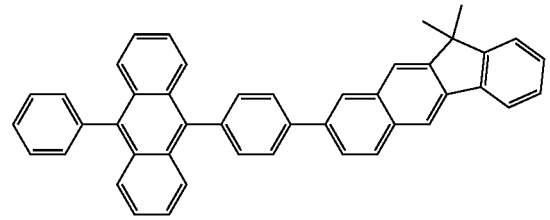
H-80
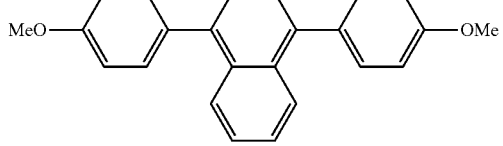
H-86
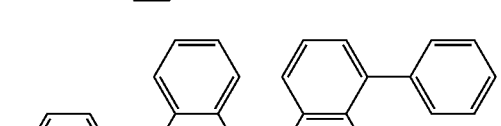
H-81
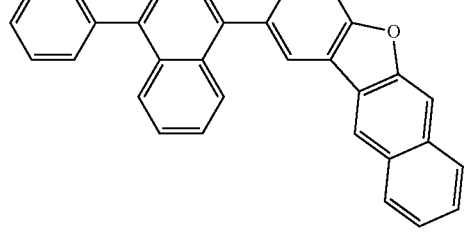
H-87
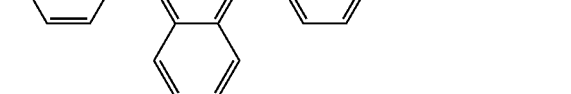
H-82
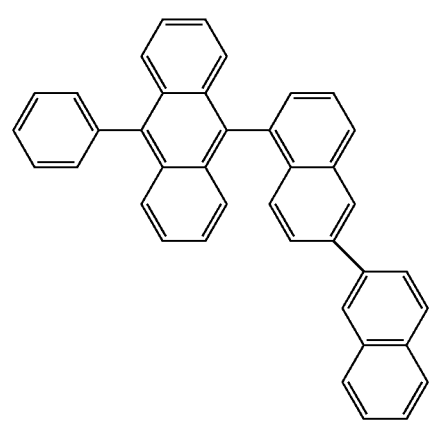
H-88
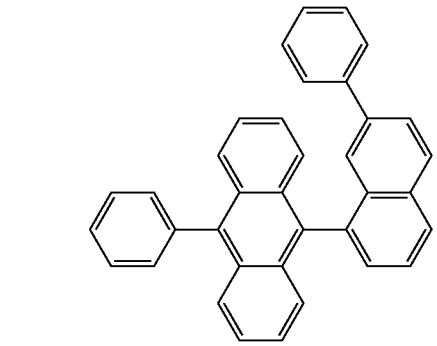
H-83
H-89
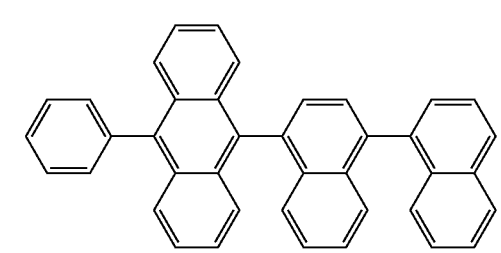

-continued
H-90
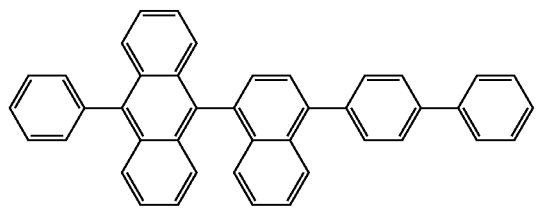
H-91
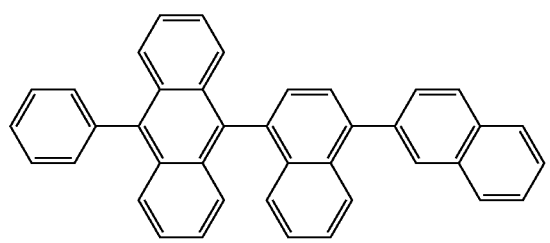
H-92
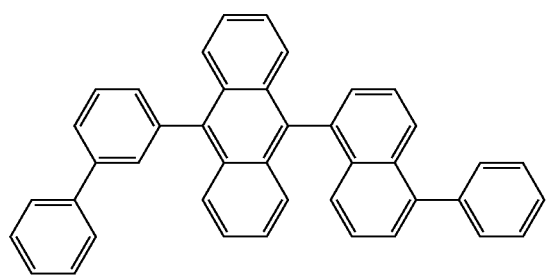
H-93
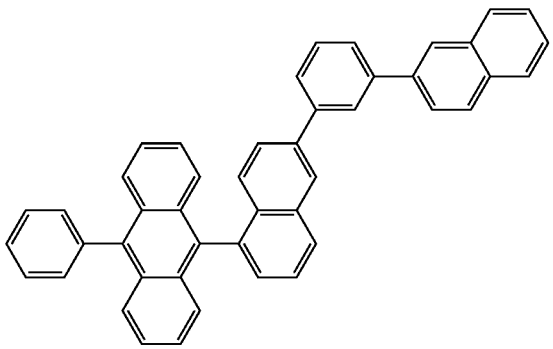
H-94
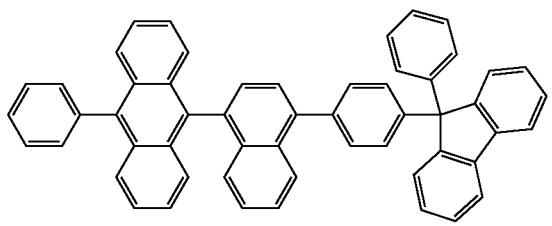
-continued
H-95
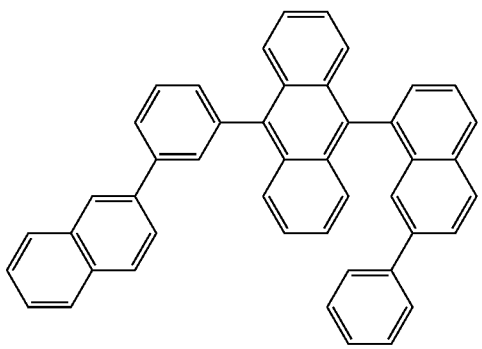
H-96
H-97
H-98
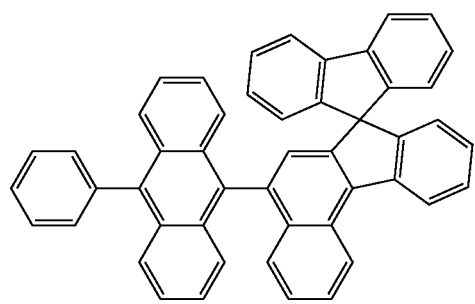

H-99

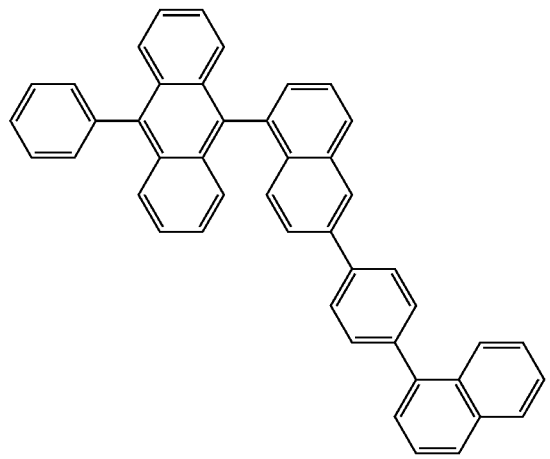

H-100

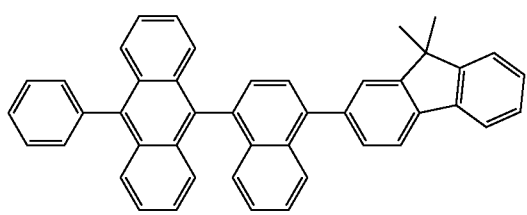

H-101

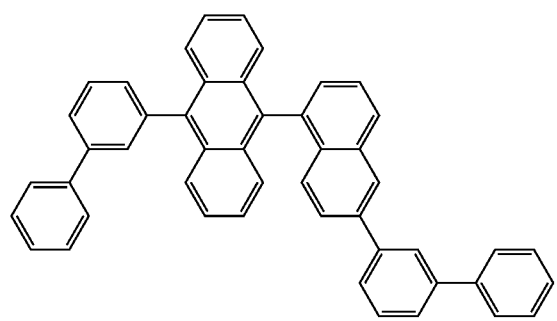

H-102

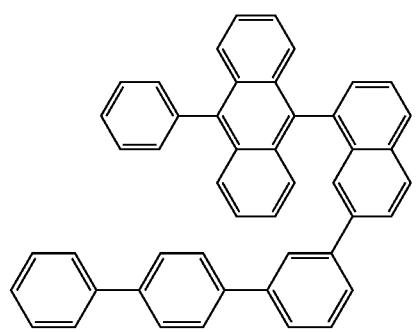

H-103

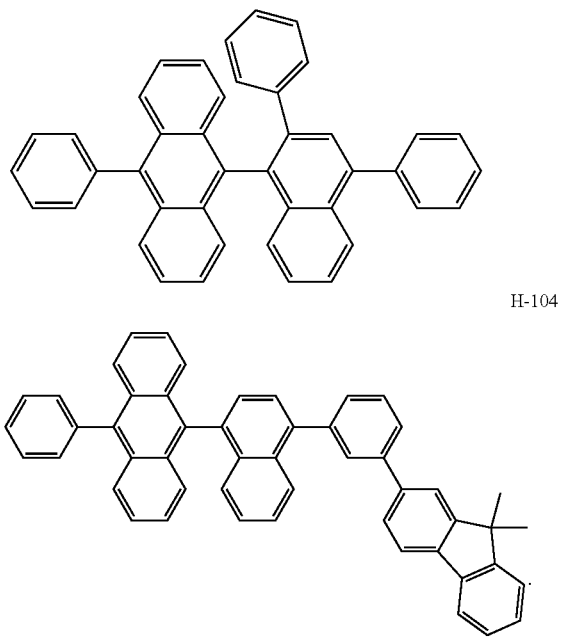

H-104

The dopant used in the present disclosure may be at least one phosphorescent dopant compound or at least one fluorescent dopant compound. Specifically, the dopant compound may be a fluorescent dopant compound, for example, a condensed polycyclic amine derivative represented by the following formula 21:

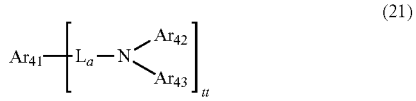

(21)

wherein $Ar_{41}$ represents a substituted or unsubstituted (C6-C50) aryl, or styryl;

$L_a$ represents a single bond, a substituted or unsubstituted (C6-C30)arylene, or a substituted or unsubstituted (3- to 30-membered)heteroarylene;

$Ar_{42}$ and $Ar_{43}$, each independently, represent hydrogen, deuterium, a halogen, a substituted or unsubstituted (C1-C30)alkyl, a substituted or unsubstituted (C6-C30)aryl, or a substituted or unsubstituted (3- to 30-membered)heteroaryl; or may be linked to an adjacent substituent to form a mono- or polycyclic, (3- to 30-membered) alicyclic or aromatic ring, or the combination thereof, whose carbon atom(s) may be replaced with at least one heteroatom selected from nitrogen, oxygen, and sulfur; and tt represents 1 or 2, in which if tt represents 2, each

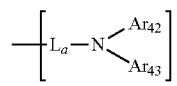

may be the same or different.

Preferably, the aryl group in $Ar_{41}$ includes a substituted or unsubstituted phenyl, a substituted or unsubstituted fluorenyl group, a substituted or unsubstituted anthryl group, a substituted or unsubstituted pyrenyl group, a substituted or unsubstituted chrysenyl group, a substituted or unsubstituted benzofluorenyl group, spiro[fluorene-benzofluorene], etc.
The compound represented by formula 21 includes the following compounds, but is not limited thereto:
D-1
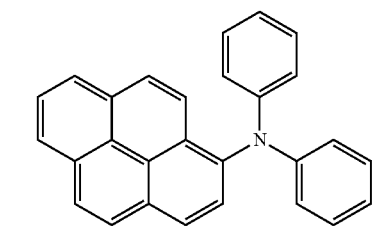
D-2
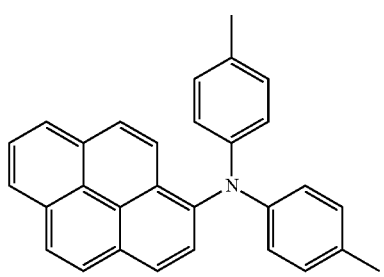
D-3
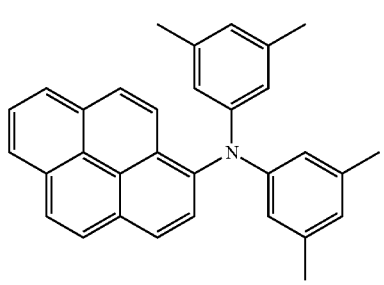
D-4
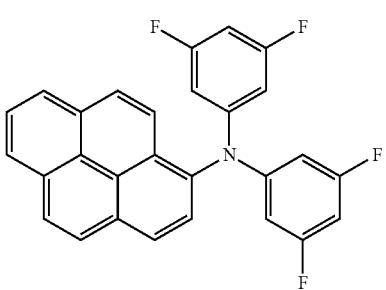
D-5
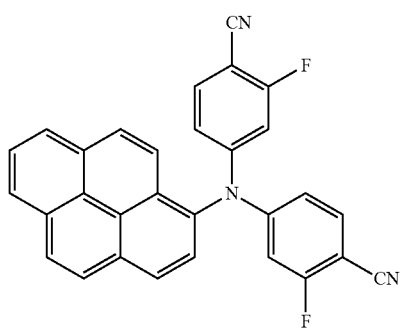
D-6
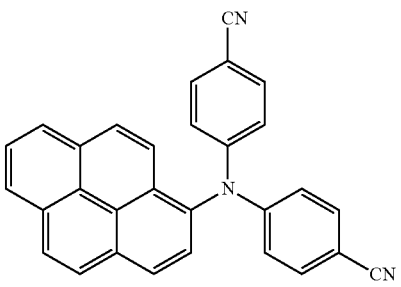
D-7
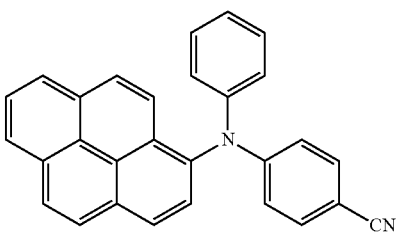
D-8
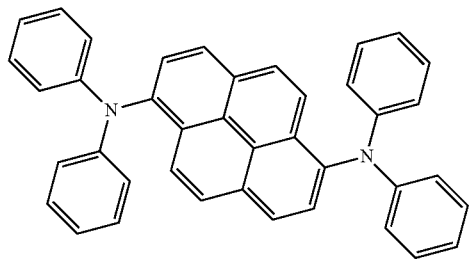
D-9
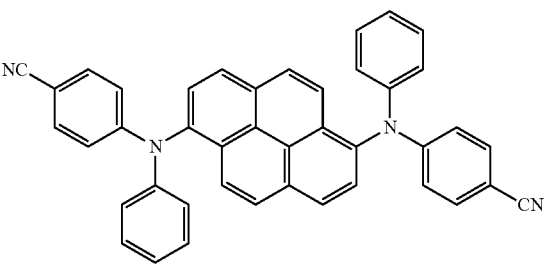
D-10
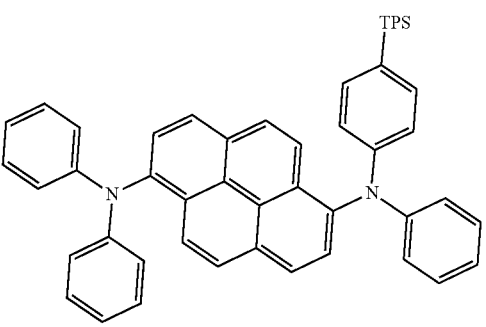

D-11
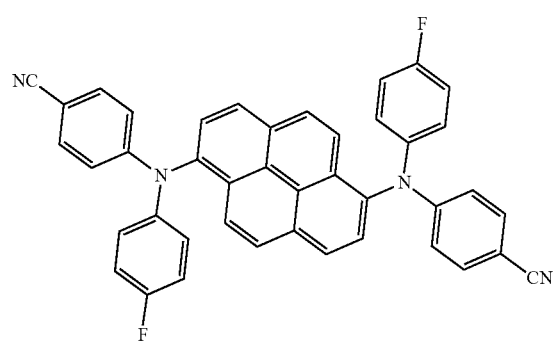
D-15
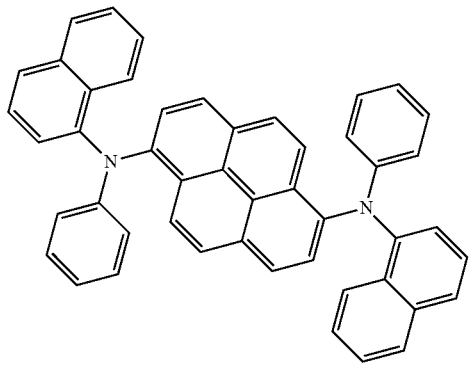
D-12
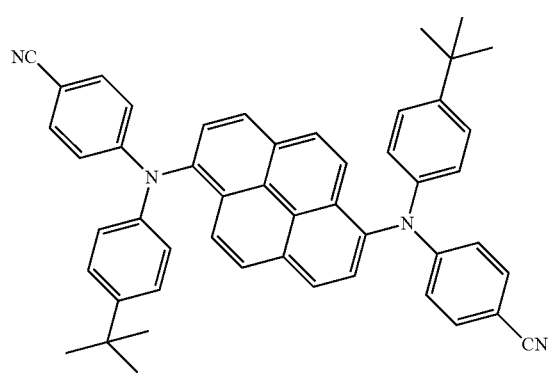
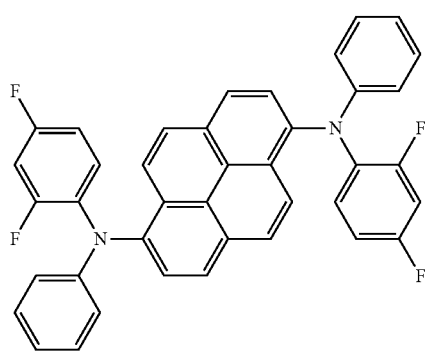
D-13
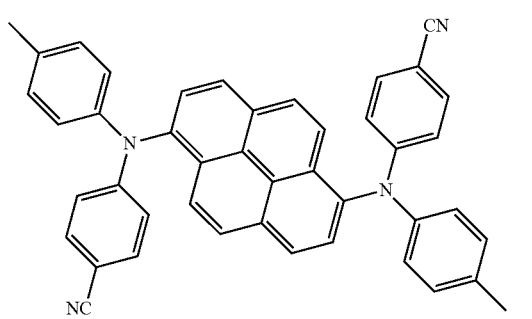
D-17
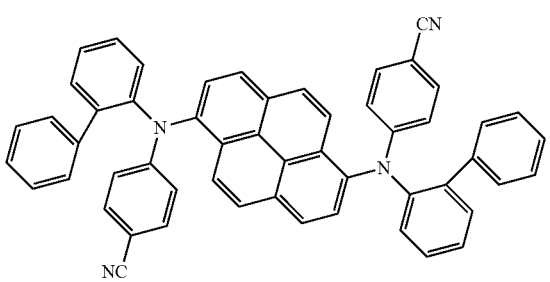
D-14
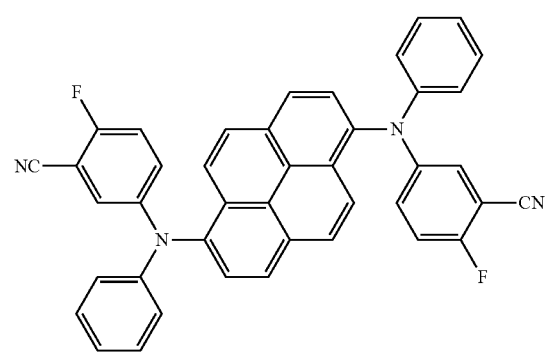
D-18
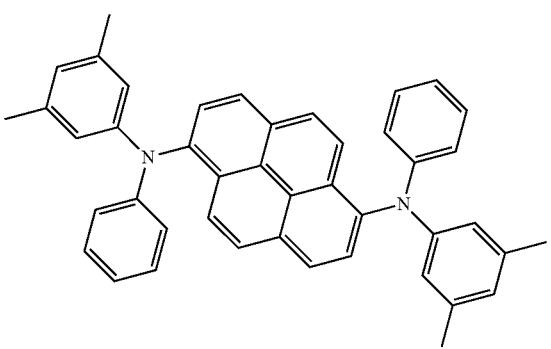

-continued
D-19
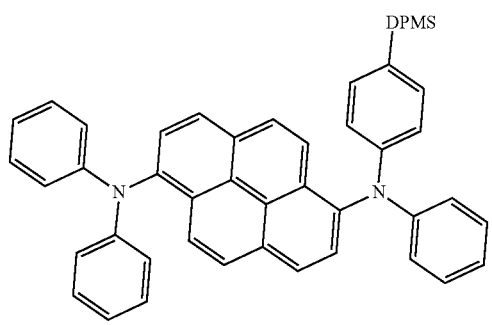
D-23
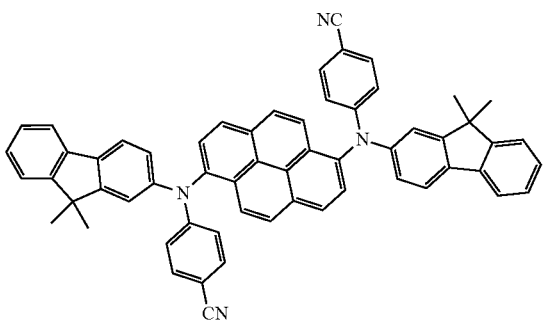
D-20
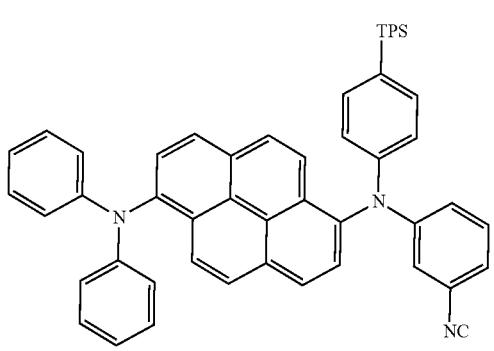
D-24
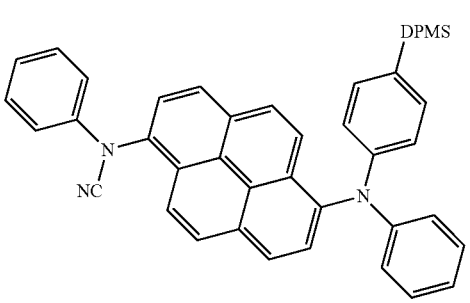
D-21
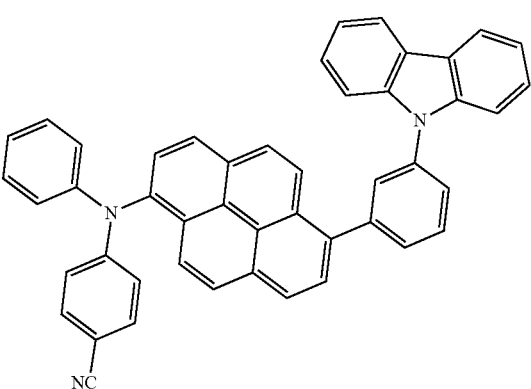
D-25
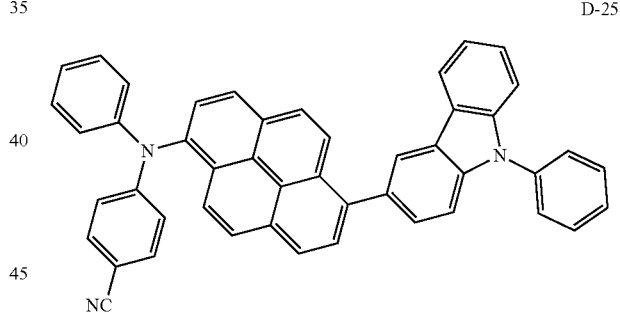
D-22
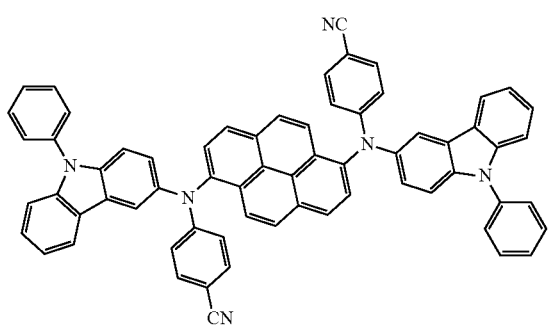
D-26
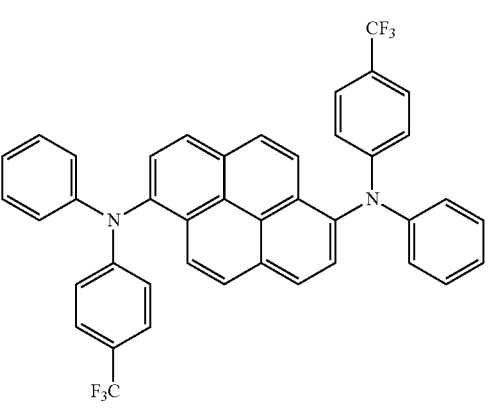

D-27
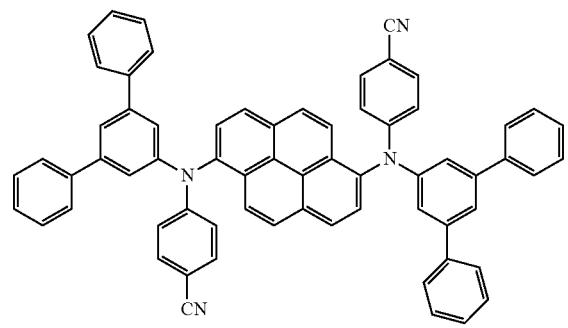
D-28
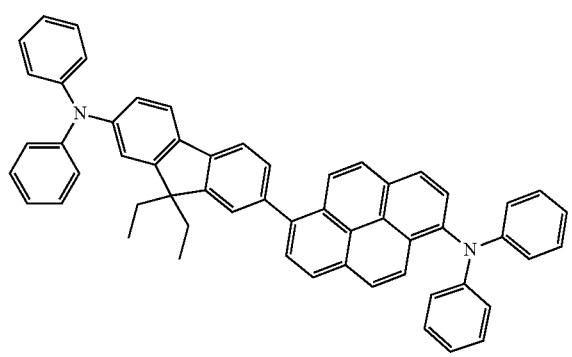
D-29
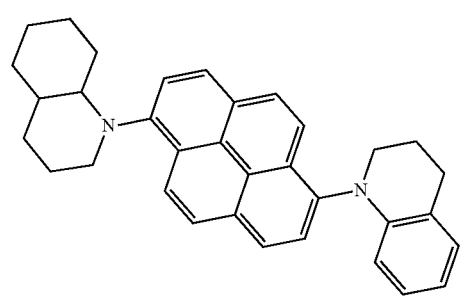
D-30
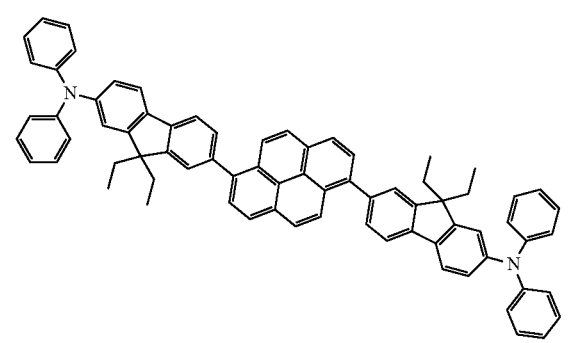
D-31
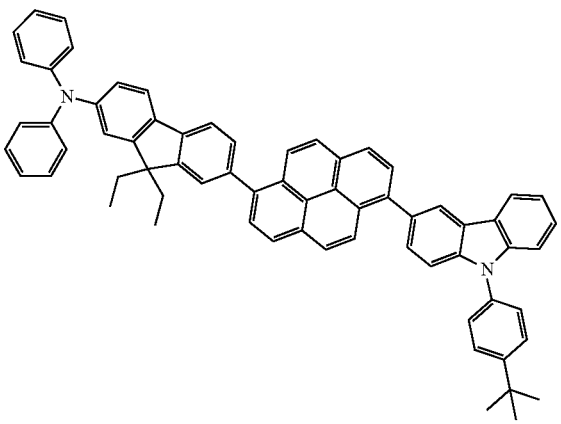
D-32
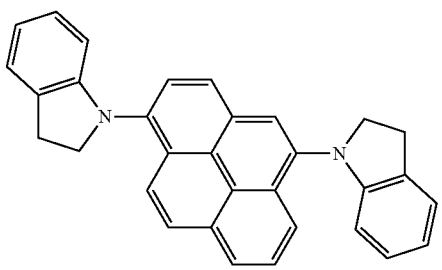
D-33
D-34
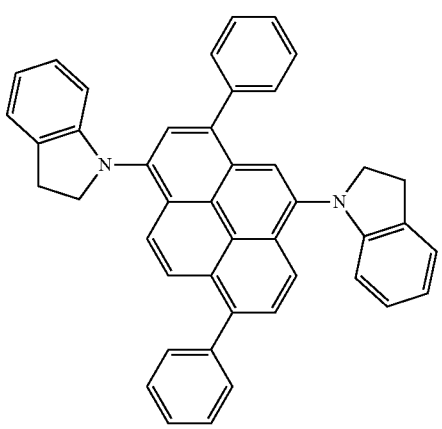

D-35
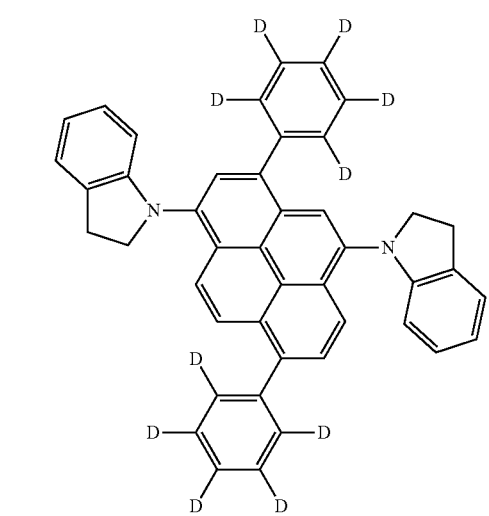
D-38
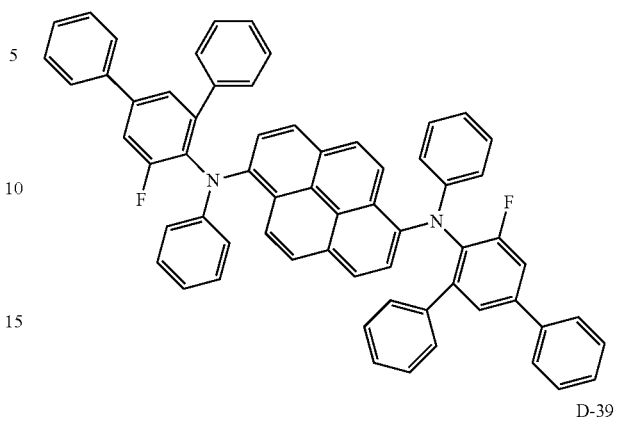
D-39
D-36
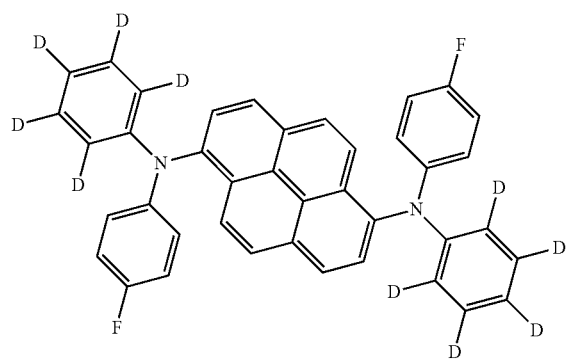
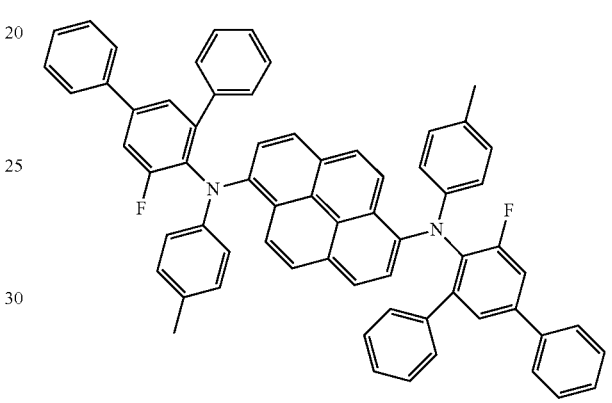
D-40
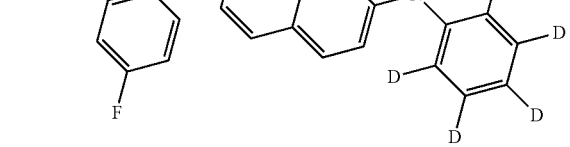
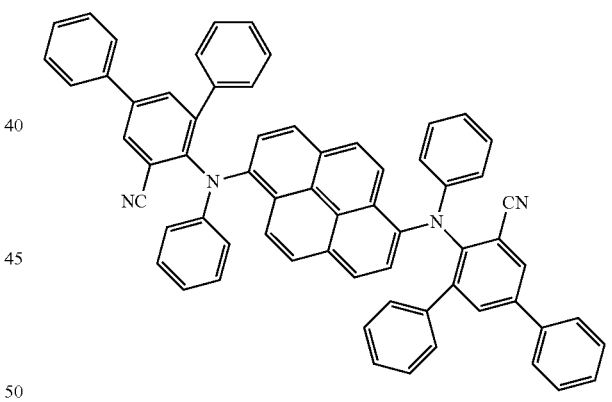
D-41
D-37
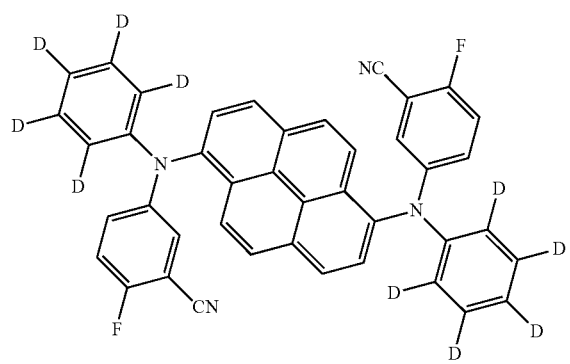
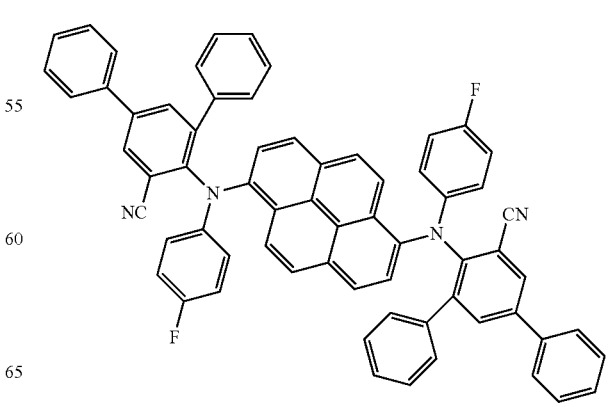

D-42
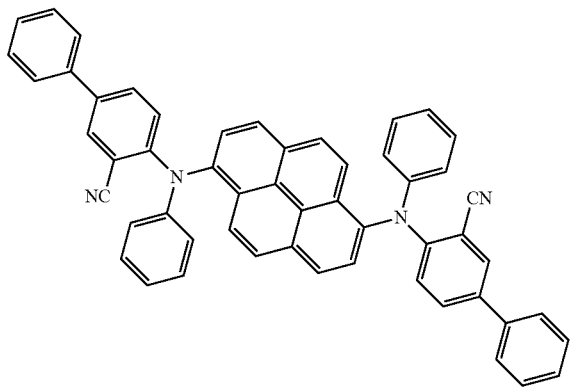
D-45
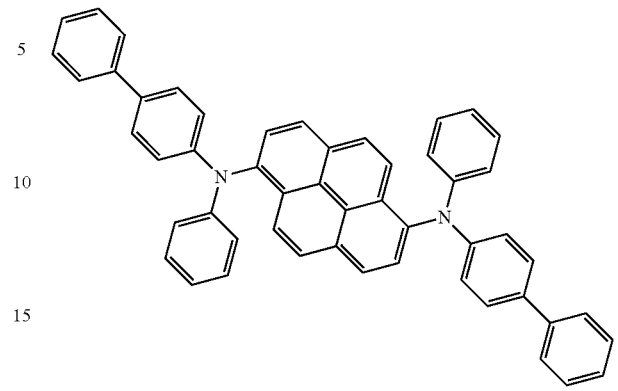
D-43
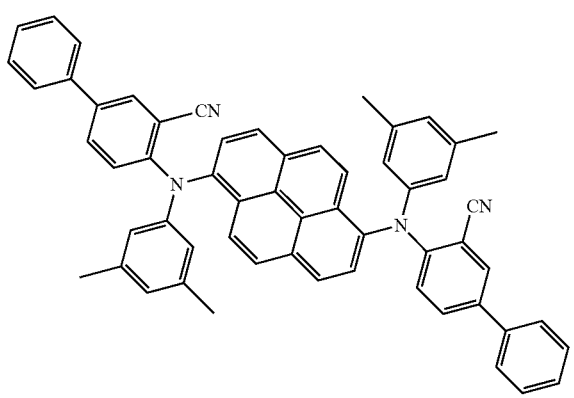
D-46
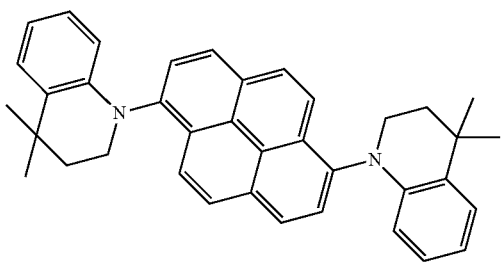
D-47
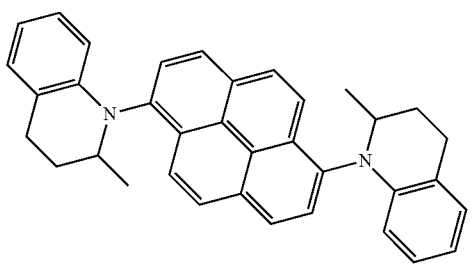
D-48
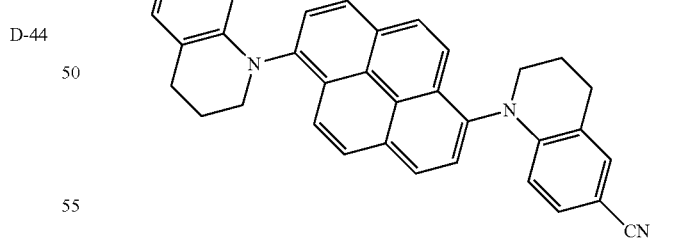
D-44
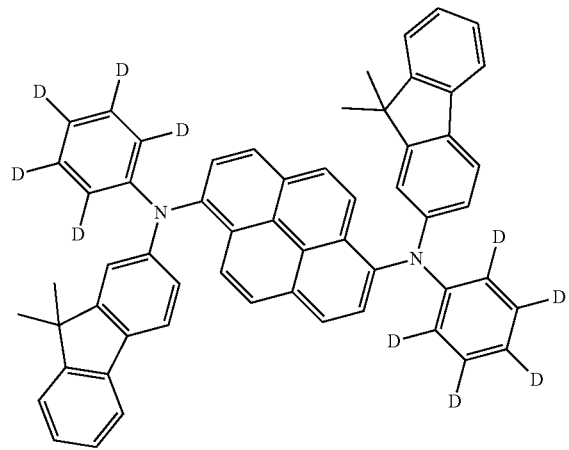
D-49
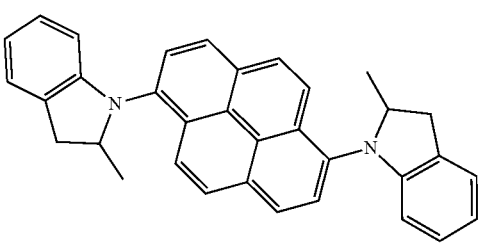

-continued
D-50
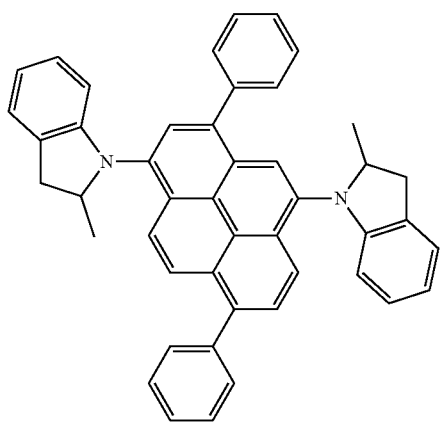
D-51
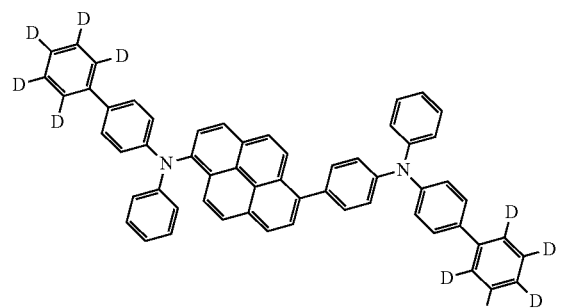
D-52
D-53
-continued
D-54
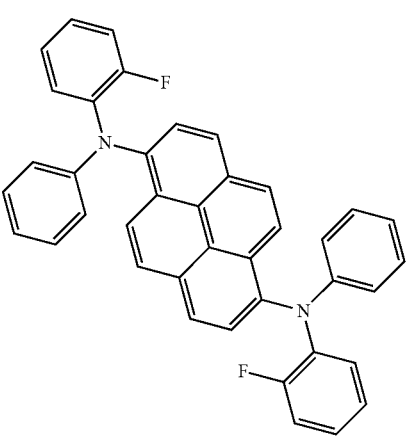
D-55
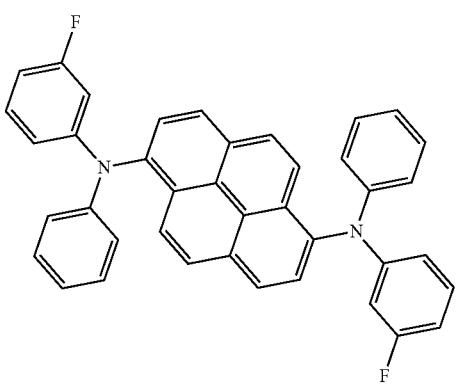
D-56
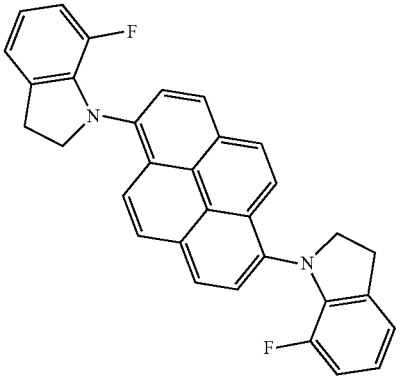
D-57
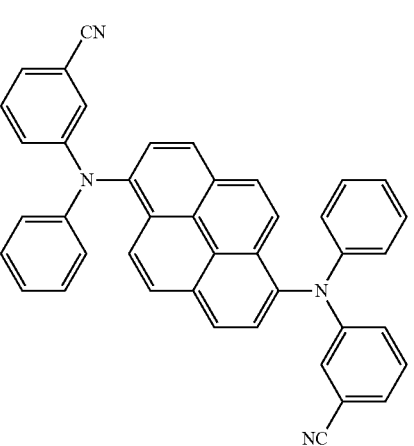

D-58
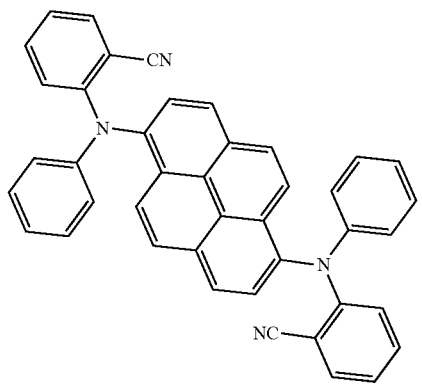
D-62
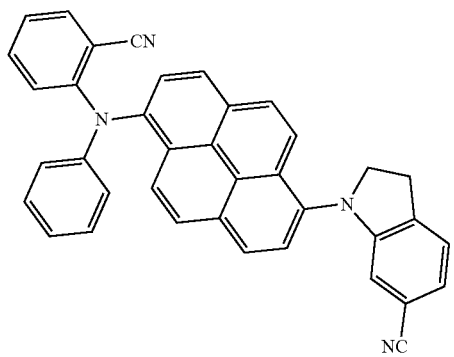
D-59
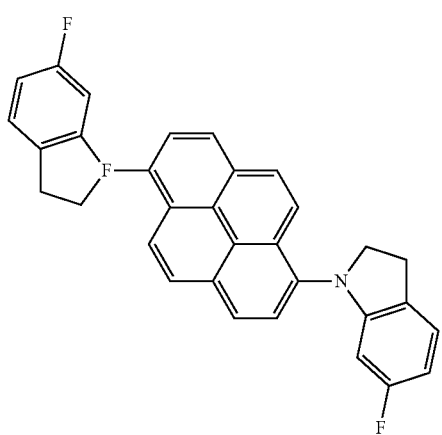
D-63
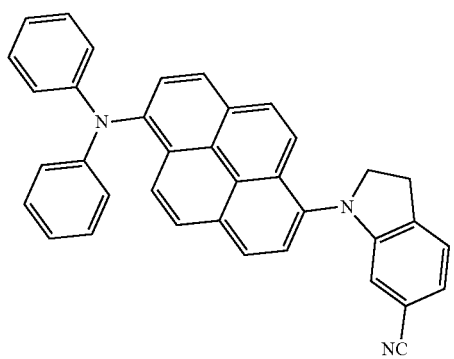
D-60
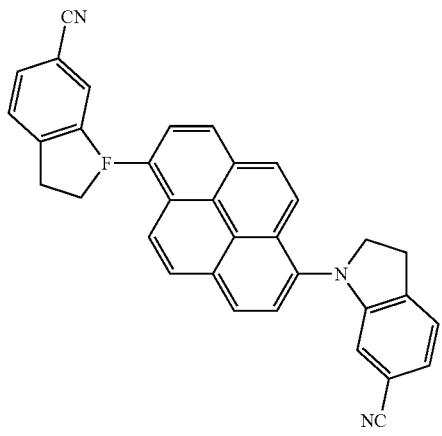
D-64
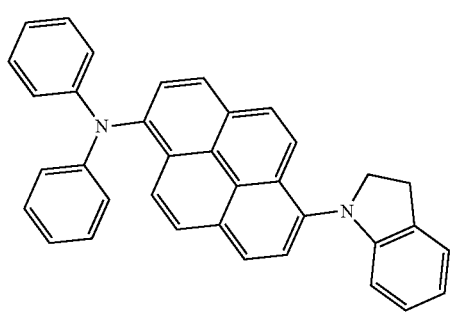
D-61
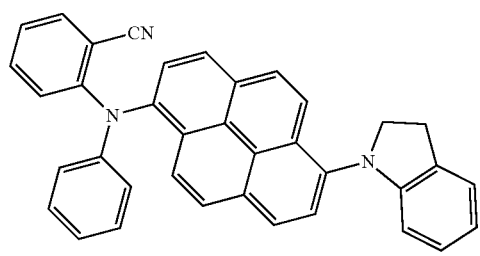
D-65
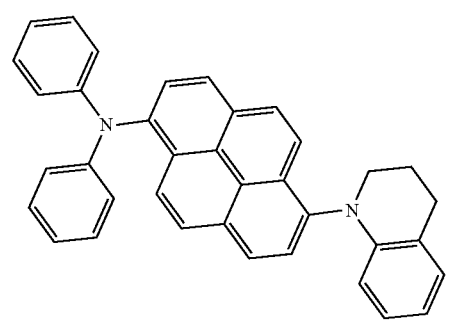

D-66
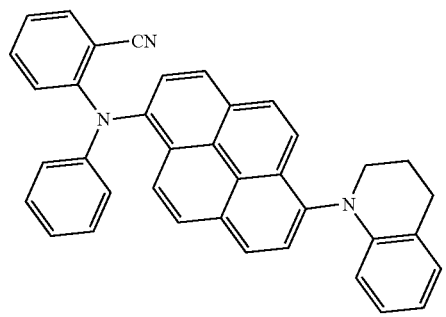
D-67
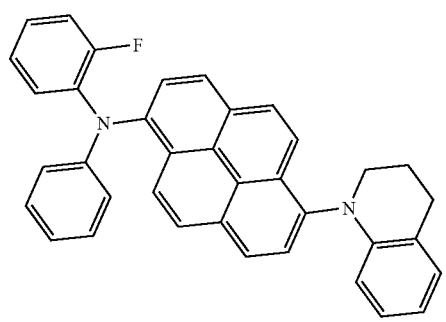
D-68
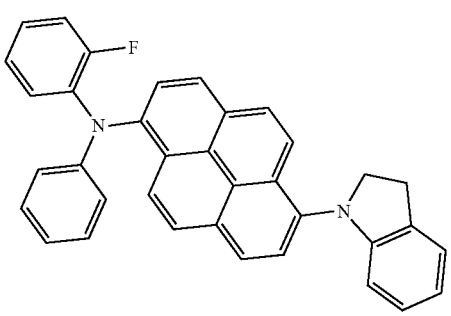
D-69
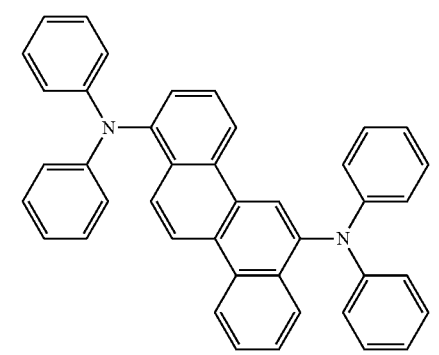
D-70
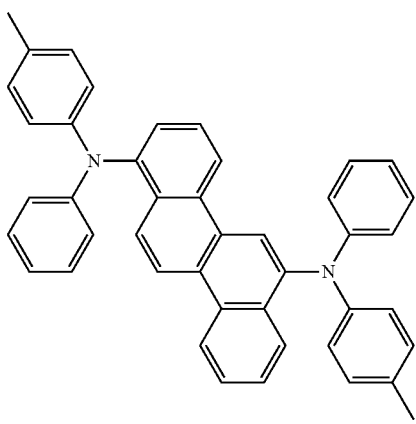
D-71
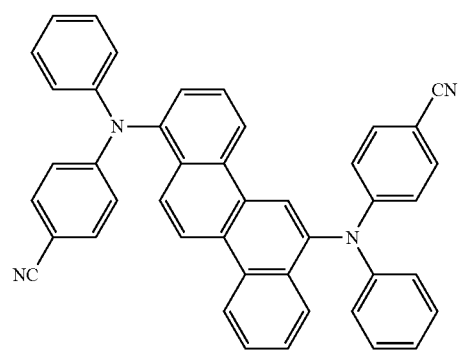
D-72
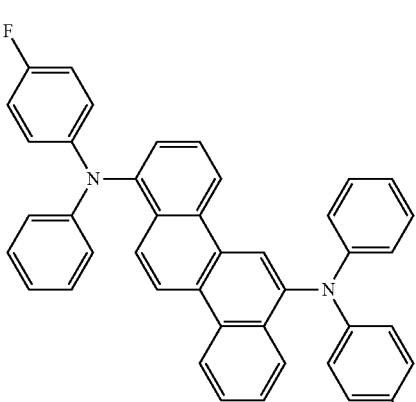
D-73
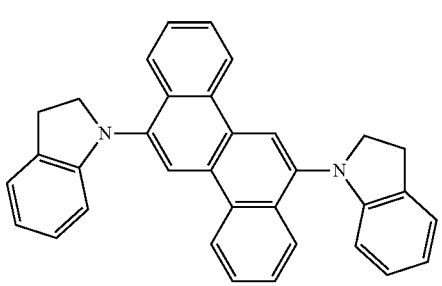

D-74
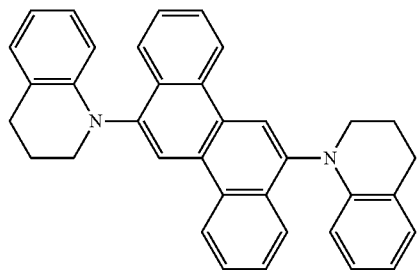
D-75
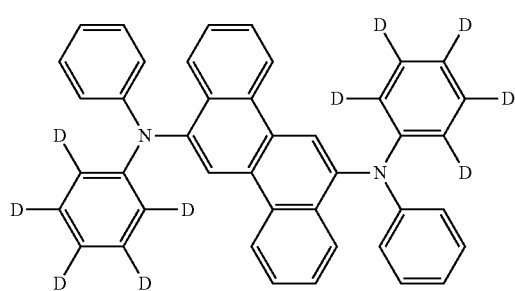
D-76
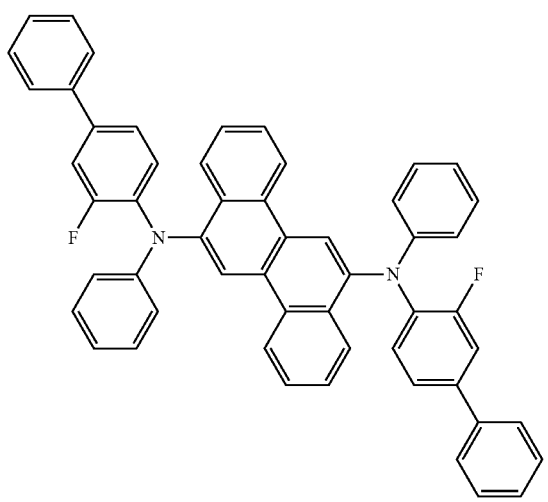
D-77
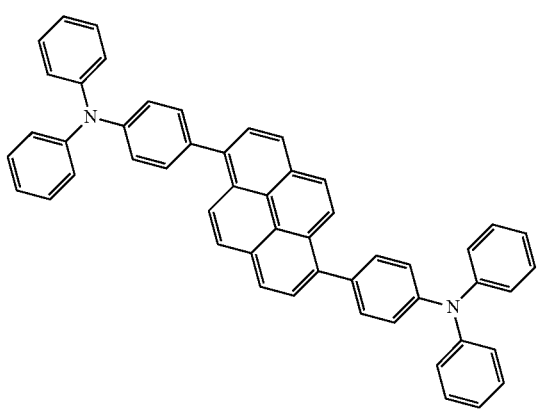
D-78
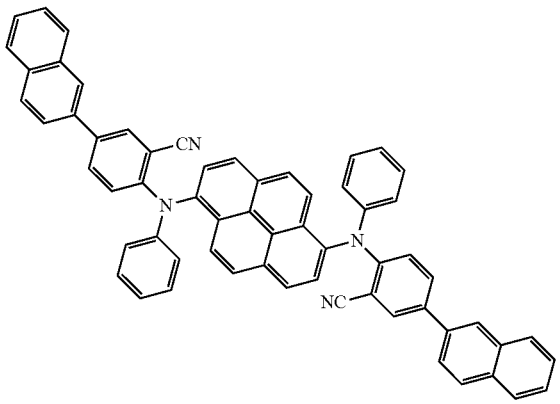
D-79
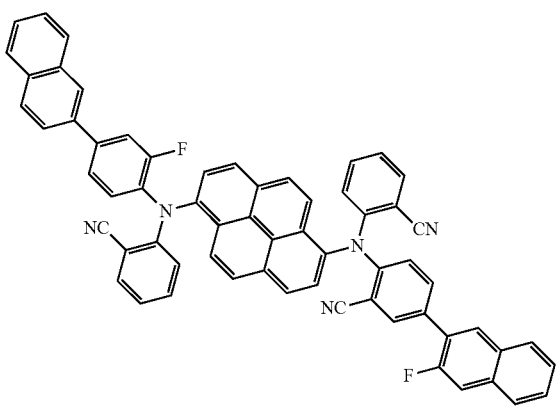
D-80
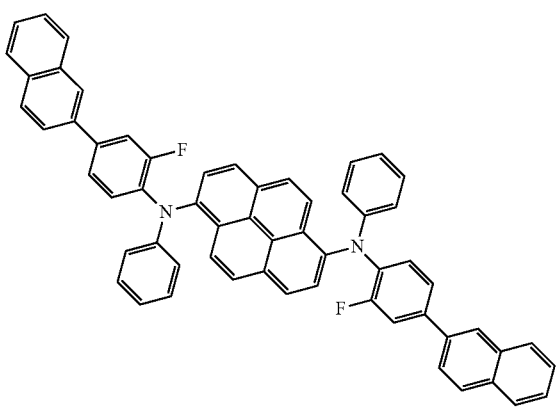

D-81
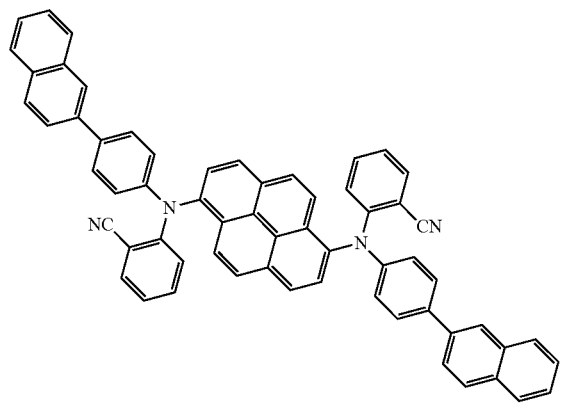
D-85
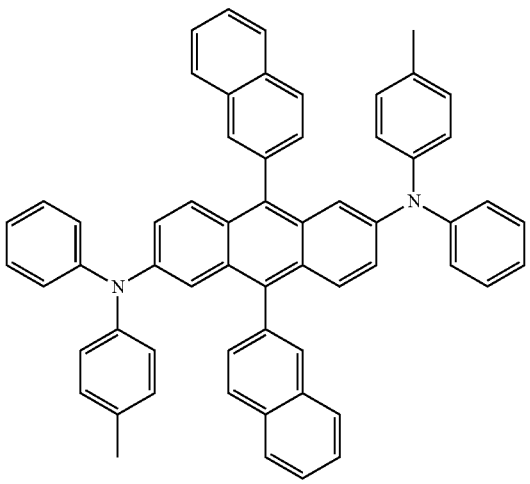
D-82
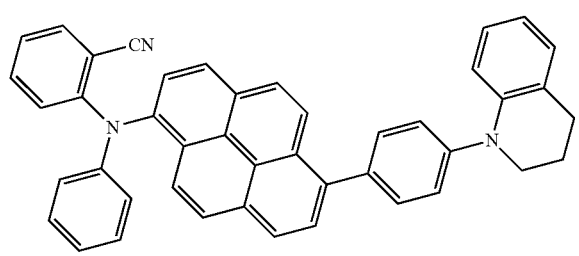
D-86
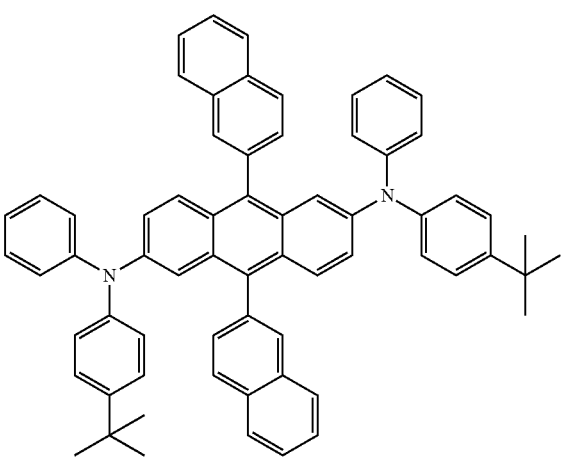
D-83
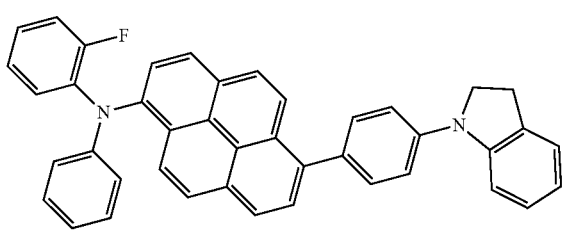
D-84
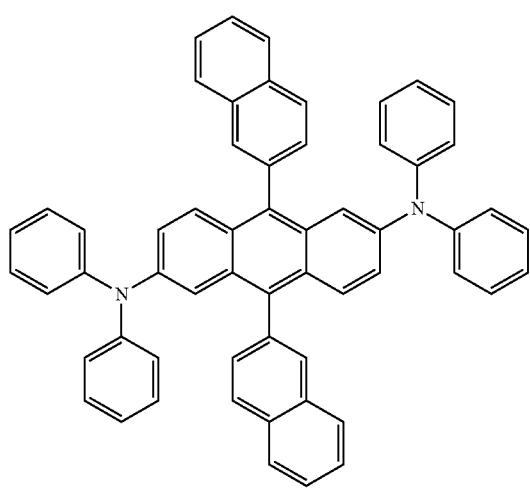
D-87
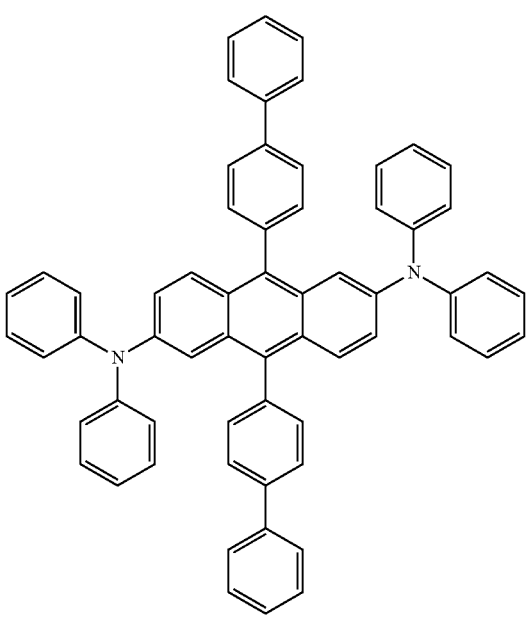

D-88
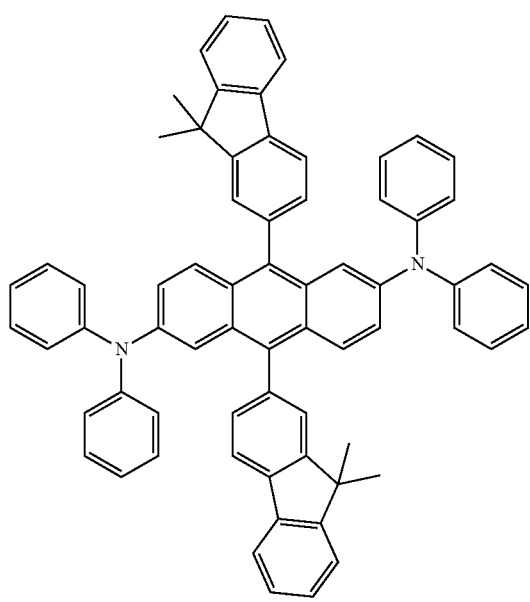
D-89
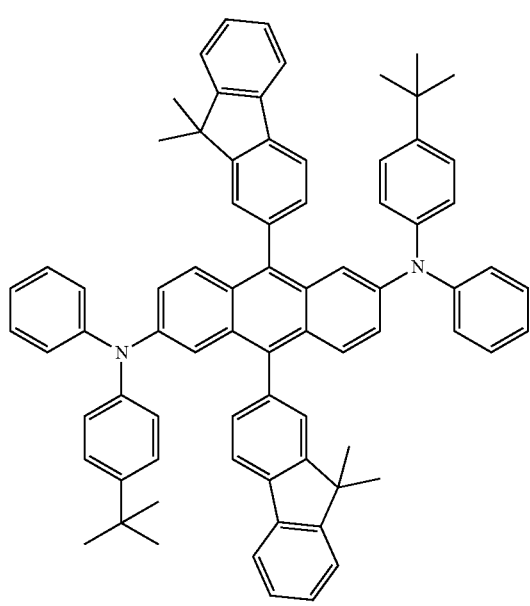
D-90
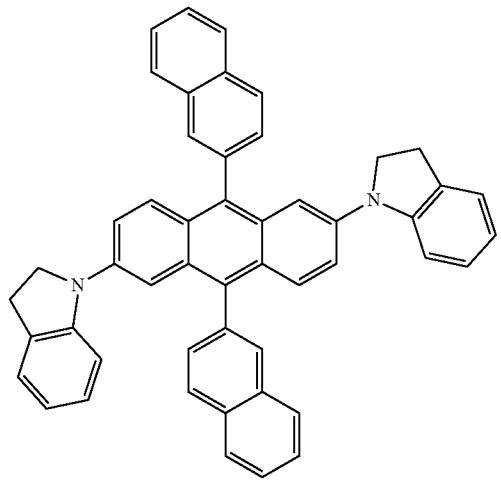
D-91
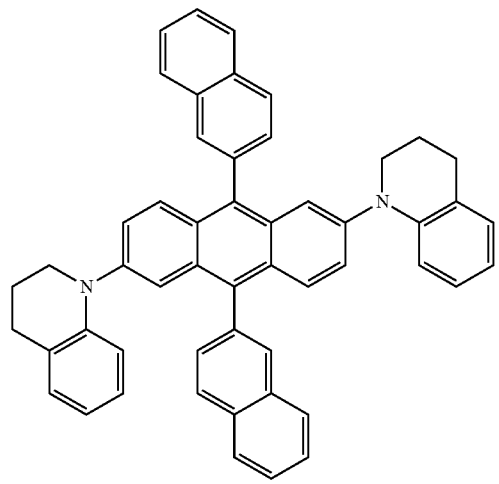
D-92
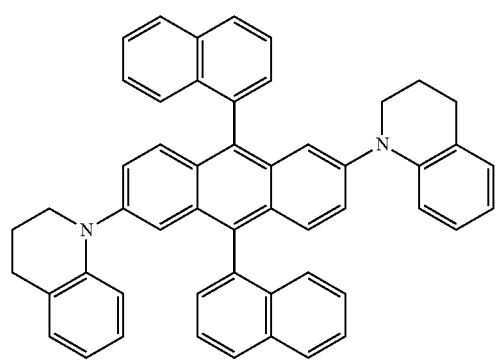

-continued
D-93
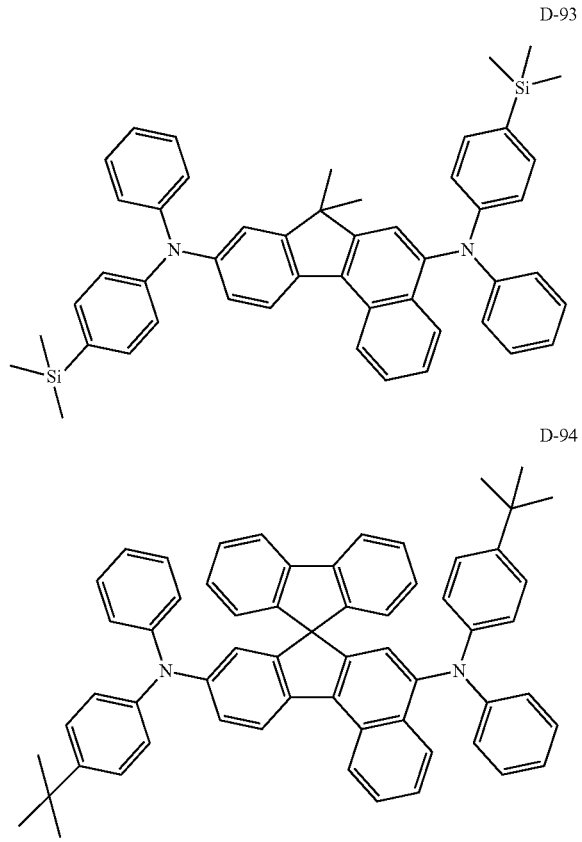
D-97
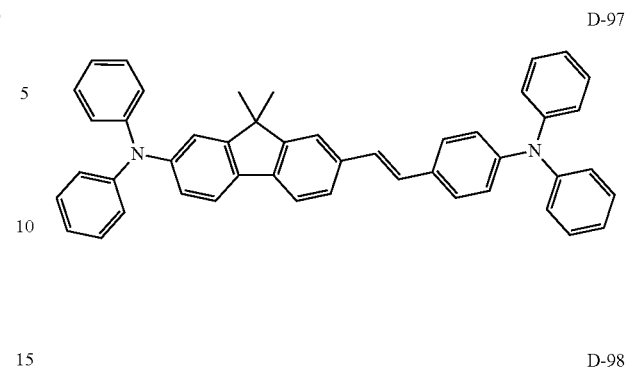
D-98
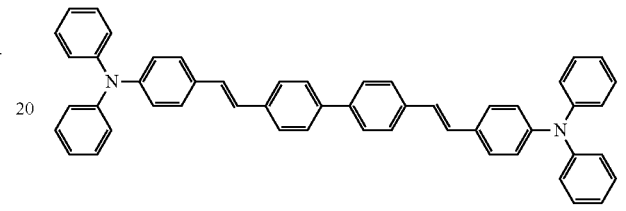
D-99
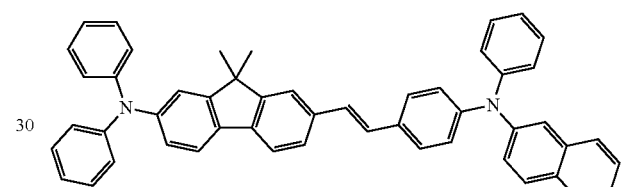
D-94
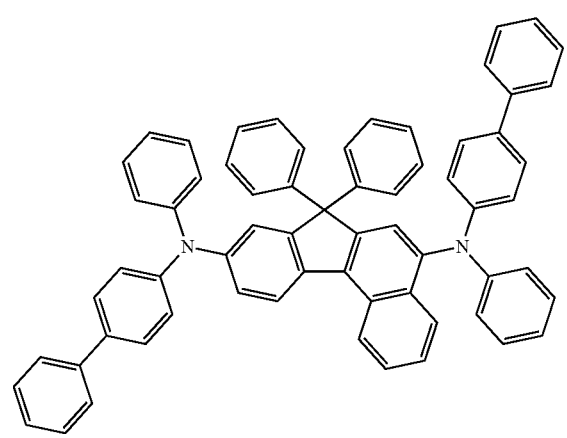
D-100
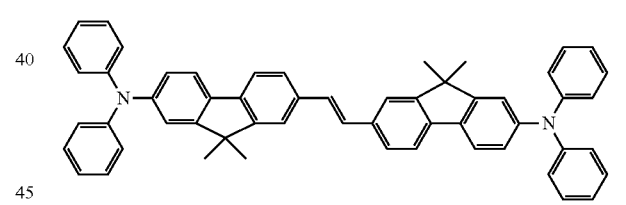
D-101
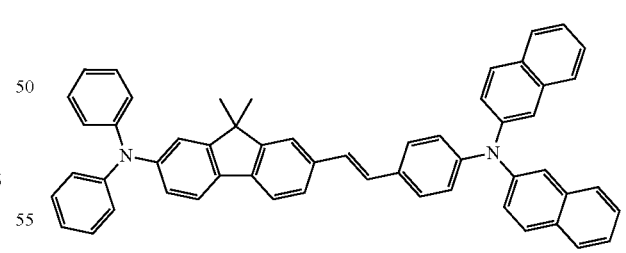
D-95
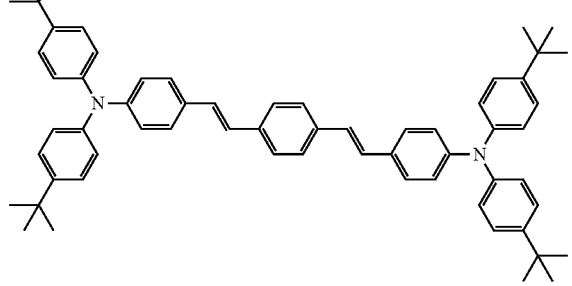
D-102
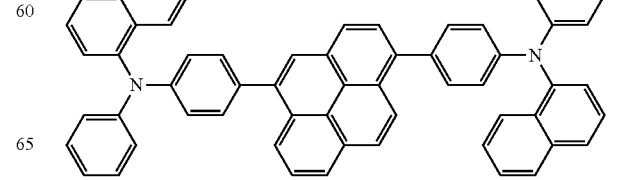
D-96

-continued

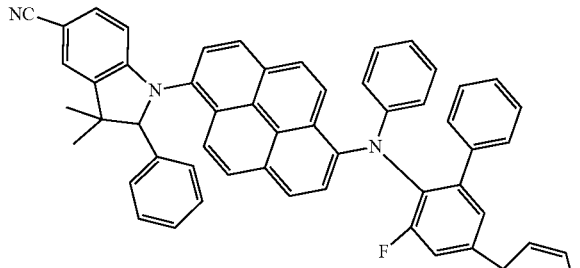
D-103

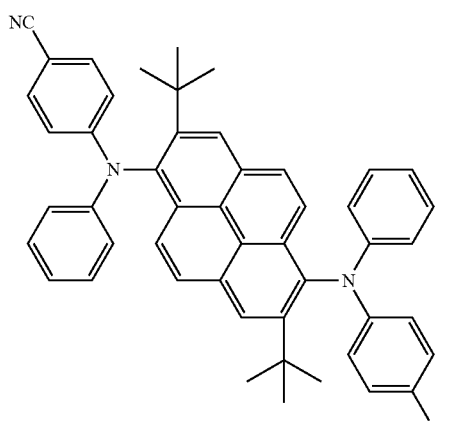
D-104

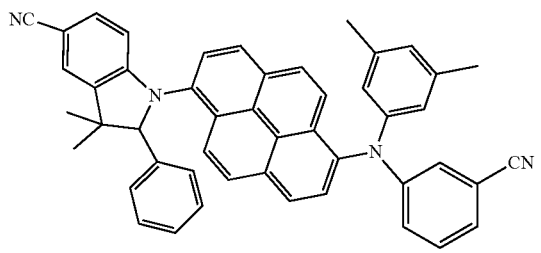
D-105

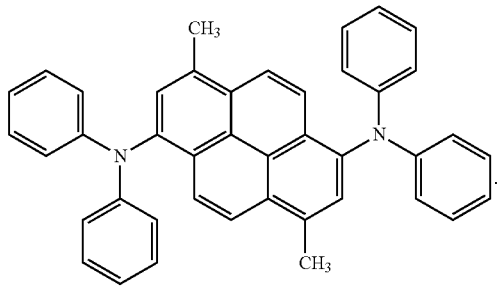
D-106

Also, the present disclosure provides a host material, an electron transport material, or an electron buffer material comprising the organic electroluminescent compound of formula 1.

The electron buffer material refers to a material which controls the flow of charge. Thus, the electron buffer material may be, for example, one trapping electrons, blocking electrons, or lowering the energy barrier between an electron transport zone and a light-emitting layer. In organic electroluminescent devices, the electron buffer material may be used for an electron buffer layer, or may be incorporated in another region such as an electron transport zone or a light-emitting layer, in which the electron buffer layer is placed between a light-emitting layer and an electron transport zone, or between an electron transport zone and a second electrode in the organic electroluminescent devices. The electron buffer material may further include conventional materials generally used for manufacturing organic electroluminescent devices.

Further, if the organic electroluminescent compound of formula 1 is used as an electron transport material, the electron transport material may be composed of the organic electroluminescent compound of formula 1 alone, or may further include conventional materials contained in electron transport materials.

In the organic electroluminescent device according to the present disclosure, the organic layer may further comprise at least one compound selected from the group consisting of arylamine-based compounds and styrylarylamine-based compounds.

In addition, in the organic electroluminescent device according to the present disclosure, the organic layer may further comprise at least one metal selected from the group consisting of metals of Group 1, metals of Group 2, transition metals of the 4th period, transition metals of the $5^{th}$ period, lanthanides and organic metals of d-transition elements of the Periodic Table, or at least one complex compound comprising said metal.

In addition, the organic electroluminescent device according to the present disclosure may emit white light by further comprising at least one light-emitting layer which comprises a blue light-emitting compound, a red light-emitting compound or a green light-emitting compound known in the field, besides the compound according to the present disclosure. Also, if necessary, a yellow or orange light-emitting layer can be further comprised in the device.

In the organic electroluminescent device according to the present disclosure, at least one layer (hereinafter, "a surface layer") is preferably placed on an inner surface(s) of one or both electrode(s); selected from a chalcogenide layer, a metal halide layer, and a metal oxide layer. Specifically, a chalcogenide (including oxides) layer of silicon or aluminum is preferably placed on an anode surface of a light-emitting medium layer, and a metal halide layer or a metal oxide layer is preferably placed on a cathode surface of a light-emitting medium layer. Such a surface layer provides operation stability for the organic electroluminescent device. Preferably, said chalcogenide includes $SiO_x$ ($1 \leq X \leq 2$), $AlO_x$ ($1 \leq X \leq 1.5$) SiON, SiAlON, etc.; said metal halide includes LiF, $MgF_2$, $CaF_2$, a rare earth metal fluoride, etc.; and said metal oxide includes $Cs_2O$, $Li_2O$, MgO, SrO, BaO, CaO, etc.

A hole injection layer, a hole transport layer, an electron blocking layer, or a combination thereof can be used between the anode and the light-emitting layer. The hole injection layer may be multilayers in order to lower the hole injection barrier (or hole injection voltage) from the anode to the hole transport layer or the electron blocking layer, wherein each of the multilayers may use two compounds simultaneously. The hole transport layer or the electron blocking layer may also be multilayers.

An electron buffer layer, a hole blocking layer, an electron transport layer, an electron injection layer, or a combination thereof can be used between the light-emitting layer and the cathode. The electron buffer layer may be multilayers in order to control the injection of the electron and improve the interfacial properties between the light-emitting layer and the electron injection layer, wherein each of the multilayers may use two compounds simultaneously. The hole blocking layer or the electron transport layer may also be multilayers, wherein each of the multilayers may use a plurality of compounds.

The light-emitting auxiliary layer may be placed between the anode and the light-emitting layer, or between the cathode and the light-emitting layer. When the light-emitting auxiliary layer is placed between the anode and the light-emitting layer, it can be used for promoting the hole injection and/or hole transport, or for preventing the overflow of electrons. When the light-emitting auxiliary layer is placed between the cathode and the light-emitting layer, it can be used for promoting the electron injection and/or electron transport, or for preventing the overflow of holes. Also, the hole auxiliary layer may be placed between the hole transport layer (or hole injection layer) and the light-emitting layer, and may be effective to promote or block the hole transport rate (or hole injection rate), thereby enabling the charge balance to be controlled. Further, the electron blocking layer may be placed between the hole transport layer (or hole injection layer) and the light-emitting layer, and can confine the excitons within the light-emitting layer by blocking the overflow of electrons from the light-emitting layer to prevent a light-emitting leakage. When an organic electroluminescent device includes two or more hole transport layers, the hole transport layer, which is further included, may be used as a hole auxiliary layer or an electron blocking layer. The hole auxiliary layer and the electron blocking layer may have an effect of improving the efficiency and/or the lifespan of the organic electroluminescent device.

Preferably, in the organic electroluminescent device of the present disclosure, a mixed region of an electron transport compound and a reductive dopant, or a mixed region of a hole transport compound and an oxidative dopant may be placed on at least one surface of a pair of electrodes. In this case, the electron transport compound is reduced to an anion, and thus it becomes easier to inject and transport electrons from the mixed region to the light-emitting medium. Furthermore, the hole transport compound is oxidized to a cation, and thus it becomes easier to inject and transport holes from the mixed region to the light-emitting medium. Preferably, the oxidative dopant includes various Lewis acids and acceptor compounds; and the reductive dopant includes alkali metals, alkali metal compounds, alkaline earth metals, rare-earth metals, and mixtures thereof. The reductive dopant layer may be employed as a charge-generating layer to prepare an organic electroluminescent device having two or more light-emitting layers which emits white light.

In order to form each layer constituting the organic electroluminescent device of the present disclosure, dry film-forming methods such as vacuum deposition, sputtering, plasma, ion plating methods, etc., or wet film-forming methods such as spin coating, dip coating, flow coating methods, etc., can be used. When forming the film of the first and second host compounds of the present disclosure, a co-evaporation or a mixed evaporation method is used.

When using a wet film-forming method, a thin film is formed by dissolving or dispersing the material constituting each layer in suitable solvents, such as ethanol, chloroform, tetrahydrofuran, dioxane, etc. The solvents are not specifically limited as long as the material constituting each layer is soluble or dispersible in the solvents, which do not cause any problems in forming a film.

By using the organic electroluminescent device of the present disclosure, a display device, for example, for smartphones, tablets, notebooks, PCs, TVs, or vehicles, or a lighting device, for example, an indoor or outdoor lighting device, can be produced.

Hereinafter, the preparation method of the organic electroluminescent compounds of the present disclosure, the physical properties of the compounds, and the luminous properties of the organic electroluminescent device comprising the compounds will be explained in detail with reference to the representative compounds of the present disclosure. However, the present disclosure is not limited to the Examples below.

EXAMPLE 1: PREPARATION OF COMPOUND C-6

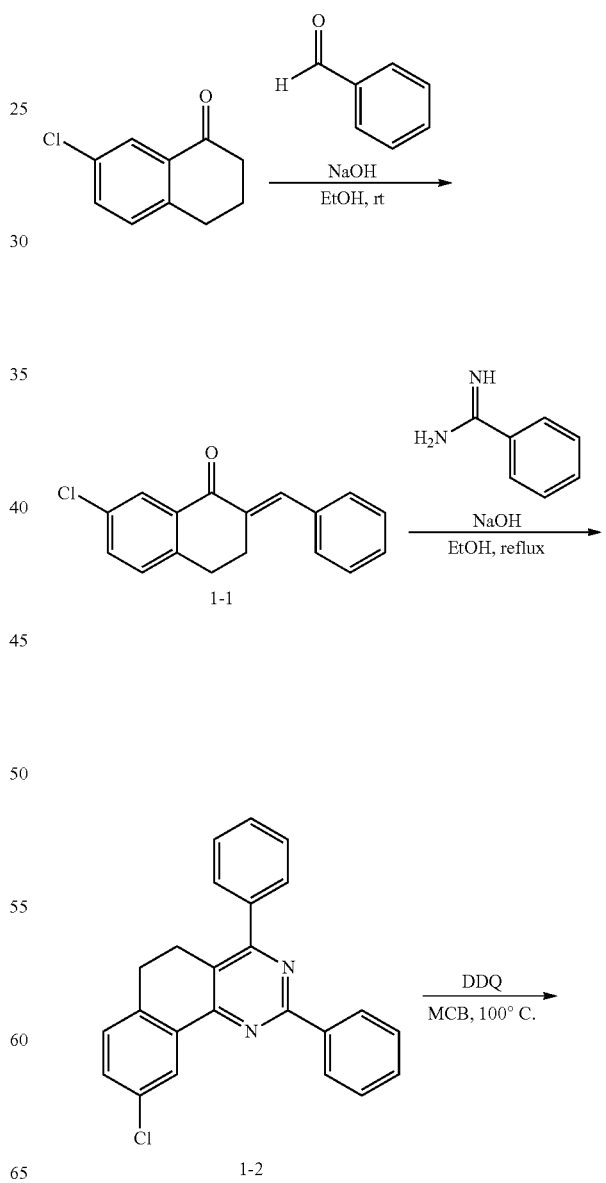

-continued

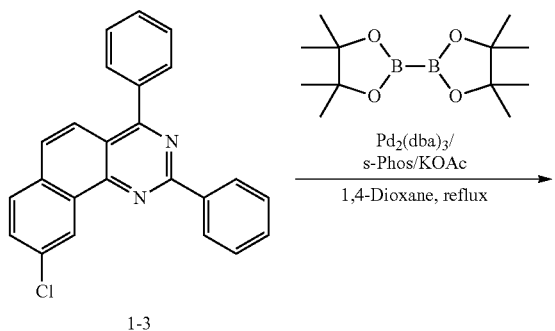

1-3

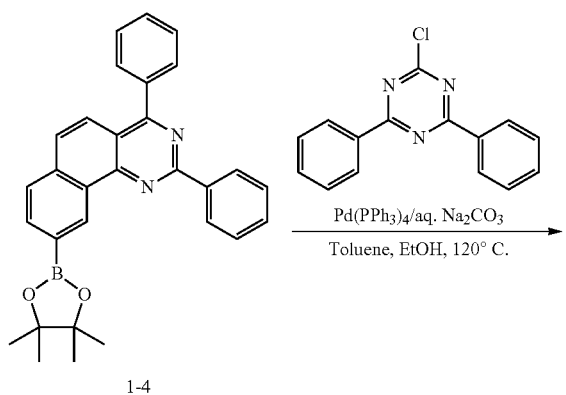

1-4

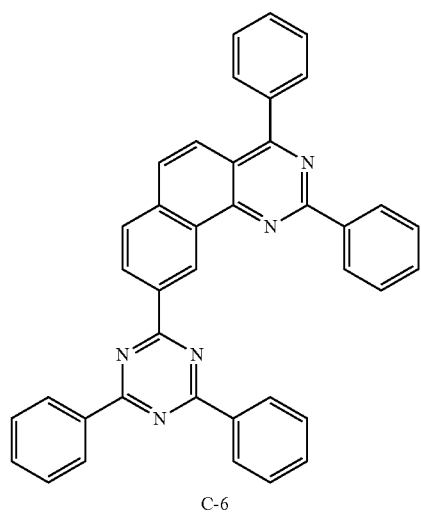

C-6

Preparation of Compound 1-1

20 g of 7-chloro-3,4-dihydronaphthalen-1(2H)-one (110.72 mmol), 13 g of benzaldehyde (121.80 mmol), 6.6 g of sodium hydroxide (166.08 mmol), and 360 mL of ethanol were introduced into a reaction vessel and stirred at room temperature for 2 hours. After completion of the reaction, the resulting solid was filtered and washed with ethanol to obtain 25.2 g of compound 1-1 (yield: 85%).

Preparation of Compound 1-2

25.2 g of compound 1-1 (93.77 mmol), 16.2 g of benzimidamide (103.15 mmol), 6.8 g of sodium hydroxide (281.31 mmol), and 312 mL of ethanol were introduced into a reaction vessel and stirred for 20 hours under reflux. After completion of the reaction, the resulting solid was filtered and washed with ethanol to obtain 34.5 g of compound 1-2 (yield: 100%).

Preparation of Compound 1-3

34.5 g of compound 1-2 (93.77 mmol), 43 g of 2,3-dichloro-5,6-dicyano-1,4-benzoquinone (DDQ) (189.77 mmol), and 474 mL of chlorobenzene (MCB) were introduced into a reaction vessel and stirred for 18 hours under reflux. After completion of the reaction, the resulting product was washed with distilled water and extracted with ethyl acetate. The extracted organic layer was then dried with magnesium sulfate and the solvent was removed by a rotary evaporator. The residue was purified by column chromatography to obtain 15.5 g of compound 1-3 (yield: 45%).

Preparation of Compound 1-4

15.5 g of compound 1-3 (42.25 mmol), 12.9 g of bis(pinacolato)diborane (50.70 mmol), 1.6 g of tris(dibenzylideneacetone)dipalladium (1.69 mmol), 1.4 g of 2-dicyclohexylphosphino-2',6'-dimethoxybiphenyl (s-phos) (3.38 mmol), 12.4 g of potassium acetate (126.75 mmol), and 210 mL of 1,4-dioxane were introduced into a reaction vessel and stirred at 130° C. for 6 hours under reflux. After completion of the reaction, the resulting product was cooled to room temperature and extracted with ethyl acetate. The extracted organic layer was then dried with magnesium sulfate and the solvent was removed by a rotary evaporator. The residue was purified by column chromatography to obtain 14 g of compound 1-4 (yield: 72%).

Preparation of Compound C-6

5 g of compound 1-4 (10.9 mmol), 3.2 g of 2-chloro-4,6-diphenyltriazine (12 mmol), 0.4 g of tetrakis(triphenylphosphine)palladium (0.33 mmol), 2.9 g of sodium carbonate (27.28 mmol), 55 mL of toluene, 14 mL of ethanol, and 14 mL of distilled water were introduced into a reaction vessel and stirred at 120° C. for 4 hours. After completion of the reaction, the precipitated solid was washed with distilled water and methanol. The residue was purified by column chromatography to obtain 5 g of compound C-6 (yield: 82%).

| | MW | UV | PL | M.P. |
|---|---|---|---|---|
| C-6 | 563.66 | 340 nm | 411 nm | 314° C. |

EXAMPLE 2: PREPARATION OF COMPOUND C-36

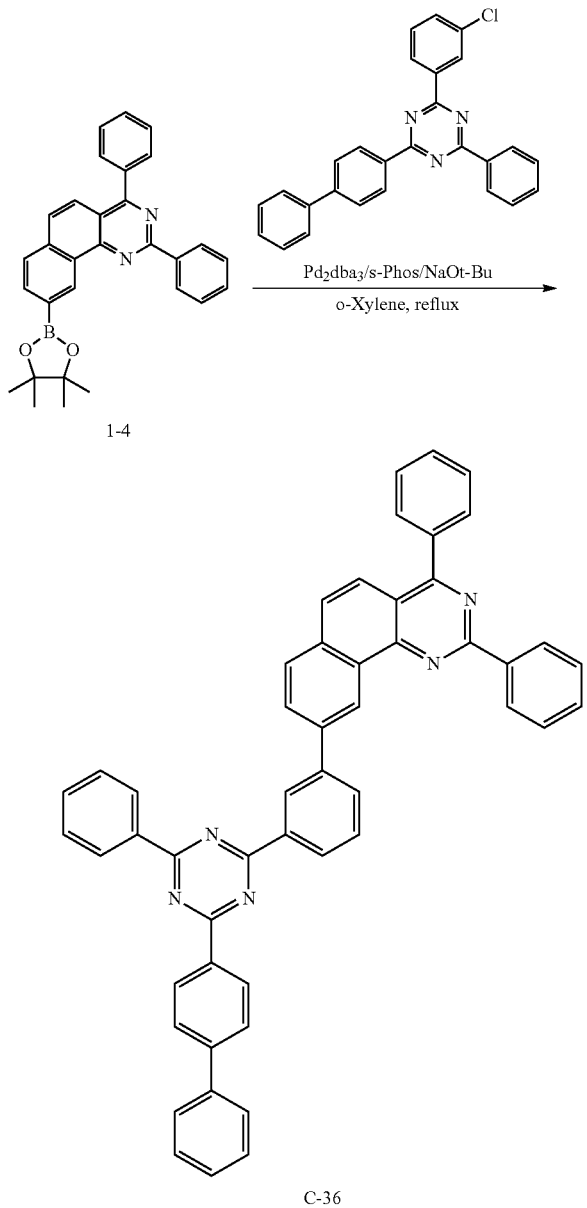

C-36

3.2 g of compound 1-4 (7.0 mmol), 3.2 g of 2-([1,1'-biphenyl]-4-yl)-4-(3-chlorophenyl)-6-phenyl-1,3,5-triazine (7.7 mmol), 0.6 g of tris(dibenzylideneacetone)dipalladium (0.70 mmol), 0.6 g of 2-dicyclohexylphosphino-2',6'-dimethoxybiphenyl (s-phos) (1.40 mmol), 1.0 g of sodium tert-butoxide (10.47 mmol), and 35 mL of o-xylene were introduced into a reaction vessel and stirred for 3 hours under reflux. After completion of the reaction, the resulting product was washed with distilled water and extracted with ethyl acetate. The extracted organic layer was then dried with magnesium sulfate and the solvent was removed by a rotary evaporator. The residue was purified by column chromatography to obtain 2 g of compound C-36 (yield: 42%).

| | MW | UV | PL | M.P. |
|---|---|---|---|---|
| C-36 | 715.84 | 344 nm | 419 nm | 336° C. |

EXAMPLE 3: PREPARATION OF COMPOUND C-37

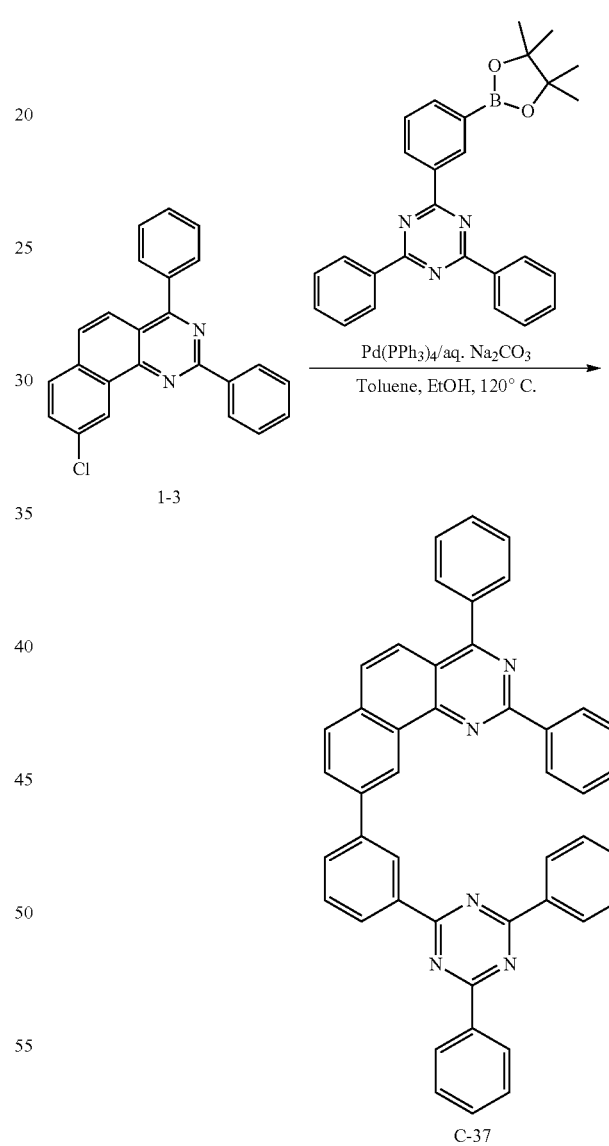

C-37

5 g of compound 1-3 (12 mmol), 5.3 g of 2,4-diphenyl-6-(4,4,5,5-tetramethyl-1,3,2-dioxaboran-2-yl)phenyl)-1,3,5-triazine (12 mmol), 0.4 g of tetrakis(triphenylphosphine) palladium (0.33 mmol), 3.2 g of sodium carbonate (30 mmol), 61 mL of toluene, 15 mL of ethanol, and 15 mL of distilled water were introduced into a reaction vessel and stirred at 120° C. for 4 hours. After completion of the reaction, the precipitated solid was washed with distilled water and methanol. The residue was purified by column chromatography to obtain 3.4 g of compound C-37 (yield: 44%).

|      | MW     | UV     | PL     | M.P.   |
|------|--------|--------|--------|--------|
| C-37 | 639.76 | 334 nm | 419 nm | 323° C.|

Comparative Example 1: Producing a Blue Light-Emitting Oled Device not ACCORDING TO THE PRESENT DISCLOSURE An OLED device not according to the present disclosure was produced as follows: A transparent electrode indium tin oxide (ITO) thin film (10 Ω/sq) on a glass substrate for an OLED (Geomatec Co., Ltd., Japan) was subjected to an ultrasonic washing with acetone and isopropyl alcohol, sequentially, and then was stored in isopropanol. Next, the ITO substrate was mounted on a substrate holder of a vacuum vapor deposition apparatus. Compound HI-1 was introduced into a cell of the vacuum vapor deposition apparatus, and the pressure in the chamber of the apparatus was then controlled to $10^{-7}$ torr. Thereafter, an electric current was applied to the cell to evaporate the introduced material, thereby forming a first hole injection layer having a thickness of 60 nm on the ITO substrate. Compound HI-2 was then introduced into another cell of the vacuum vapor deposition apparatus, and an electric current was applied to the cell to evaporate the introduced material, thereby forming a second hole injection layer having a thickness of 5 nm on the first hole injection layer. Compound HT-1 was introduced into another cell of the vacuum vapor deposition apparatus. Thereafter, an electric current was applied to the cell to evaporate the introduced material, thereby forming a first hole transport layer having a thickness of 20 nm on the second hole injection layer. Compound HT-2 was then introduced into another cell of the vacuum vapor deposition apparatus, and an electric current was applied to the cell to evaporate the introduced material, thereby forming a second hole transport layer having a thickness of 5 nm on the first hole transport layer. After forming the hole injection layers and the hole transport layers, a light-emitting layer was then deposited as follows. Compound H-15 as a host was introduced into one cell of the vacuum vapor deposition apparatus and compound D-38 as a dopant was introduced into another cell of the apparatus. The two materials were evaporated at a different rate and the dopant was deposited in a doping amount of 2 wt %, based on the total weight of the host and dopant, to form a light-emitting layer having a thickness of 20 nm on the second hole transport layer. Next, compound X and compound EIL-1 were evaporated in a weight ratio of 1:1 as electron transport materials to form an electron transport layer having a thickness of 35 nm on the light-emitting layer. After depositing compound EI-1 as an electron injection layer having a thickness of 2 nm on the electron transport layer, an Al cathode having a thickness of 80 nm was deposited by another vacuum vapor deposition apparatus on the electron injection layer. Thus, an OLED device was produced. All the materials used for producing the OLED device were purified by vacuum sublimation at $10^{-6}$ torr.

The driving voltage, luminous efficiency, and color coordinates at a luminance of 1 mA/cm², and the time period for the luminance to decrease from 100% to 90% (lifespan; T90) at a luminance of 2,000 nits of the produced OLED device are provided in Table 1 below.

Comparative Examples 2 and 3: Producing a Blue Light-Emitting Oled Device not According to the Present Disclosure In Comparative Examples 2 and 3, OLED devices were produced in the same manner as in Comparative Example 1, except that compounds shown in Table 1 below were used as an electron transport material. The evaluation results of the OLED devices of Comparative Examples 2 and 3 are provided in Table 1 below.

Device Examples 1 and 2: Producing a Blue Light-Emitting Oled Device Comprising the Compound According to the Present Disclosure In Device Examples 1 and 2, OLED devices were produced in the same manner as in Comparative Example 1, except that compounds shown in Table 1 below were used as an electron transport material. The evaluation results of the OLED devices of Device Examples 1 and 2 are provided in Table 1 below.

TABLE 1

|                       | Electron Transport Material | Driving Voltage (V) | Luminous Efficiency (cd/A) | Color Coordinate (x) | Color Coordinate (y) | Lifespan T90 (hr) |
|-----------------------|------------------|-------|------|-------|-------|------|
| Comparative Example 1 | Compound X       | 3.2   | 4.1  | 0.139 | 0.086 | 39.0 |
| Comparative Example 2 | Compound Y       | 3.1   | 4.8  | 0.139 | 0.087 | 33.6 |
| Comparative Example 3 | Compound Z       | 3.7   | 2.2  | 0.140 | 0.093 | 5.5  |
| Device Example 1      | C-36             | 3.1   | 5.2  | 0.139 | 0.089 | 42.4 |
| Device Example 2      | C-6              | 3.1   | 5.1  | 0.139 | 0.089 | 60.6 |

It is verified that the OLED devices comprising the compound of the present disclosure as an electron transport material have better lifespan characteristic, while exhibiting driving voltage and luminous efficiency characteristics at equivalent or better levels, compared to the OLED devices comprising the compound of the Comparative Examples.

Comparative Example 4: Producing a Blue Light-Emitting Oled Device not According to the Present Disclosure An OLED device not according to the present disclosure was produced as follows: A transparent electrode indium tin oxide (ITO) thin film (10 Ω/sq) on a glass substrate for an OLED (Geomatec Co., Ltd., Japan) was subjected to an ultrasonic washing with acetone and isopropyl alcohol, sequentially, and then was stored in isopropanol. Next, the ITO substrate was mounted on a substrate holder of a vacuum vapor deposition apparatus. Compound HI-1 was introduced into a cell of the vacuum vapor deposition apparatus, and the pressure in the chamber of the apparatus was then controlled to $10^{-7}$ torr. Thereafter, an electric current was applied to the cell to evaporate the introduced material, thereby forming a first hole injection layer having a thickness of 60 nm on the ITO substrate. Compound HI-2 was then introduced into another cell of the vacuum vapor deposition apparatus, and an electric current was applied to the cell to evaporate the introduced material, thereby forming a second hole injection layer having a thickness of 5 nm on the first hole injection layer. Compound HT-1 was introduced into another cell of the vacuum vapor deposition apparatus. Thereafter, an electric current was applied to the cell to evaporate the introduced material, thereby forming a first hole transport layer having a thickness of 20 nm on the second hole injection layer. Compound HT-2 was then introduced into another cell of the vacuum vapor deposition apparatus, and an electric current was applied to the cell to evaporate the introduced material, thereby forming a second hole transport layer having a thickness of 5 nm on the first hole transport layer. After forming the hole injection layers and the hole transport layers, a light-emitting layer was then deposited as follows. Compound H-15 as a host was introduced into one cell of the vacuum vapor deposition apparatus and compound D-38 as a dopant was introduced into another cell of the apparatus. The two materials were evaporated at a different rate and the dopant was deposited in a doping amount of 2 wt %, based on the total weight of the host and dopant, to form a light-emitting layer having a thickness of 20 nm on the second hole transport layer. Next, compound ET-1 and compound EI-1 were evaporated in a weight ratio of 1:1 as electron transport materials to form an electron transport layer having a thickness of 35 nm on the light-emitting layer. After depositing compound EI-1 as an electron injection layer having a thickness of 2 nm on the electron transport layer, an Al cathode having a thickness of 80 nm was deposited by another vacuum vapor deposition apparatus on the electron injection layer. Thus, an OLED device was produced. All the materials used for producing the OLED device were purified by vacuum sublimation at $10^{-6}$ torr.

Comparative Example 5: Producing a Blue Light-Emitting Oled Device not ACCORDING TO THE PRESENT DISCLOSURE In Comparative Example 5, an OLED device was produced in the same manner as in Comparative Example 4, except that the thickness of an electron transport layer was reduced to 30 nm, and compound Y was inserted as an electron buffer layer having a thickness of 5 nm between the light-emitting layer and the electron transport layer.

Device Examples 3 to 5: Producing a Blue Light-Emitting Oled Device Comprising the Compound of the Present Disclosure In Device Examples 3 to 5, OLED devices were produced in the same manner as in Comparative Example 4, except that the thickness of an electron transport layer was reduced to 30 nm, and each of compounds C-6, C-36, and C-37 was inserted as an electron buffer layer having a thickness of 5 nm between the light-emitting layer and the electron transport layer.

The driving voltage and light emission color at a luminance of 1,000 nits, and the time period for the luminance to decrease from 100% to 90% (lifespan; T90) at a luminance of 2,000 nits of the OLED devices produced in Comparative Examples 4 and 5, and Device Examples 3 to 5 are provided in Table 2 below.

TABLE 2

|  | Electron Buffer Material | Driving Voltage (V) | Light Emission Color | Lifespan T90 (hr) |
| --- | --- | --- | --- | --- |
| Comparative Example 4 | — | 4.4 | Blue | 55.4 |
| Comparative Example 5 | Compound Y | 4.2 | Blue | 46.9 |
| Device Example 3 | C-6 | 4.7 | Blue | 72.0 |
| Device Example 4 | C-36 | 4.6 | Blue | 63.0 |
| Device Example 5 | C-37 | 4.4 | Blue | 56.1 |

It is verified that the OLED devices comprising the compound of the present disclosure as an electron buffer material have better lifespan characteristic compared to the OLED devices which do not contain an electron buffer layer or comprise a conventional material as an electron buffer material.

TABLE 3
Compounds used in Device Examples and Comparative Examples
Hole Injection Layer/
Hole Transport Layer
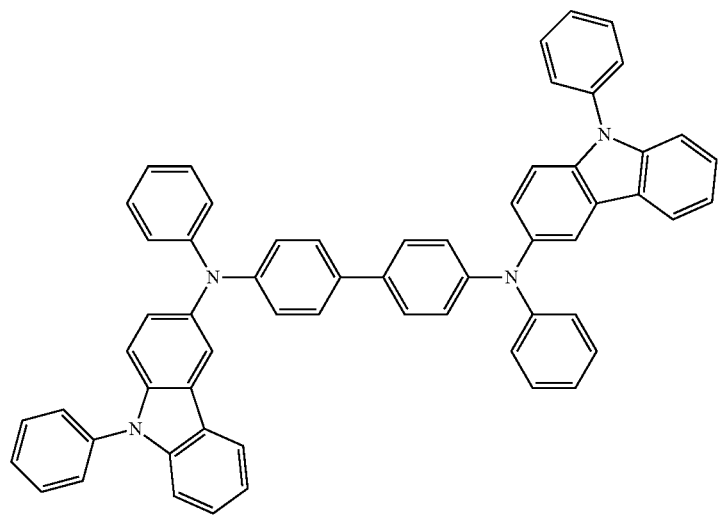
HI-1
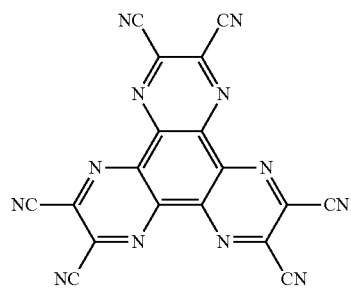
HI-2
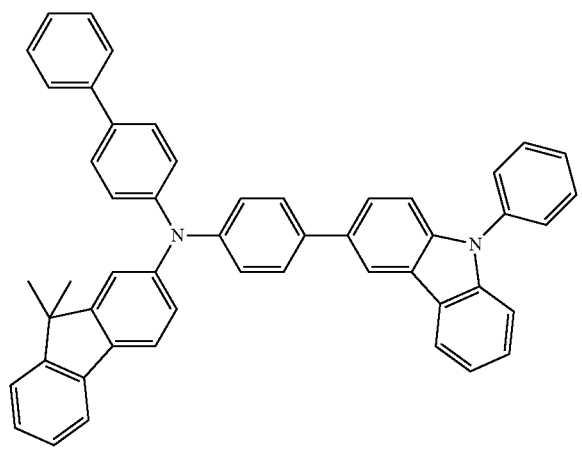
HT-1

TABLE 3-continued
Compounds used in Device Examples and Comparative Examples
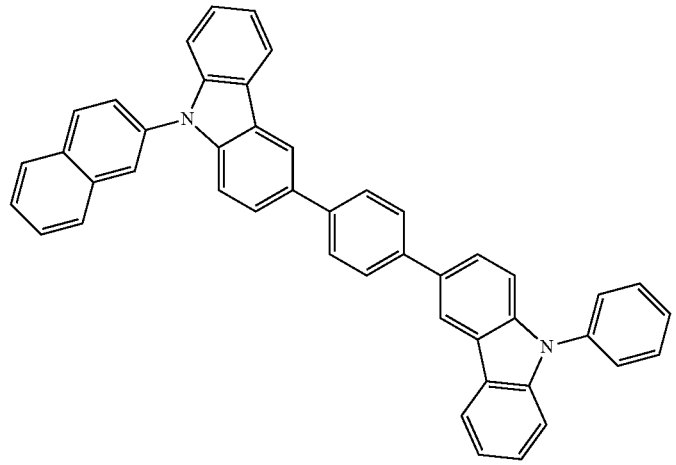
HT-2
Light-Emitting
Layer
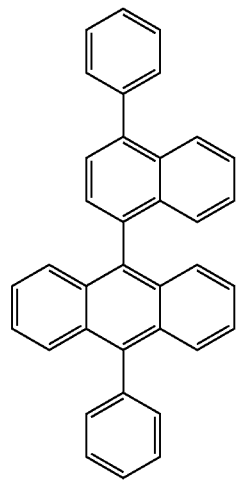
H-15
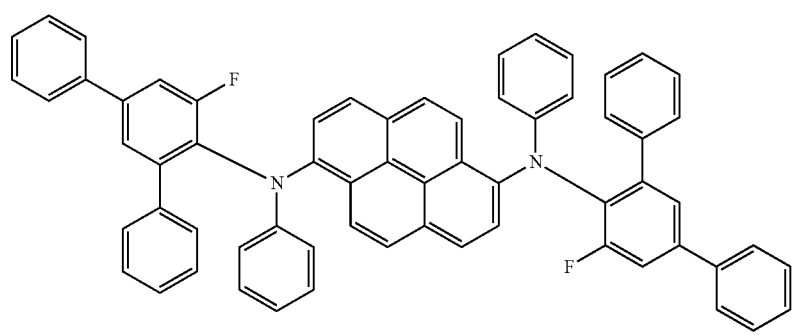
D-38

TABLE 3-continued
Compounds used in Device Examples and Comparative Examples
Electron Buffer Layer/
Electron Transport Layer/
Electron Injection Layer
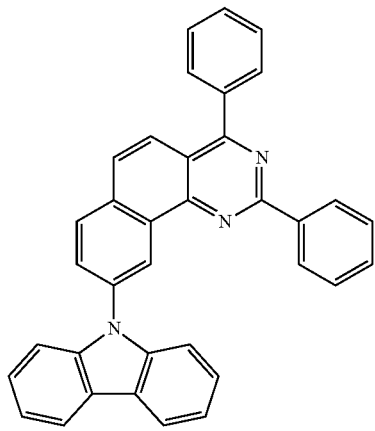
Compound X
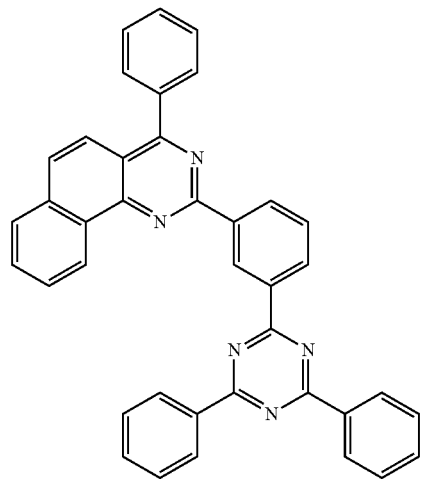
Compound Y
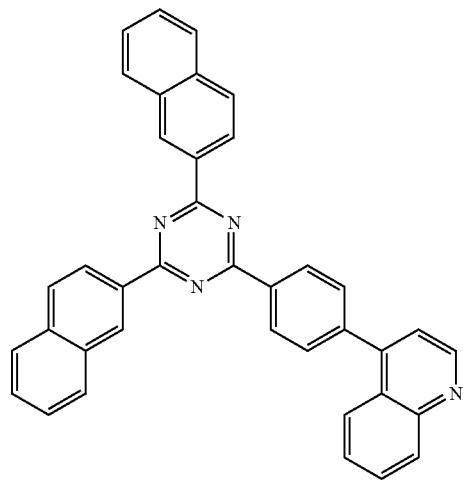
Compound Z TABLE 3-continued
Compounds used in Device Examples and Comparative Examples
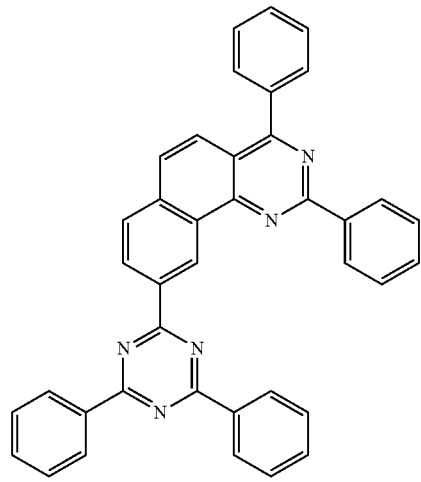
C-6
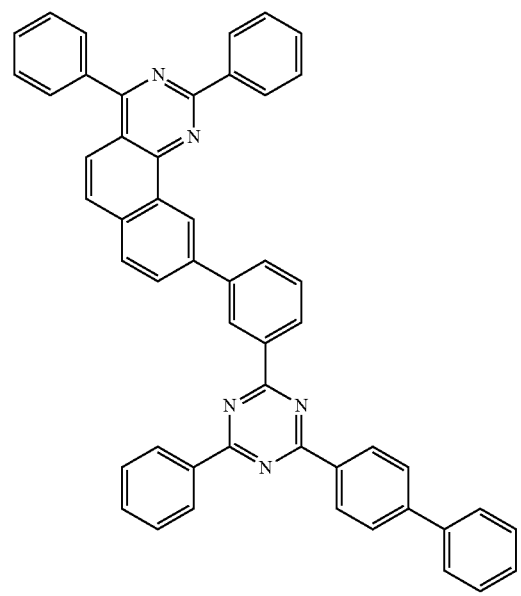
C-36

TABLE 3-continued
Compounds used in Device Examples and Comparative Examples
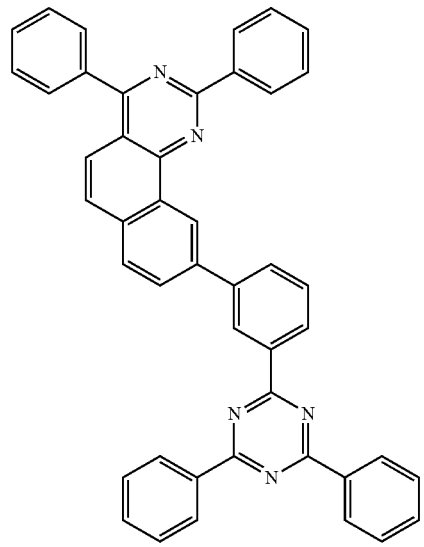
C-37
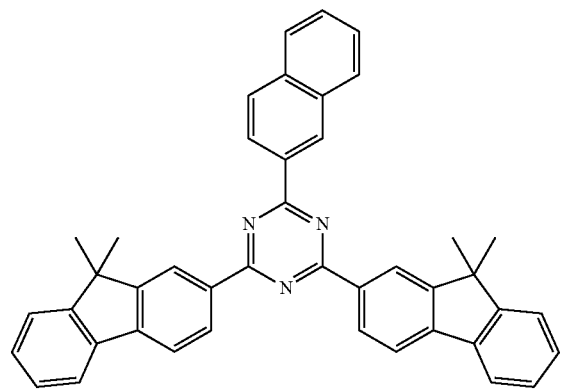
ET-1
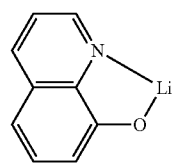
EI-1

The invention claimed is:
1. An organic electroluminescent compound represented by the following formula 1:

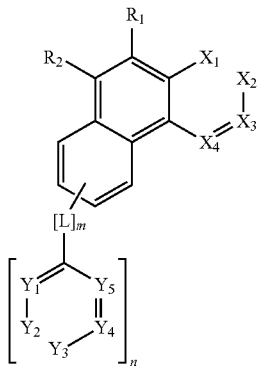

wherein
$X_1$ and $X_3$ represent CR, and $X_2$ and $X_4$ represent N;

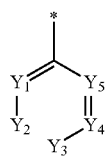

is represented by the following formulas:

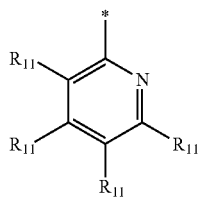

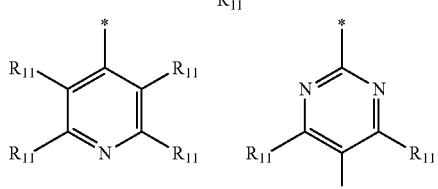

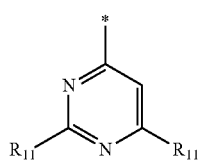

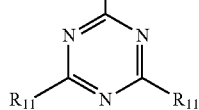

R and $R_{11}$, each independently, represent hydrogen, deuterium, a halogen, a substituted or unsubstituted (C1-C30)alkyl, a substituted or unsubstituted (C6-C30)aryl, or a substituted or unsubstituted (5- to 30-membered) heteroaryl containing at least one heteroatom selected from B, N, O, S, Si, and P;

$R_1$ and $R_2$, each independently, represent hydrogen, deuterium, a halogen, a substituted or unsubstituted (C1-C30)alkyl, a substituted or unsubstituted (C6-C30)aryl, a substituted or unsubstituted (5- to 30-membered) heteroaryl containing at least one heteroatom selected from B, N, O, S, Si, and P, a substituted or unsubstituted (3- to 7-membered)heterocycloalkyl containing at least one heteroatom selected from B, N, O, S, Si, and P, or a substituted or unsubstituted (C3-C30)cycloalkyl; or may be linked to each other to form a substituted or unsubstituted, mono- or polycyclic, (3- to 30-membered) alicyclic or aromatic ring, or a combination thereof, whose carbon atom(s) may be replaced with at least one heteroatom selected from nitrogen, oxygen, and sulfur;

L represents a single bond, or a substituted or unsubstituted (C6-C30)arylene, and, if n is 0, L is not a single bond;

m represents an integer of 0 to 4, n represents an integer of 0 to 2, and m+n is 1 or greater; in which if m and n are 2 or greater, each L and each

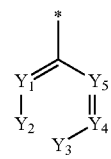

may be the same or different, and, wherein, * represents a bonding site with $(L)_m$.

2. The organic electroluminescent compound according to claim 1, wherein in formula 1, L is represented by the following formulas:

Direct bond

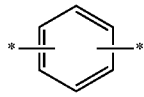

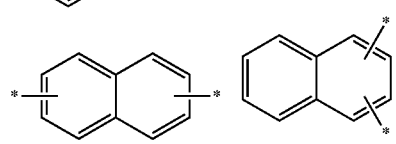

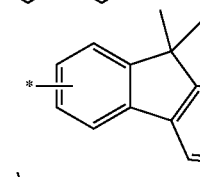

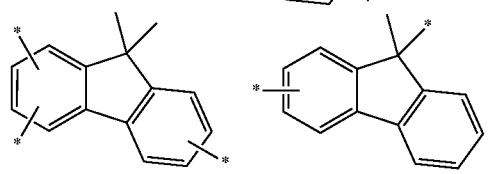

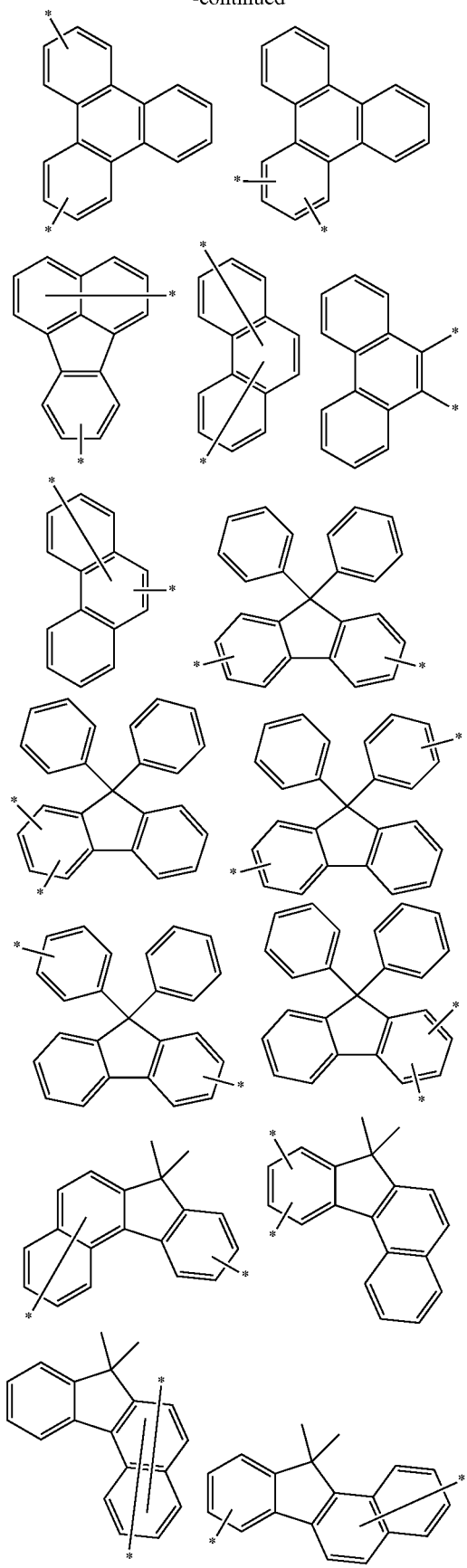

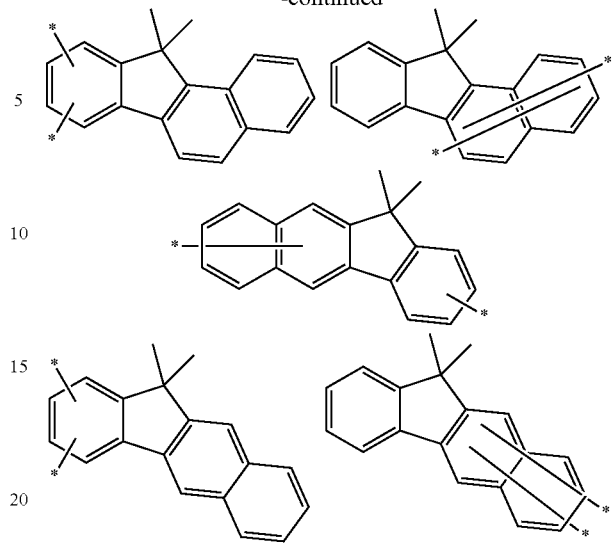

wherein * represents a bonding site.

3. The organic electroluminescent compound according to claim 1, wherein formula 1 is represented by any one of the following formulas 4, and 7:

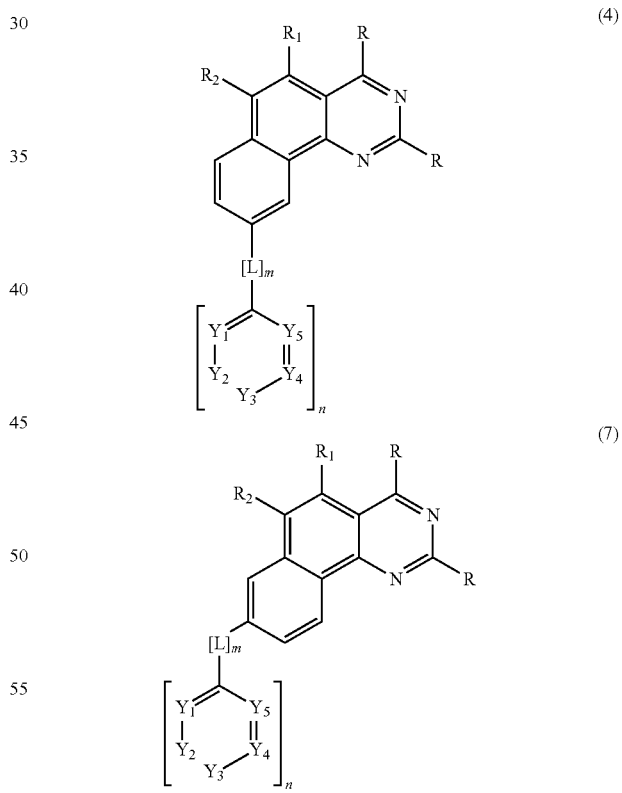

wherein $Y_1$ to $Y_5$, R, $R_1$, $R_2$, L, m, and n are as defined in claim 1.

4. The organic electroluminescent compound according to claim 1, wherein the substituents of the substituted alkyl, the substituted aryl(ene), the substituted heteroaryl(ene), the substituted heterocycloalkyl, the substituted cycloalkyl, and the substituted mono- or polycyclic, alicyclic or aromatic ring, or a combination thereof in R, $R_1$, $R_2$, $R_{11}$, and L, each independently, are at least one selected from the group consisting of deuterium; a halogen; a cyano; a carboxyl; a nitro; a hydroxyl; a (C1-C30)alkyl; a halo(C1-C30)alkyl; a (C2-C30)alkenyl; a (C2-C30)alkynyl; a (C1-C30)alkoxy; a (C1-C30)alkylthio; a (C3-C30)cycloalkyl; a (C3-C30)cycloalkenyl; a (3- to 7-membered)heterocycloalkyl; a (C6-C30)aryloxy; a (C6-C30)arylthio; a (5- to 30-membered) heteroaryl unsubstituted or substituted with a (C6-C30) aryl(s); a (C6-C30)aryl unsubstituted or substituted with a (5- to 30-membered)heteroaryl(s); a tri(C1-C30)alkylsilyl; a tri(C6-C30)arylsilyl; a di(C1-C30)alkyl(C6-C30)arylsilyl; a (C1-C30)alkyldi(C6-C30)arylsilyl; an amino; a mono- or di-(C1-C30)alkylamino; a mono- or di-(C6-C30)arylamino unsubstituted or substituted with a (C1-C30)alkyl(s); a (C1-C30)alkyl(C6-C30)arylamino; a (C1-C30)alkylcarbonyl; a (C1-C30)alkoxycarbonyl; a (C6-C30)arylcarbonyl; a di(C6-C30)arylboronyl; a di(C1-C30)alkylboronyl; a (C1-C30) alkyl(C6-C30)arylboronyl; a (C6-C30)aryl(C1-C30)alkyl; and a (C1-C30)alkyl(C6-C30)aryl.

5. The organic electroluminescent compound according to claim 1, wherein R and $R_{11}$, each independently, represent hydrogen, a substituted or unsubstituted (C6-C25)aryl, or a substituted or unsubstituted (5- to 15-membered)heteroaryl; $R_1$ and $R_2$, each independently, represent hydrogen; and L represents a single bond, a substituted or unsubstituted (C6-C25)aryl(ene), or a substituted or unsubstituted (5- to 20-membered)heteroaryl(ene).

6. The organic electroluminescent compound according to claim 1, wherein R and $R_{11}$, each independently, represent hydrogen, a (C6-C25)aryl unsubstituted or substituted with a (C1-C6)alkyl(s) or a (5- to 15-membered)heteroaryl(s), or a (5- to 15-membered)heteroaryl unsubstituted or substituted with a (C6-C12)aryl(s); $R_1$ and $R_2$, each independently, represent hydrogen; and L represents a single bond, a (C6-C25)aryl(ene) unsubstituted or substituted with a (C1-C6)alkyl(s), or a (5- to 20-membered)heteroaryl(ene) unsubstituted or substituted with a (C6-C12)aryl(s).

7. The organic electroluminescent compound according to claim 1, wherein the compound represented by formula 1 is at least one selected from the group consisting of:

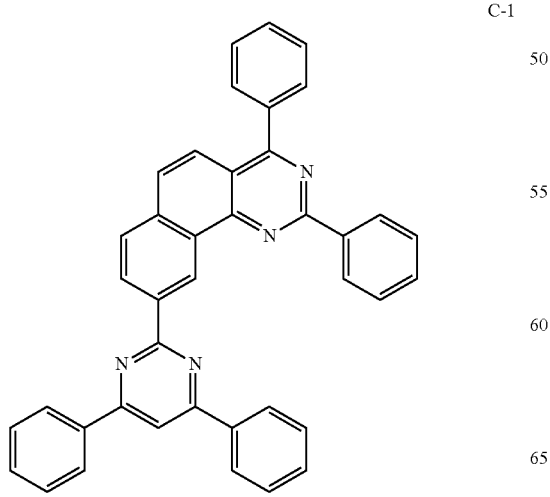

C-1

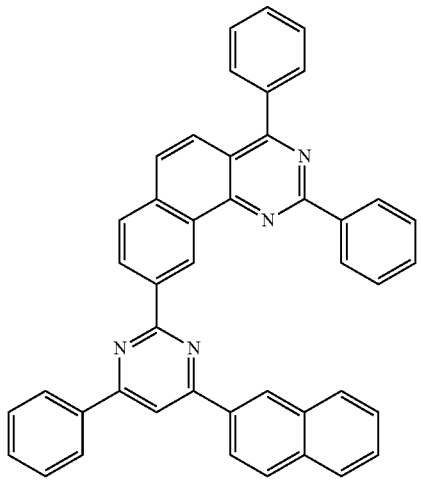

C-2

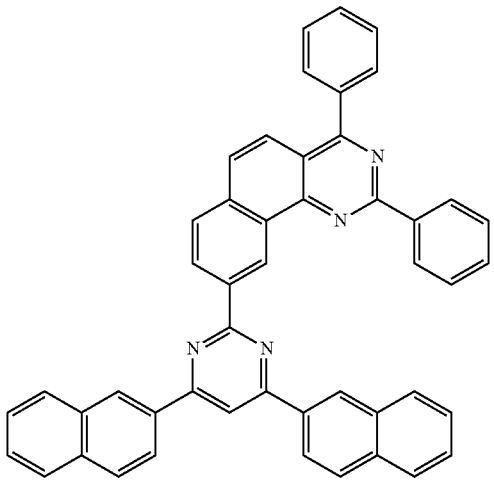

C-3

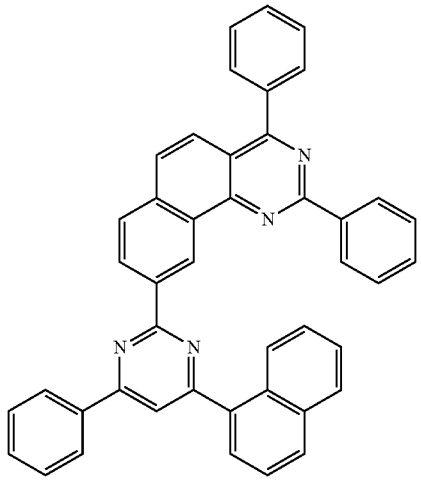

C-4

C-5
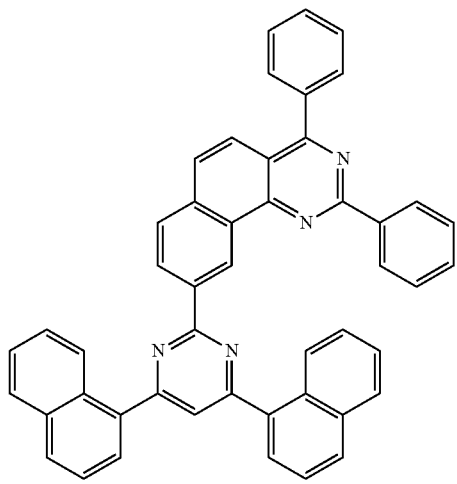
C-6
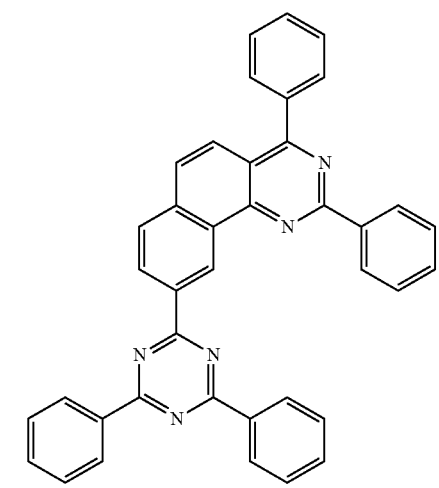
C-7
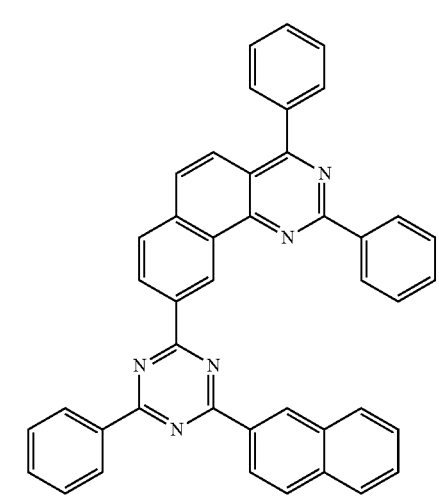
C-8
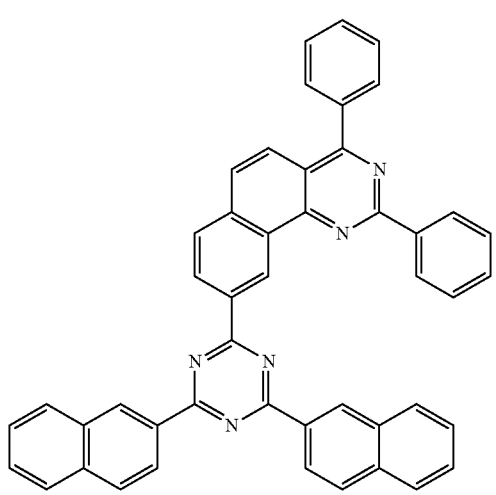
C-9
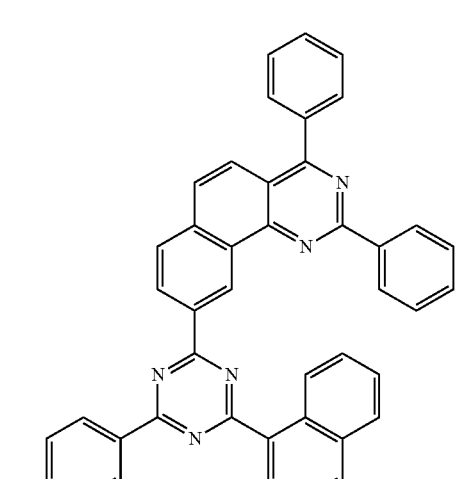
C-10
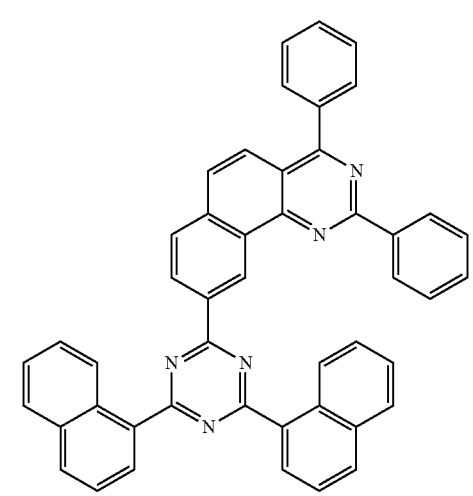

C-11
C-12
C-13
C-14
C-15
C-16
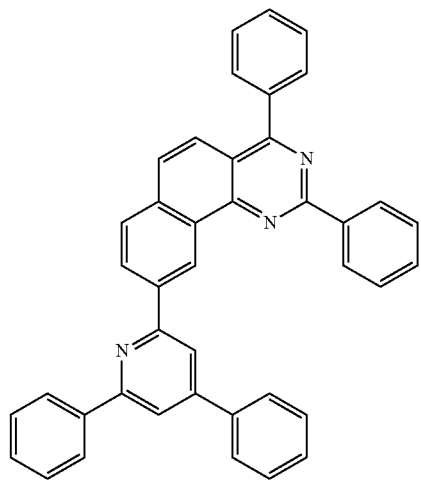
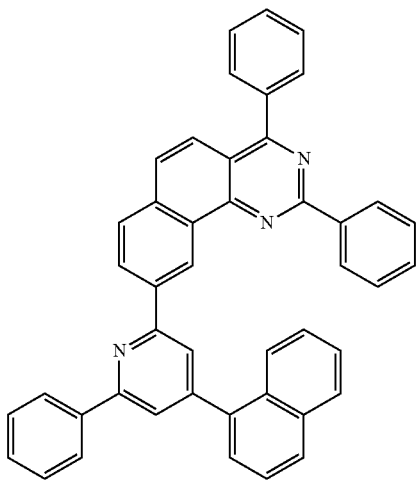

-continued
C-17
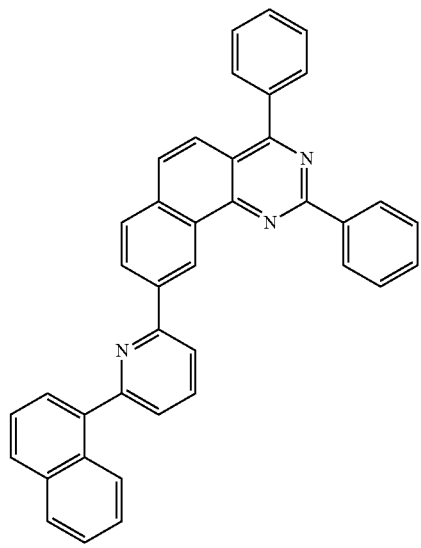
C-18
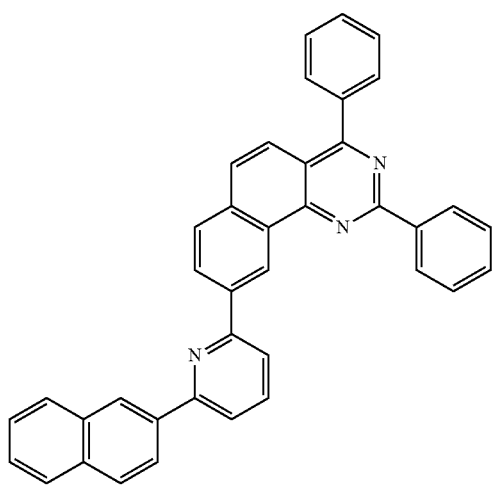
C-19
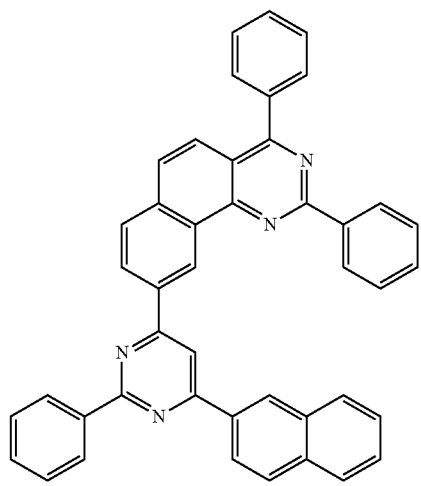
-continued
C-20
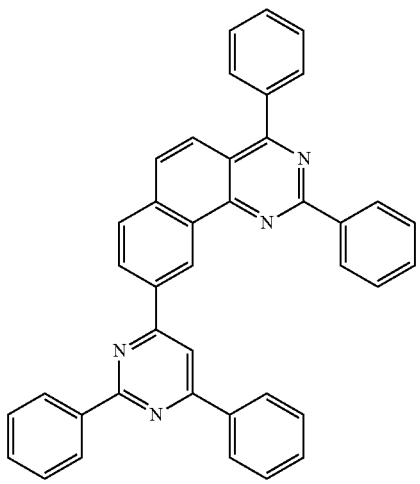
C-21
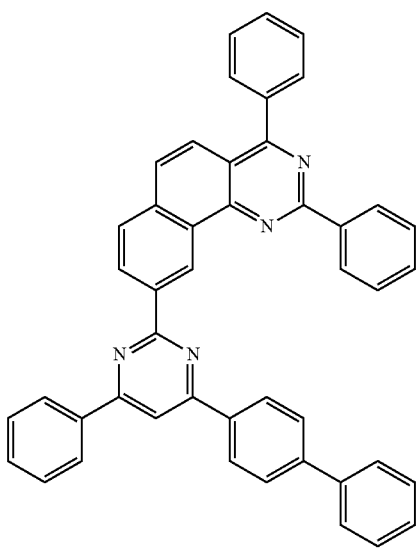
C-22
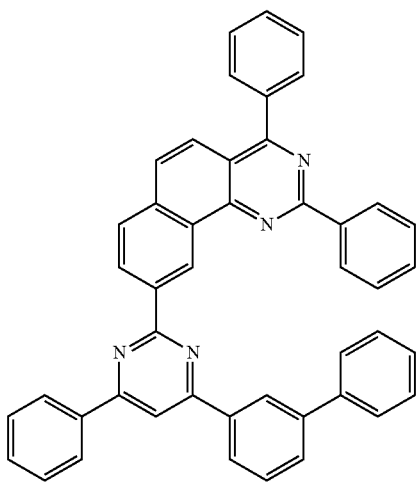

C-23
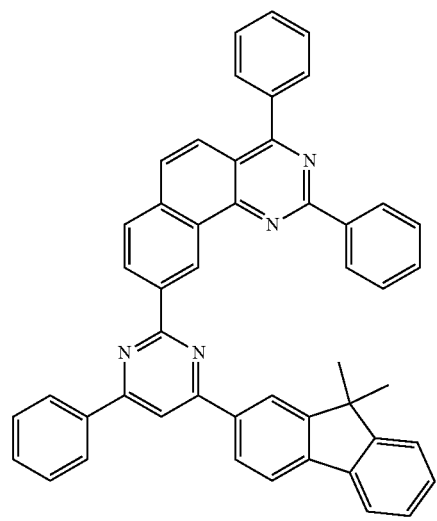
C-24
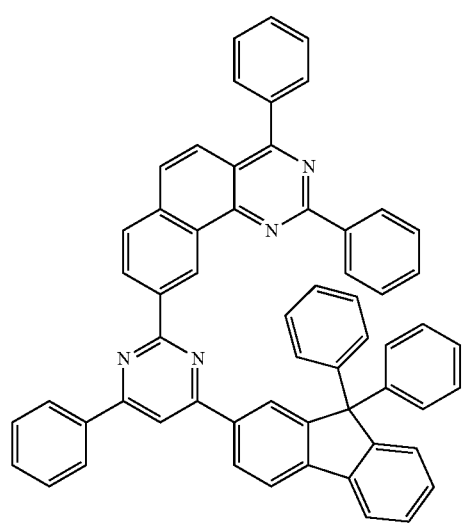
C-25
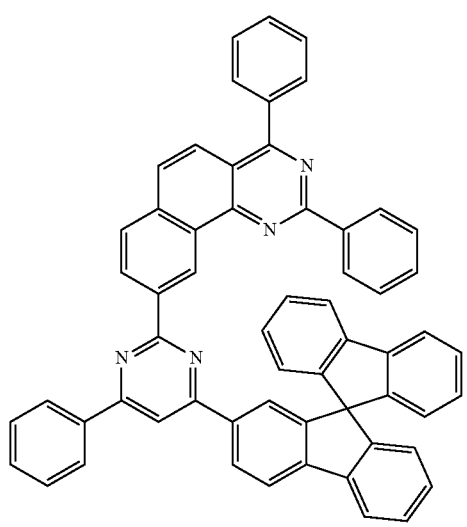
C-26
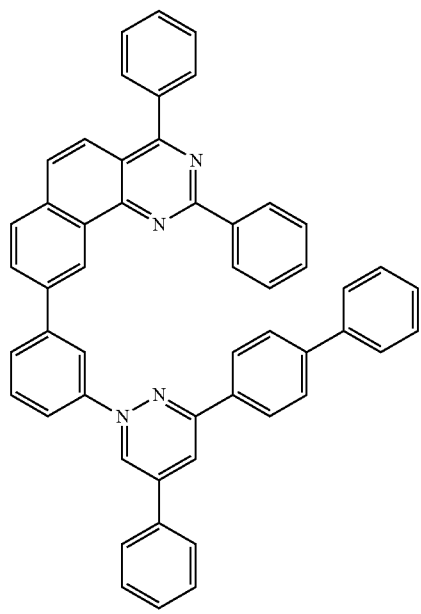
C-27
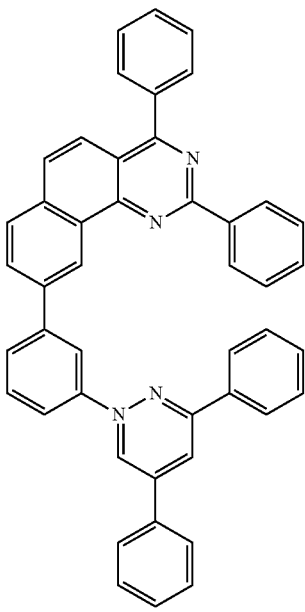

C-28
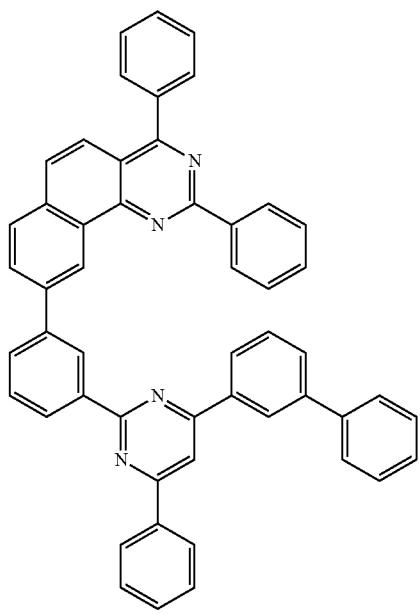
C-29
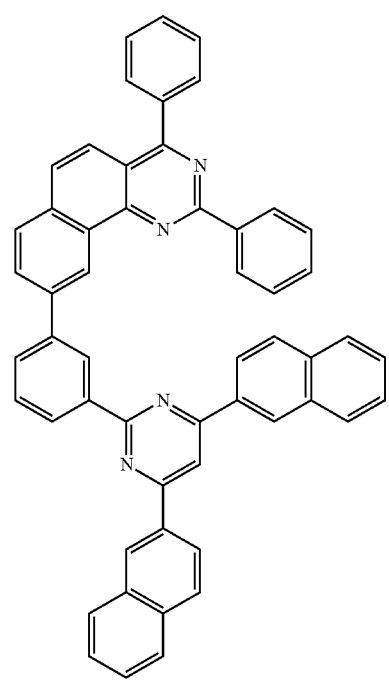
C-30
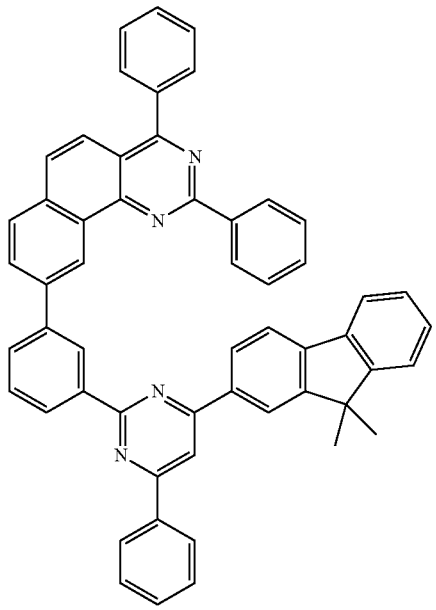
C-31
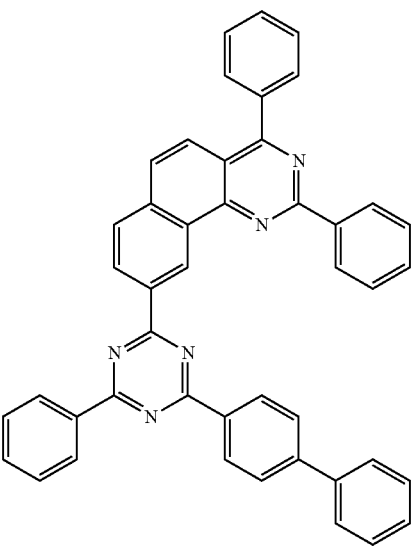
C-32
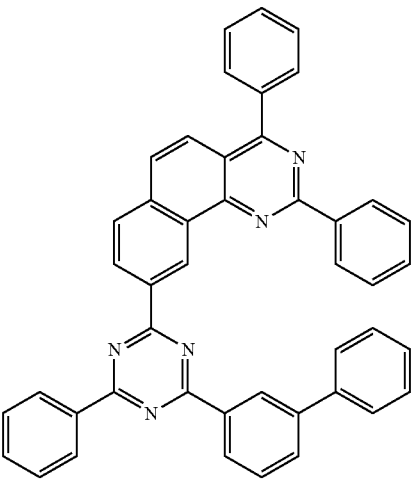

C-33
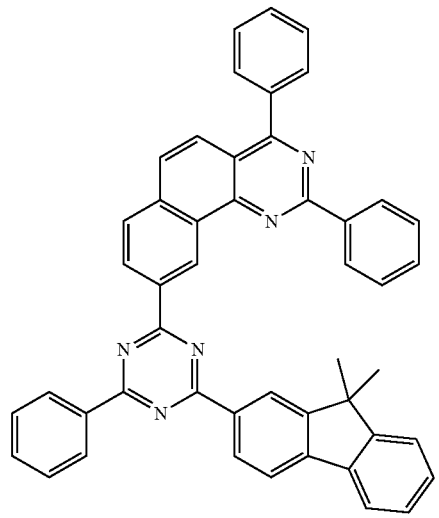
C-36
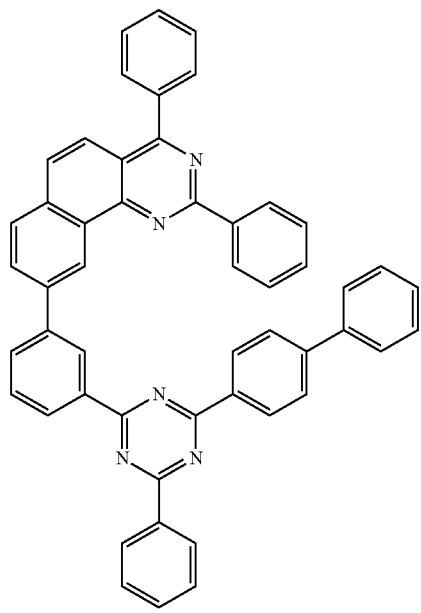
C-34
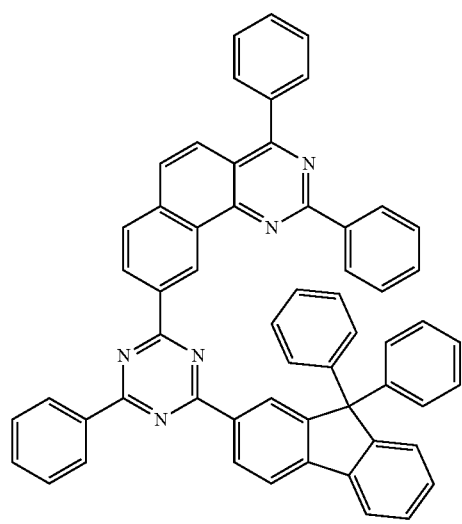
C-35
C-37
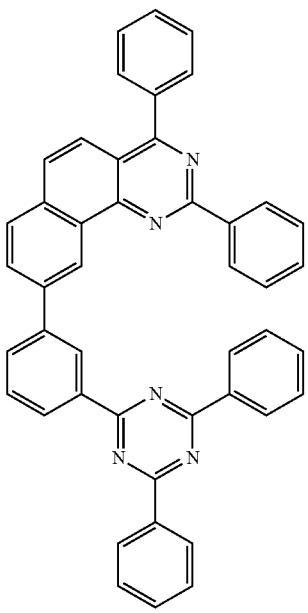

C-38
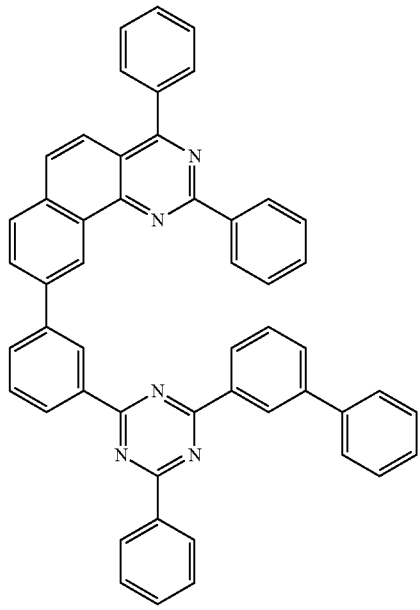
C-40
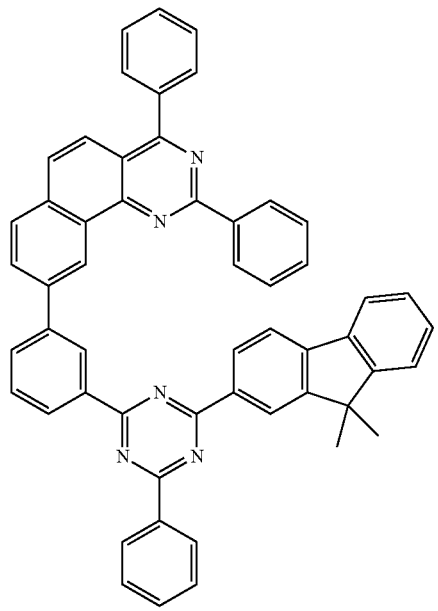
C-39
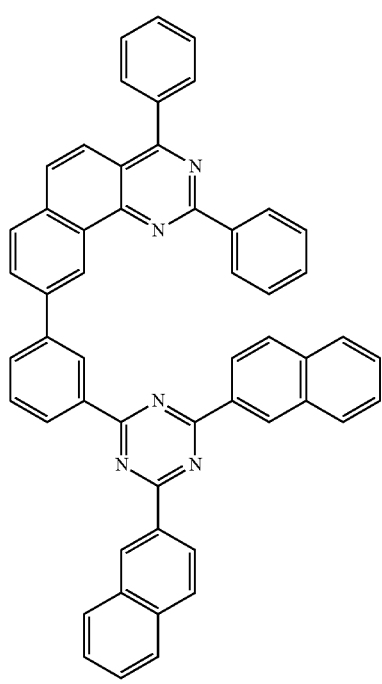
C-41
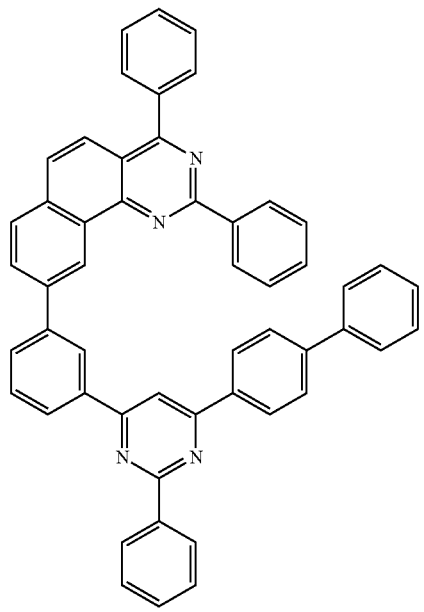

C-42
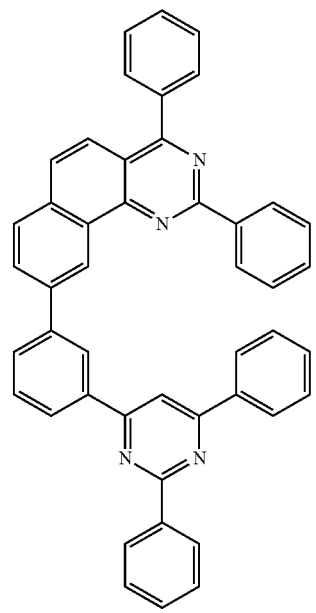
C-45
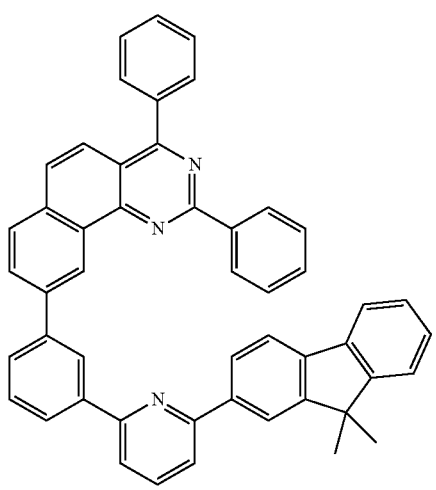
C-43
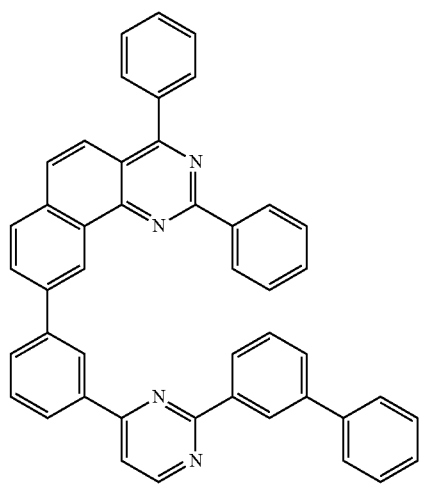
C-46
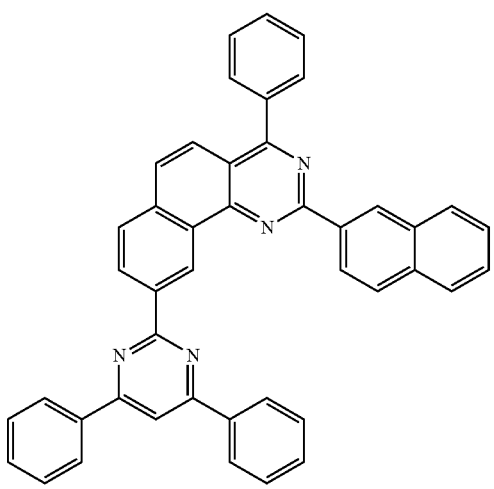
C-44
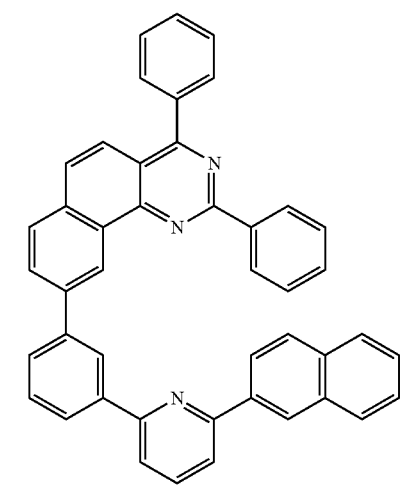
C-47
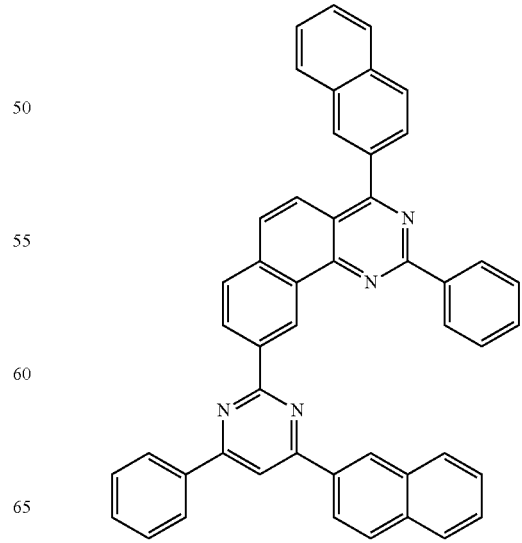

C-48
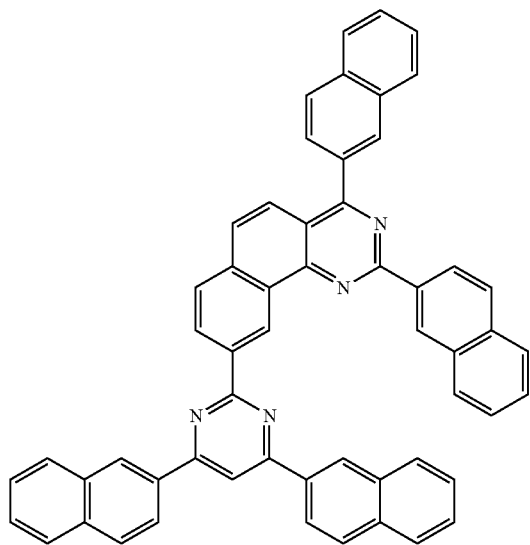
C-49
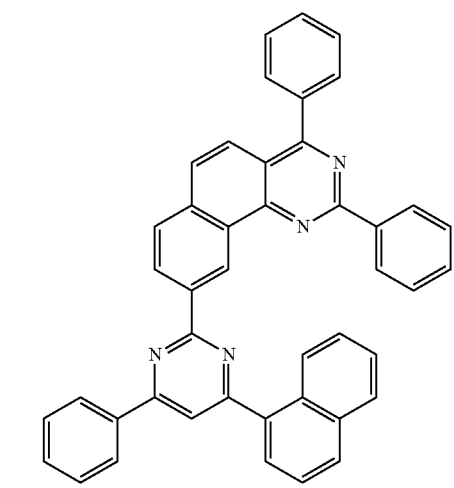
C-50
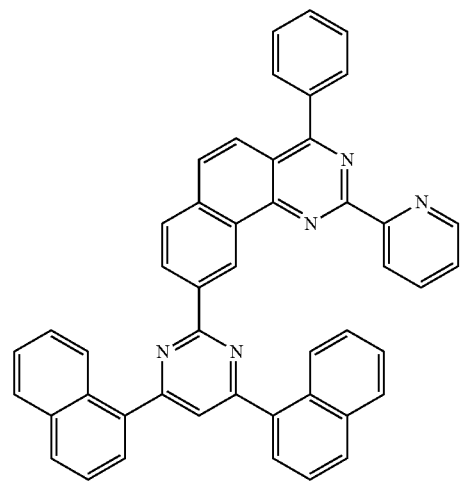
C-51
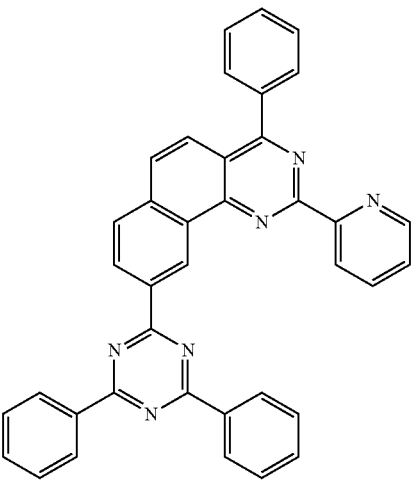
C-52
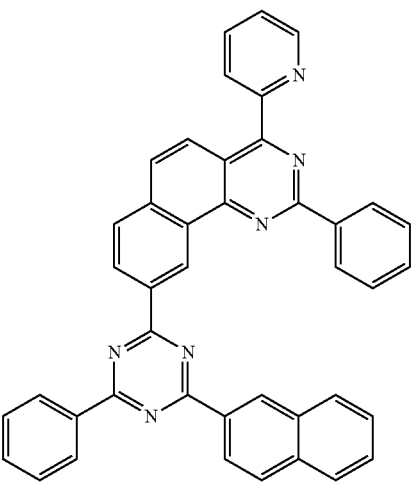
C-53
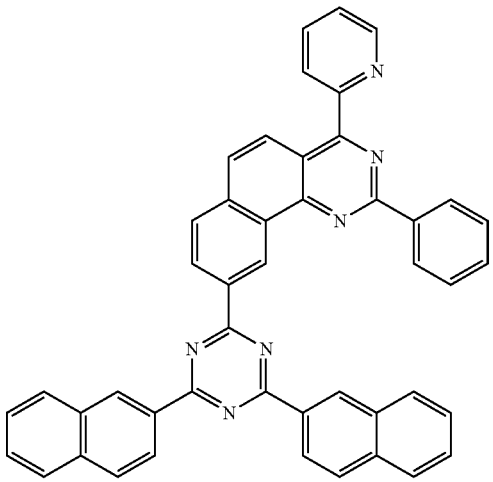

-continued
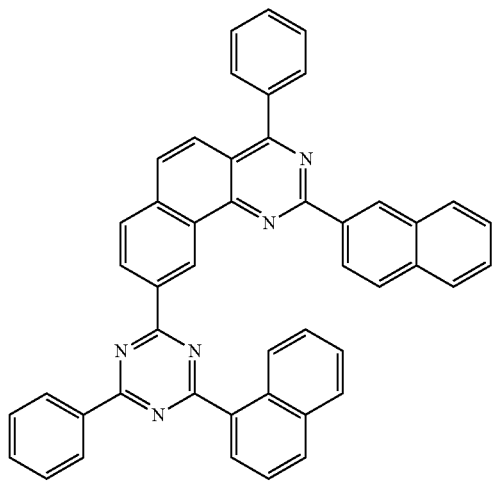
C-54
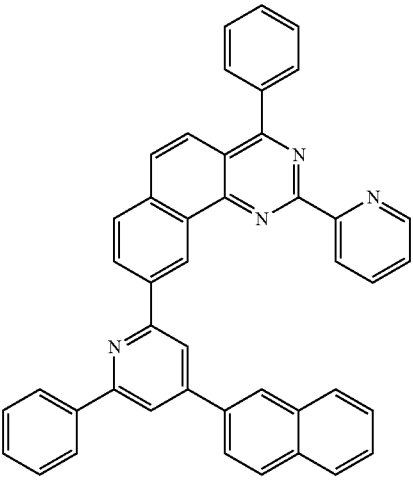
C-57
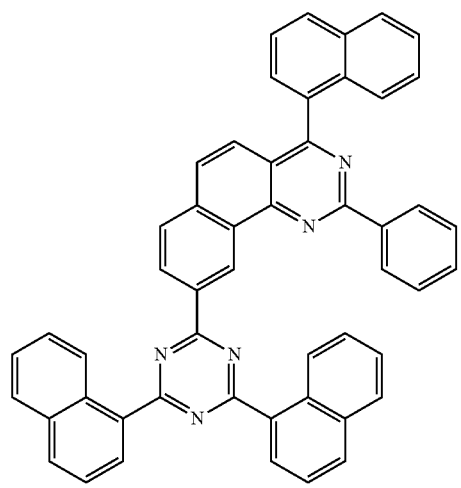
C-55
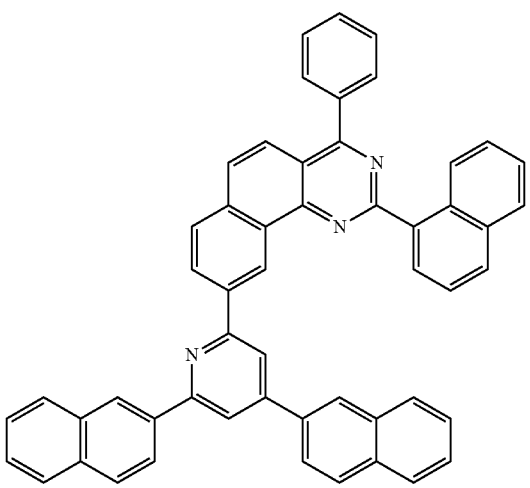
C-58
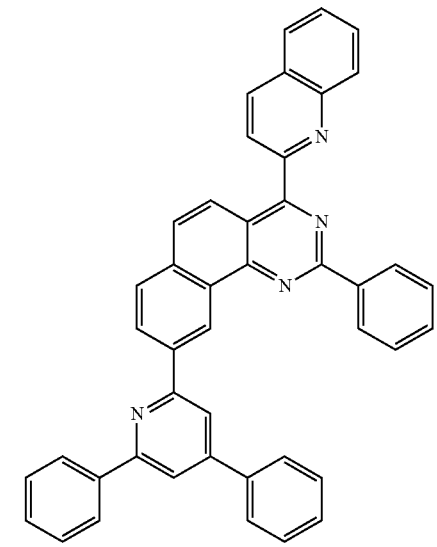
C-56
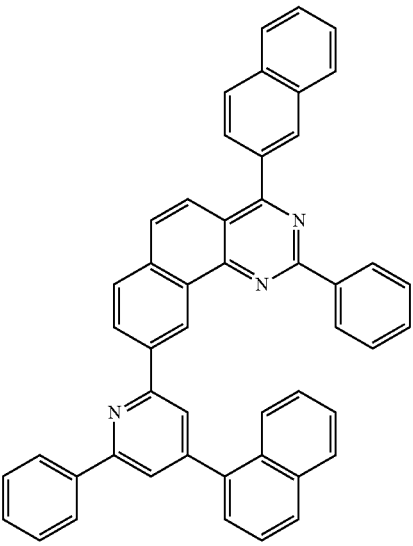
C-59

C-60
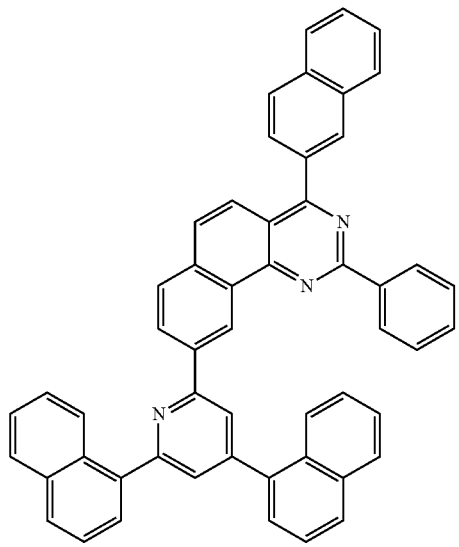
C-61
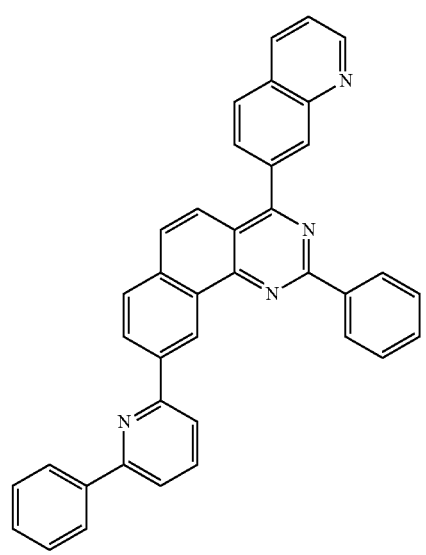
C-62
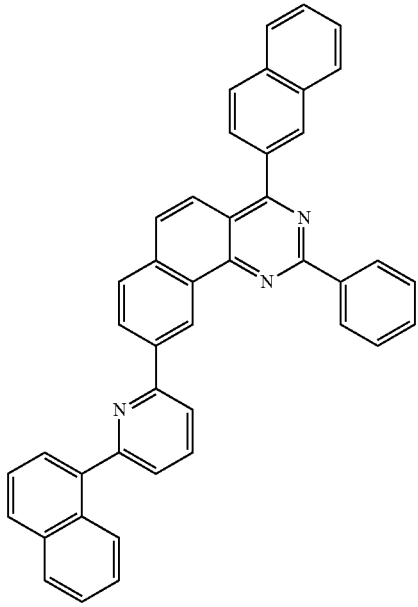
C-63
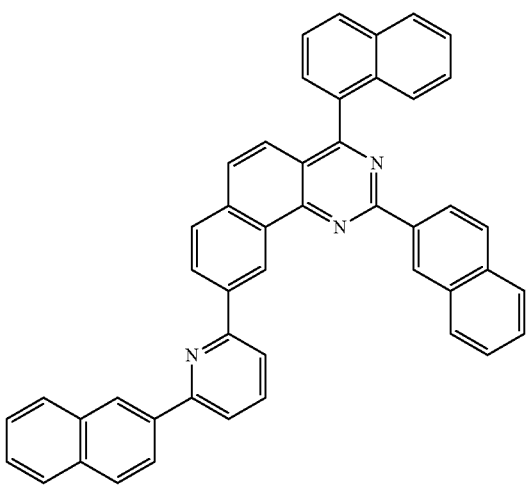
C-64

C-65 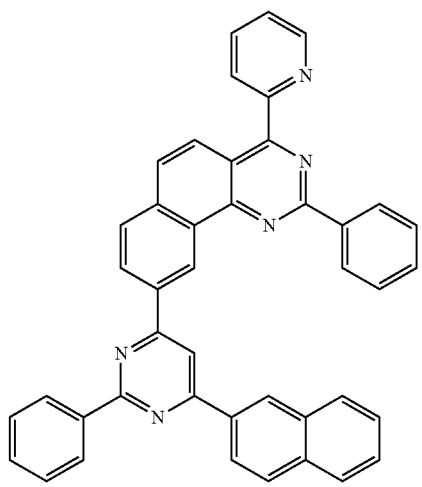
C-68 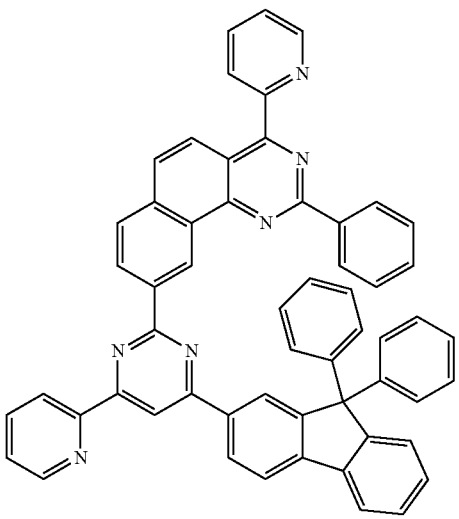
C-66 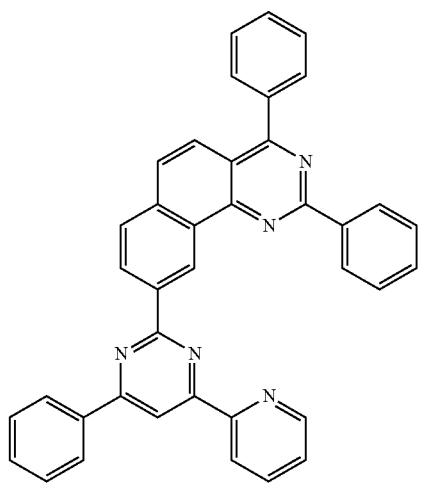
C-69 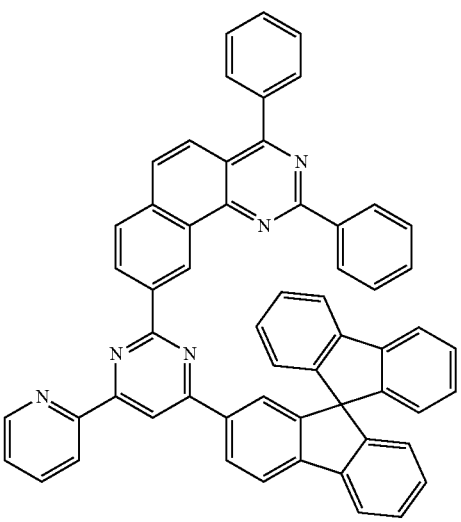
C-67 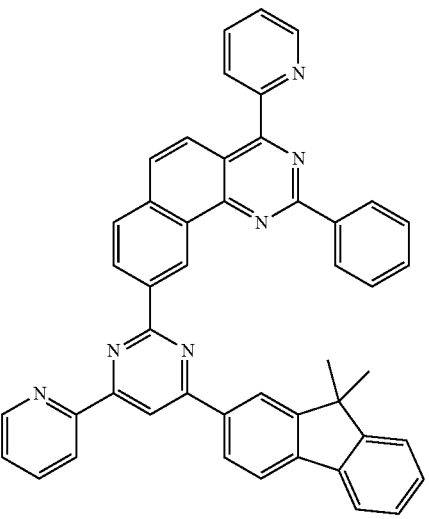
C-70 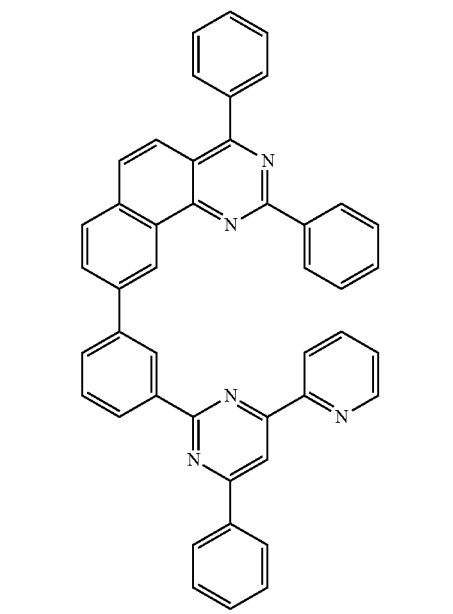

C-71
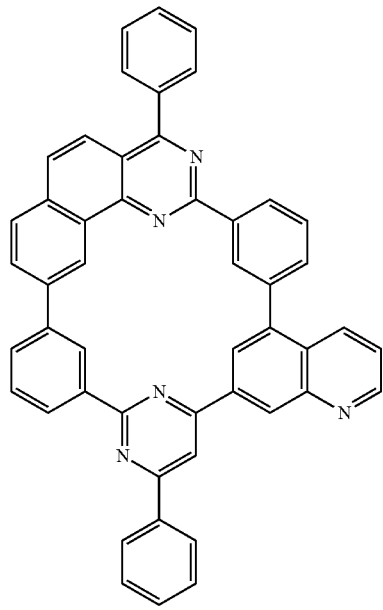
C-72
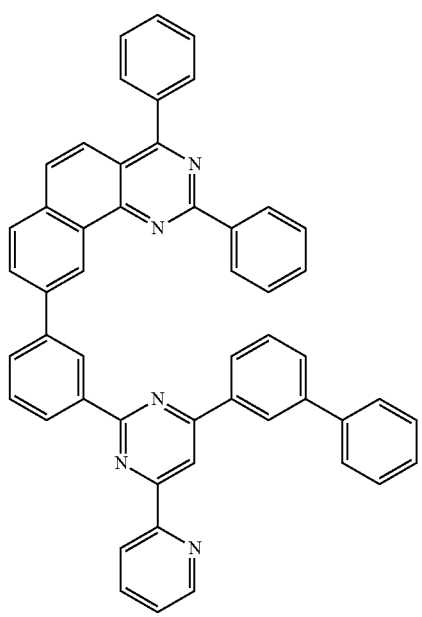
C-73
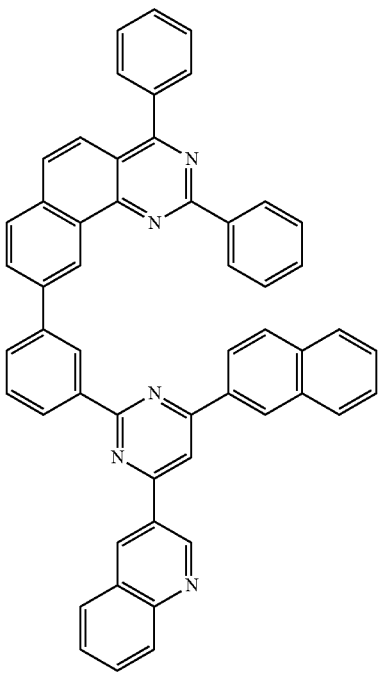
C-74
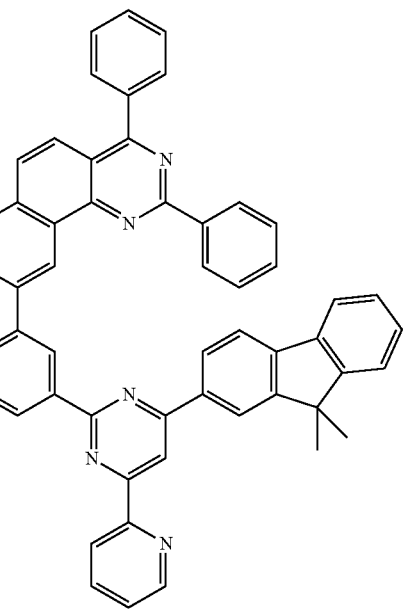

-continued
C-75
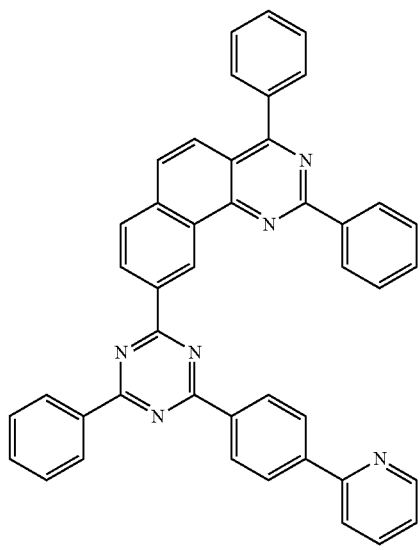
C-76
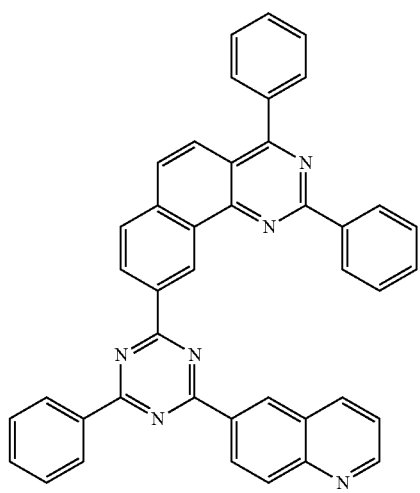
C-77
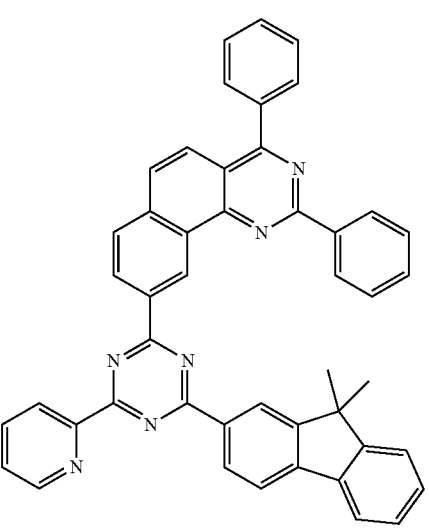
-continued
C-78
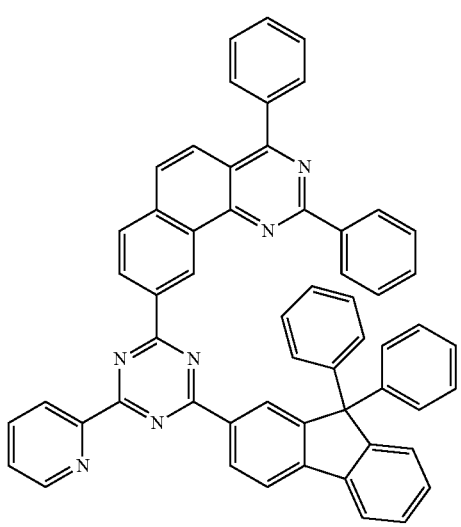
C-79
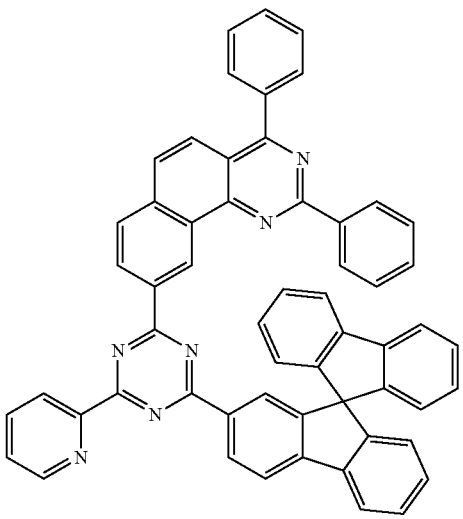
C-80
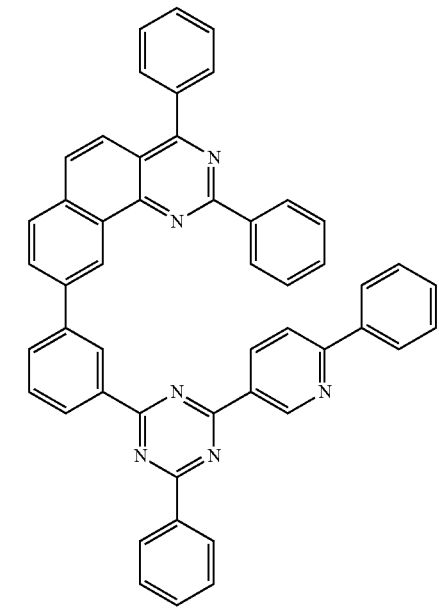

C-81 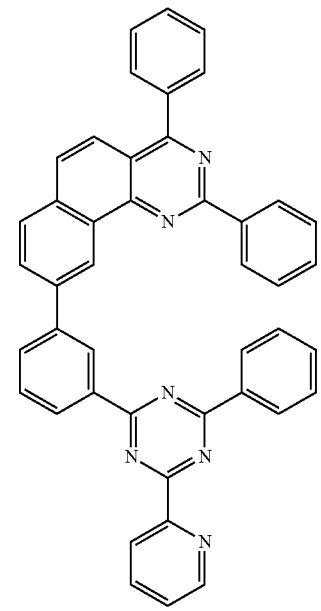
C-83 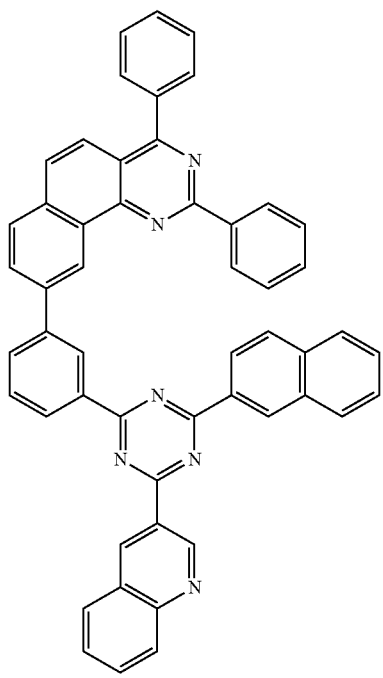
C-82 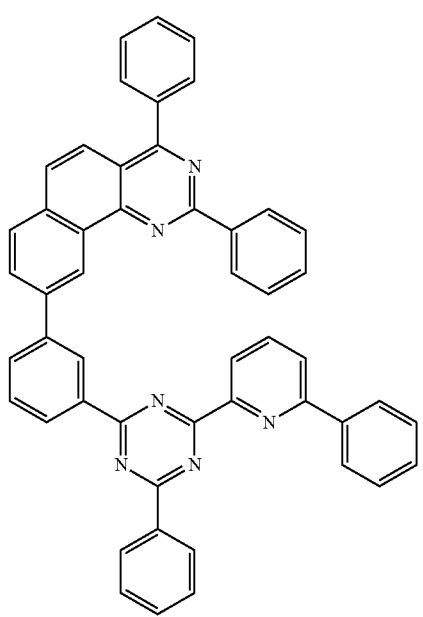
C-84 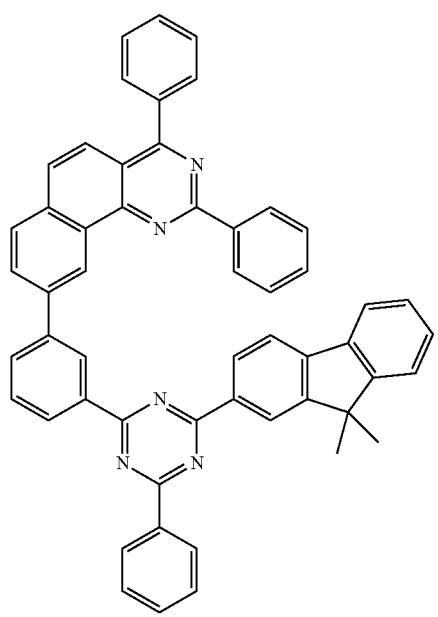

C-85
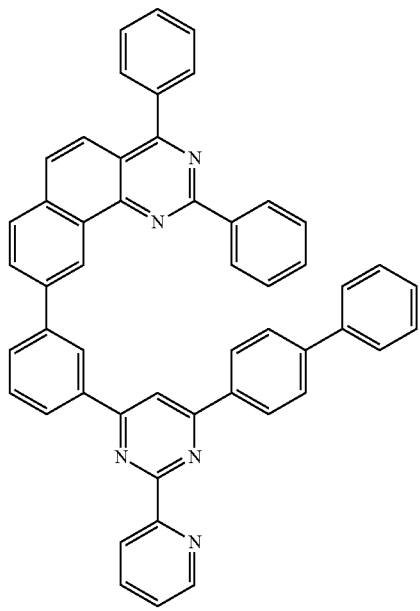
C-86
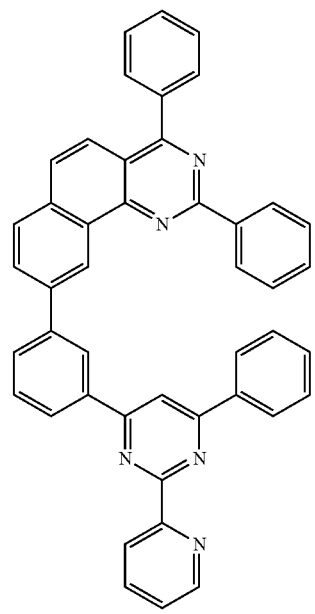
C-87
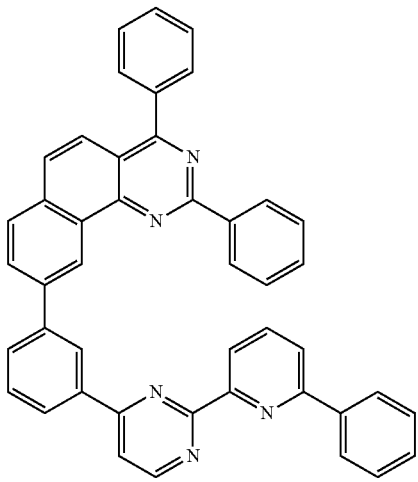
C-88
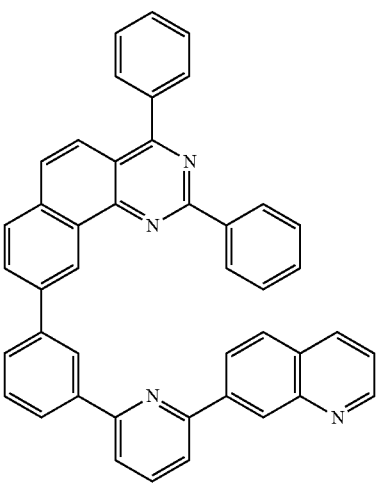
C-89
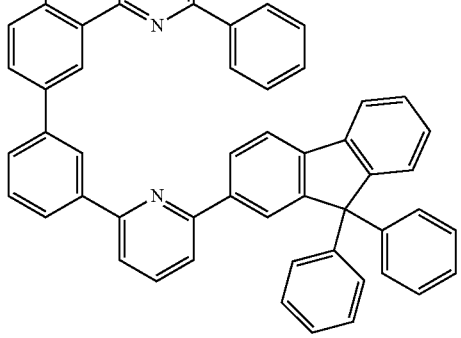

C-90
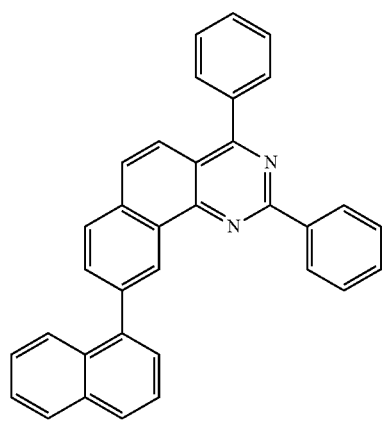
C-91
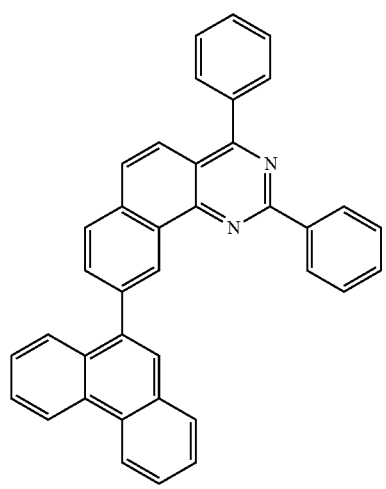
C-92
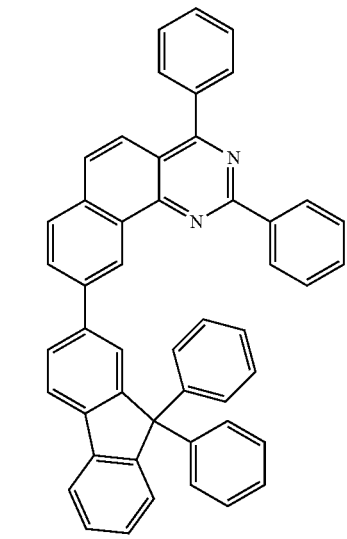
C-93
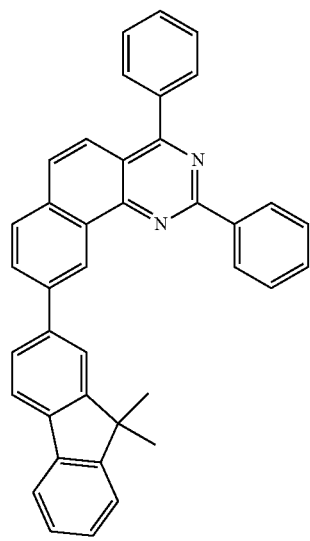
C-94
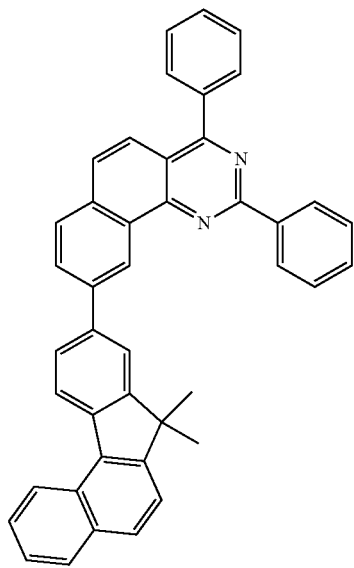

C-95
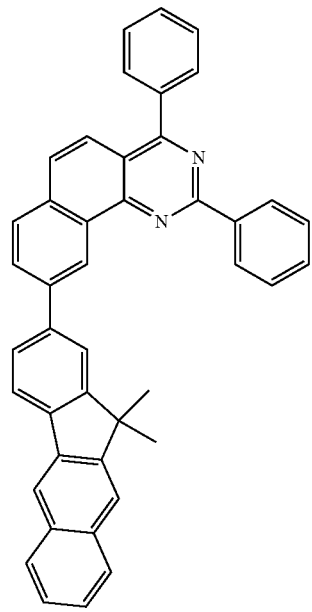
C-97
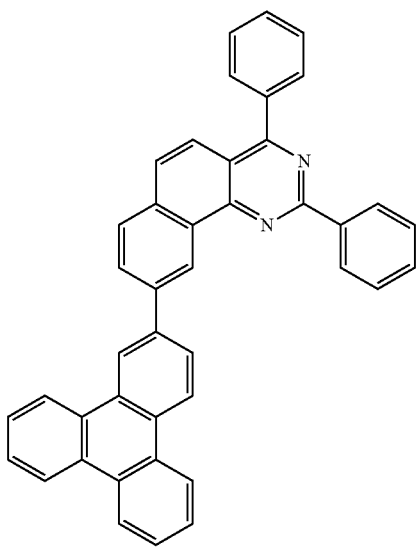
C-96
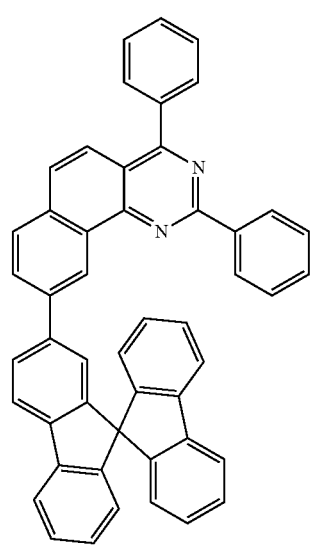
C-98
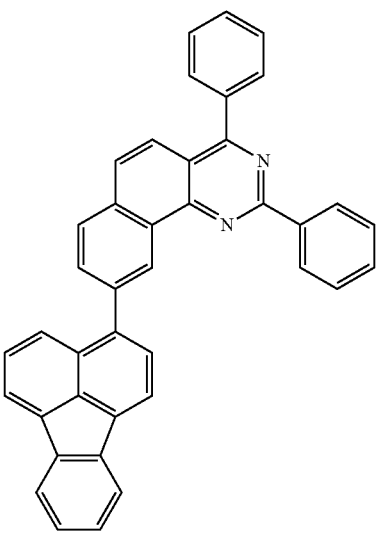

C-100
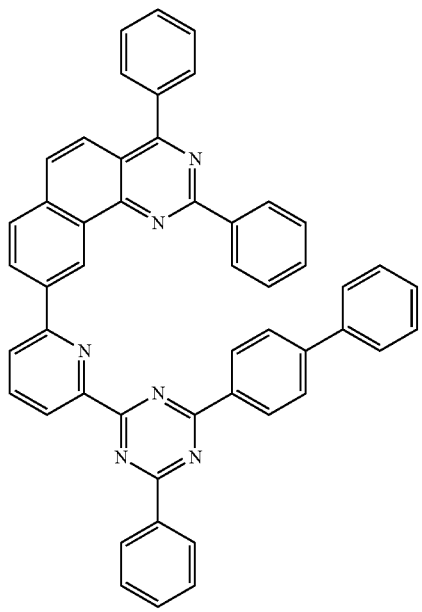
C-101
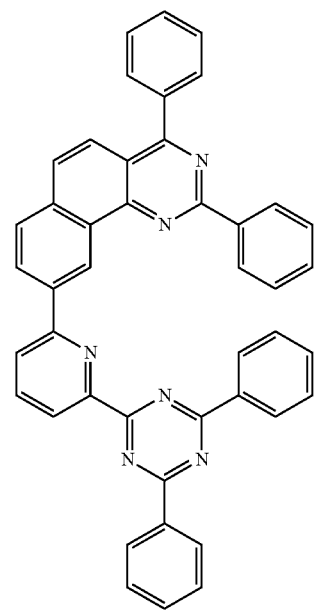
C-102
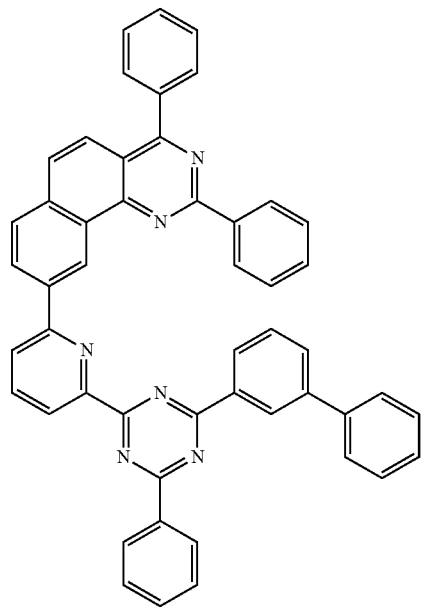
C-103
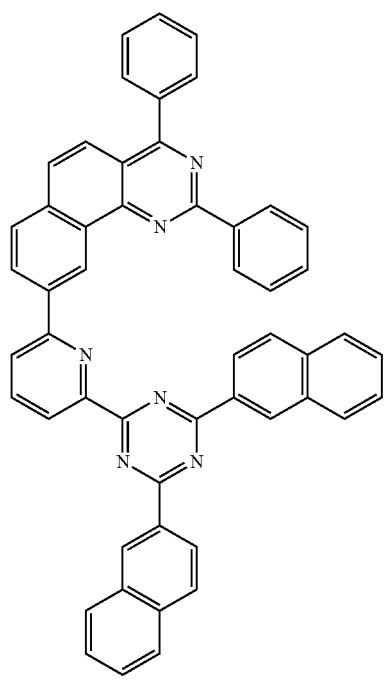

C-104
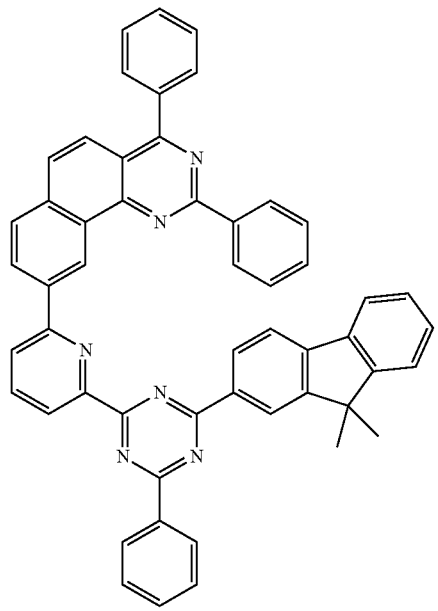
C-106
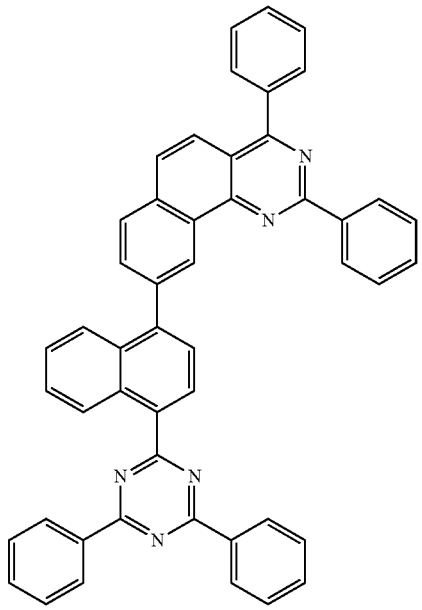
C-105
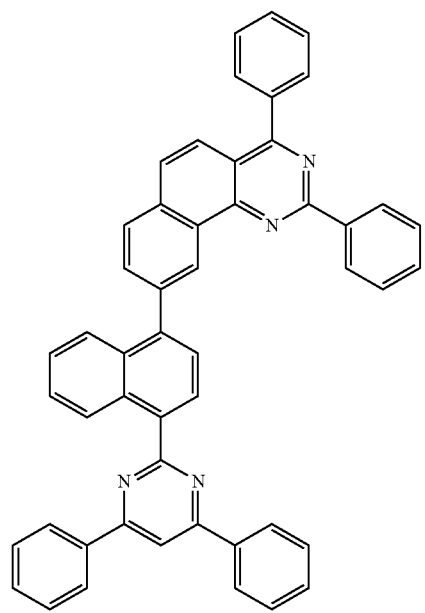
C-107
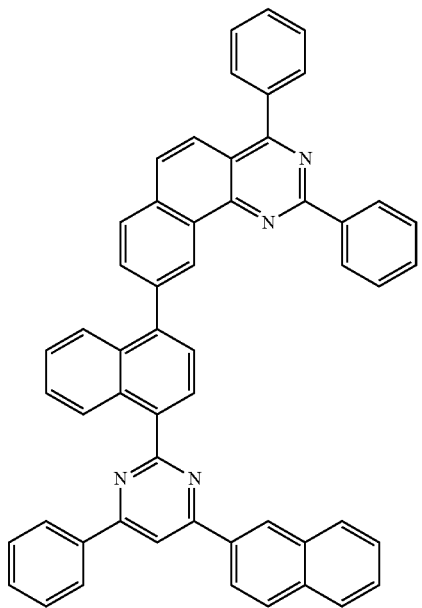

C-108
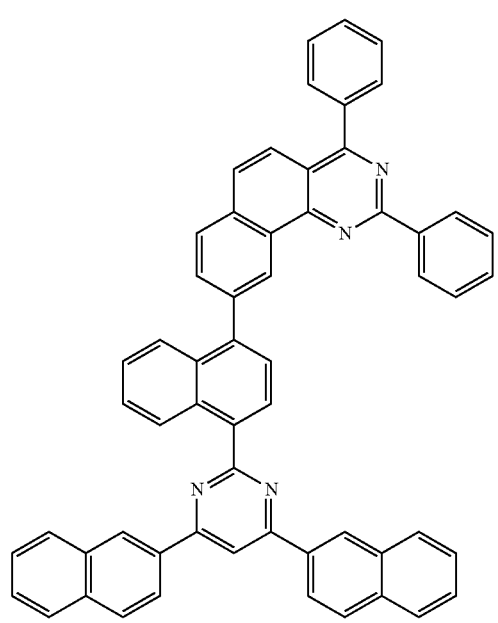
C-109
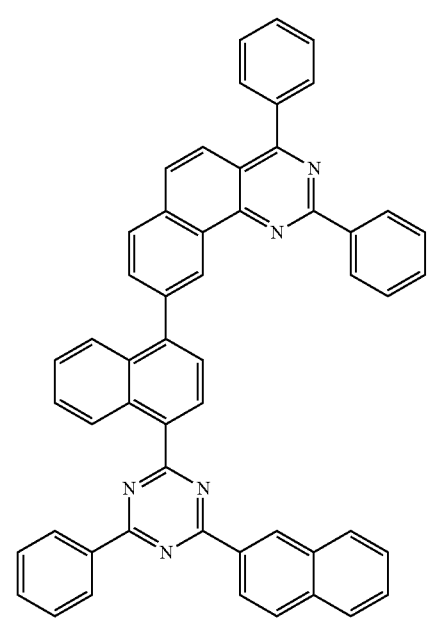
C-110
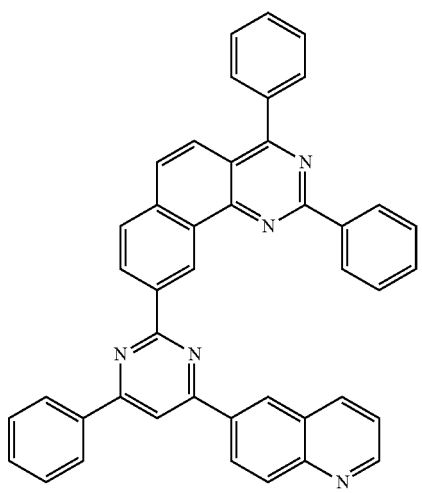
C-111
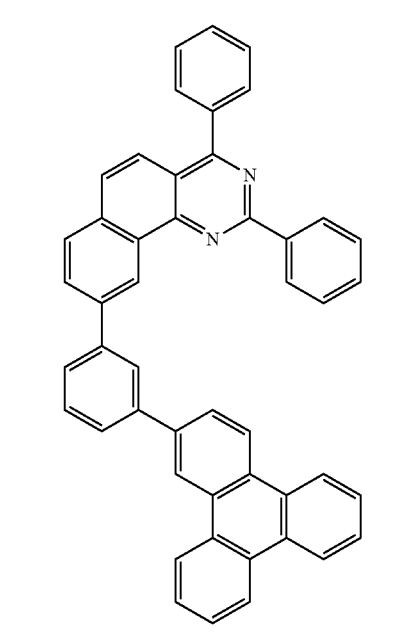

C-112
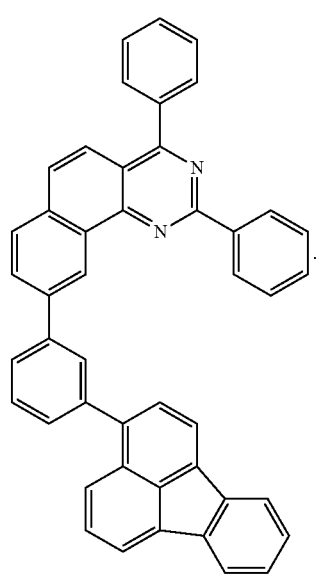
8. An organic electroluminescent device comprising the organic electroluminescent compound according to claim 1.
* * * * *